US008187600B2

(12) United States Patent
Durrant et al.

(10) Patent No.: US 8,187,600 B2
(45) Date of Patent: May 29, 2012

(54) POLYPEPTIDES CAPABLE OF BINDING TO CD64 COMPRISING ONE OR MORE HETEROLOGOUS T CELL EPITOPES AND THEIR USES

(75) Inventors: Linda Gillian Durrant, Nottingham (GB); Tina Parsons, Nottingham (GB); Adrian Robins, Nottingham (GB)

(73) Assignees: Scancell Limited, Nottingham (GB); Cancer Research Technology Limited, London (GB)

( * ) Notice: Subject to any disclaimer, the term of this patent is extended or adjusted under 35 U.S.C. 154(b) by 0 days.

(21) Appl. No.: 12/805,752

(22) Filed: Aug. 18, 2010

(65) Prior Publication Data

US 2011/0165180 A1 Jul. 7, 2011

Related U.S. Application Data

(63) Continuation of application No. 10/470,045, filed as application No. PCT/GB02/00354 on Jan. 28, 2002, now abandoned.

(30) Foreign Application Priority Data

Jan. 26, 2001 (GB) .................................. 0102145.0

(51) Int. Cl.
*A61K 39/395* (2006.01)
(52) U.S. Cl. ................ 424/133.1; 424/184.1; 424/192.1; 530/387.3; 530/806
(58) Field of Classification Search ........................ None
See application file for complete search history.

(56) References Cited

U.S. PATENT DOCUMENTS

| 5,969,109 | A | 10/1999 | Bona et al. |
| 7,067,110 | B1 | 6/2006 | Gillies et al. |
| 2004/0248113 | A1 | 12/2004 | Sette et al. |
| 2005/0261229 | A1 | 11/2005 | Gillies et al. |

FOREIGN PATENT DOCUMENTS

| WO | WO 9009804 A1 * | 9/1990 |
| WO | WO-95/31483 A1 | 11/1995 |
| WO | WO-96/19584 A1 | 11/1996 |
| WO | WO-00/64488 A3 | 11/2000 |
| WO | WO-01/07081 A1 | 2/2001 |

OTHER PUBLICATIONS

Zaghouani et al., Eur J Immunol. Nov. 1993;23(11):2746-50.*
M. Noguchi, et al., CD4[30] cytolytic T cell clones that recognize polymorphism of HLA-DRβ3 chains, Clin. Exp. Immunol. 1990, vol. 80, pp. 448-453.
Armelle Regnault, et al., Fcγ Receptor-mediated Induction of Dendritic Cell Maturation and Major Histocompatibility Complex Class I-restricted Antigen Presentation after Immune Complex Internalization, J. Exp. Med., The Rockefeller University Press, Jan. 18, 1999, vol. 189, No. 2, pp. 371-380.
Ana Rodriguez, et al., Selective transport of internalized antigens to the cytosol for MHC class I presentation in dentritic cells, Nature Cell Biology, Oct. 1999, vol. 1, pp. 362-368.
Altuvia, Yael, et al., Sequence Signals for Generation of Antigenic Peptides by the Proteasome: Implications for Proteasomal Cleavage Mechanism, J. Mol. Biol. (2000), 295:879-890.
Amino Acid Structure, New England BioLabs, Inc., Feb. 12, 2010, pp. 1-2.
Bona, Constantin, et al., Immunogenicity of Microbial Peptides Grafted in Self Immunoglobulin Molecules, Cellular and Molecular Biology, 1994, 40 (Suppl. I), pp. 21-30.
Brumeanu, T.D. et al., "Engineering of doubly antigenized immunoglobulins expressing T and B viral epitopes," Immunotechnology 2: 85-95 (1996).
Durrant, L.G., "An Idiotypic Replica of Carcinoembryonic Antigen Inducing Cellular and Humoral Responses Directed Against Human Colorectal Tumours," Int. J. Cancer, 50: 811-816 (1992) (XP-001041433).
Durrant, Lindy G. et al., "105AD7 Cancer Vaccine Stimulates Anti-Tumor Helper and Cytotoxic T-Cell Responses in Colorectal Cancer Patients but Repeated Immunisations are Required to Maintain These Responses," Int. J. Cancer 85: 87-92, (2000) (XP-001041439).
Durrant, Lindy G., "Human Anti-Idiotypic Antibodies Can Be Good Immunogens as They Target FC Receptors on Antigen-Presenting Cells Allowing Efficient Stimulation of Both Helper and Cytotoxic T-Cell Responses," Int. J. Cancer, 92: 414-420 (2001) (XP-001041422).
Fridman, Wolf F., Fc receptors and immunoglobulin binding factors, FASEB J., 1991, 5:2684-2690.
Guyre, Paul M. et al., "Increased potency of Fc-receptor-targeted antigens," Cancer Immunol Immunother 45: 146-148 (1997) (XP-000942168).
Kuttler, Christina, et al., An Algorithm for the Prediction of Proteasomal Cleavages, J. Mol. Biol, (2000), 298:417-429.
Liu, Chunlei et al., "FcγRI-Targeted Fusion Proteins Result in Efficient Presentation by Human Monocytes of Antigenic and Antagonist T Cell Epitopes," J. Clin. Invest. 98(9): 2001-2007 (Nov. 1996) (XP-002131533).
Naseem, Farah, et al., Effect of Ethylene Glycol and Polyethylene Glycol on the Acid-Unfolded State of Trypsinogen, Journal of Protein Chemistry, Nov. 2003, vol. 22., Nos. 7/8, pp. 677-682.
Vitetta, Ellen S.,et al., Considering Therapeutic Antibodies, Science, Jul. 21, 2006, vol. 313.
Zaghouani, Habib, et al., "Presentation of a Viral T Cell Epitope Expressed in the CDR3 Region of a Self Immunoglobulin Molecule," *Science*, 259:224-227, Jan. 8, 1993.
Zanetti, Maurizio, "Antigenized antibodies," *Nature*, 355:476-477, Jan. 30, 1992.

* cited by examiner

*Primary Examiner* — Michael Szperka
(74) *Attorney, Agent, or Firm* — Covington & Burling LLP; Andrea G. Reister; Melody Wu

(57) ABSTRACT

The invention relates to the use of a polypeptide that comprises i) a first portion comprising the part of human Fc that binds to CD64, and ii) a second portion comprising one or more heterologous T cell epitopes for stimulating a cytotoxic T cell response. The polypeptide may be an antibody that may be used to stimulate a cytotoxic T cell response against pathogens and tumor cells in patients in need of such treatment.

18 Claims, 24 Drawing Sheets

Figure 1:
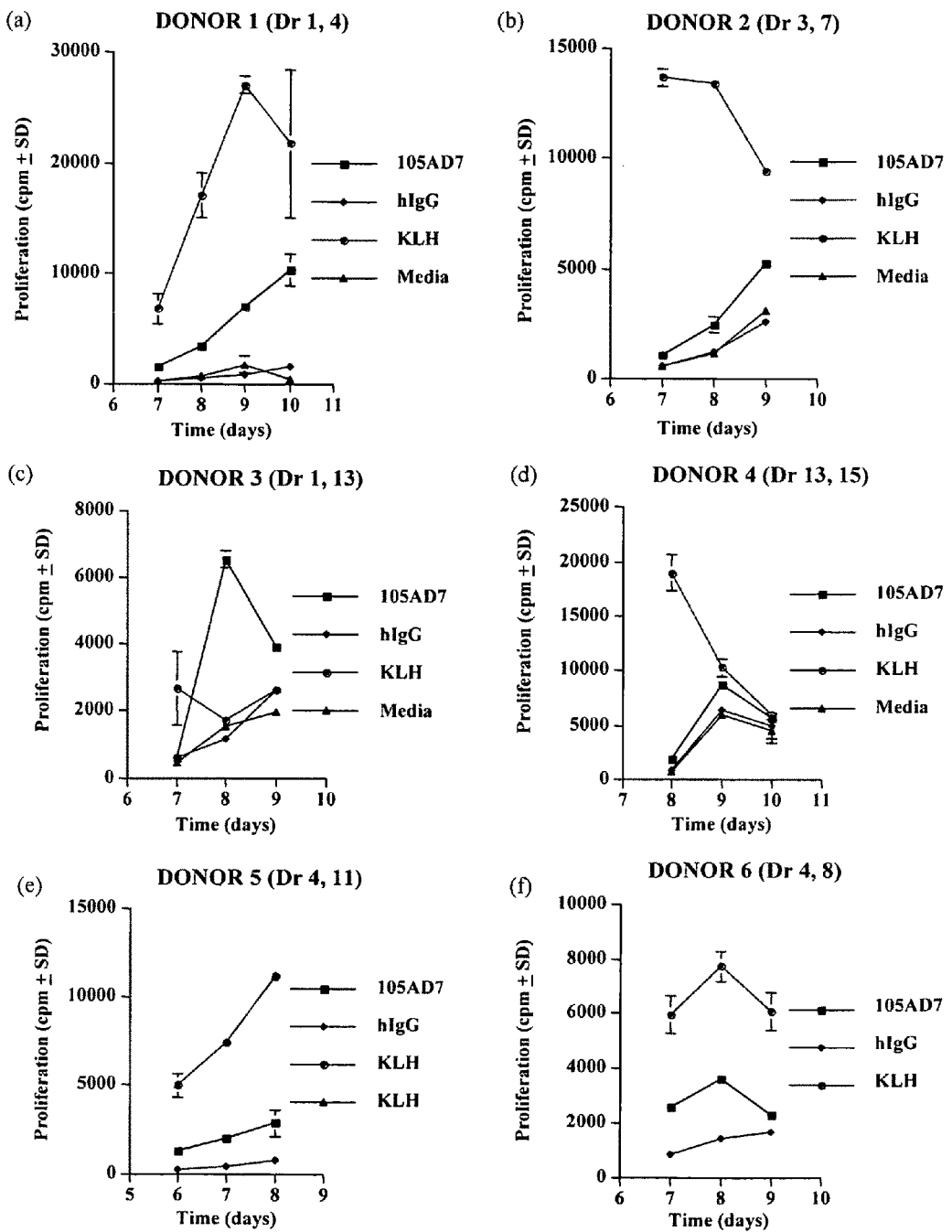

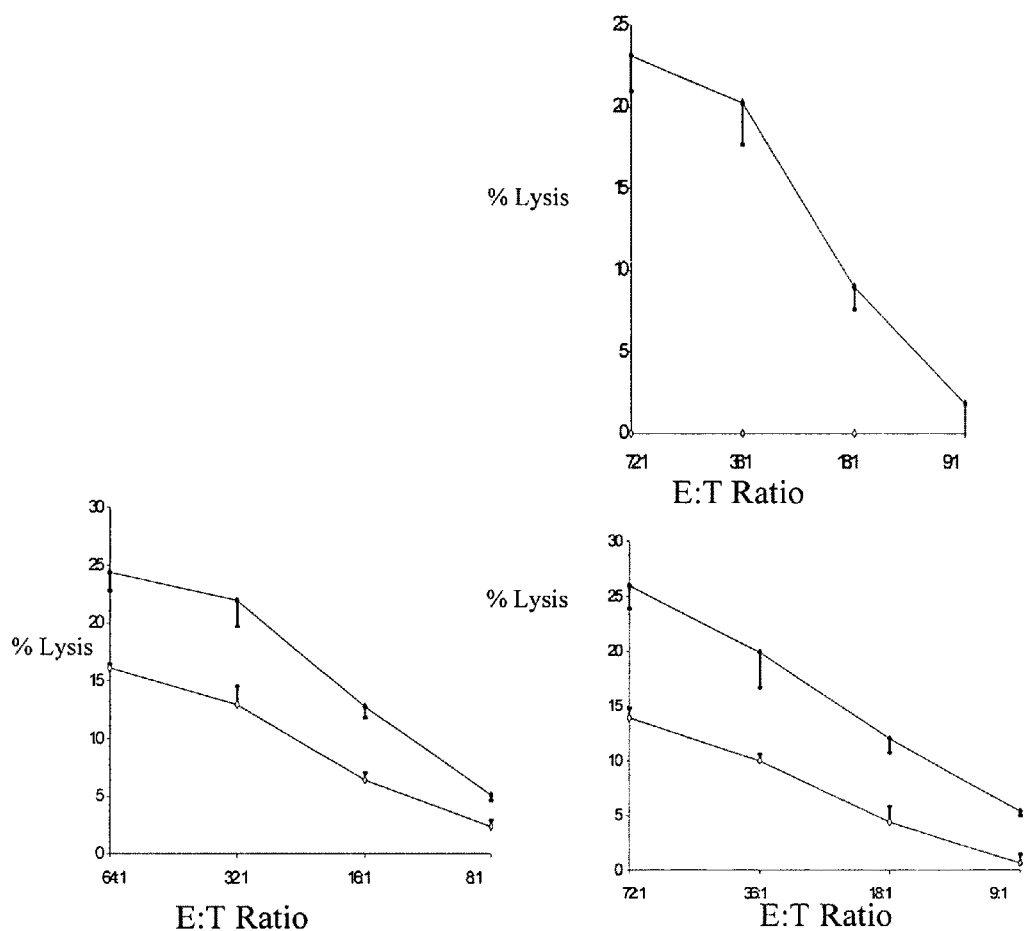
Figure 8. Cytotoxic T Cell Assay following DNA Prime / Protein Boost (open symbols target cells pulsed with irrelevant peptide. Closed symbols mice pulsed with H-2Kd peptide)

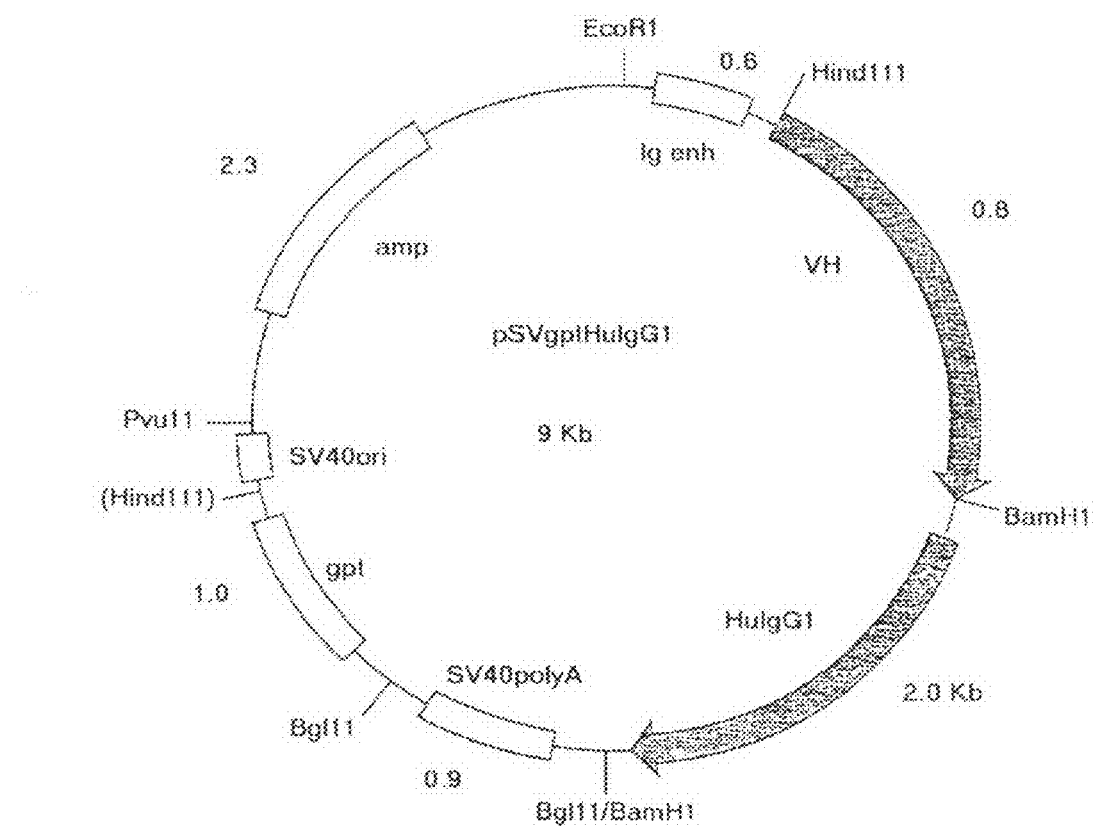
Figure 9a: Antibody Heavy Chain Expression Vector (not to scale)

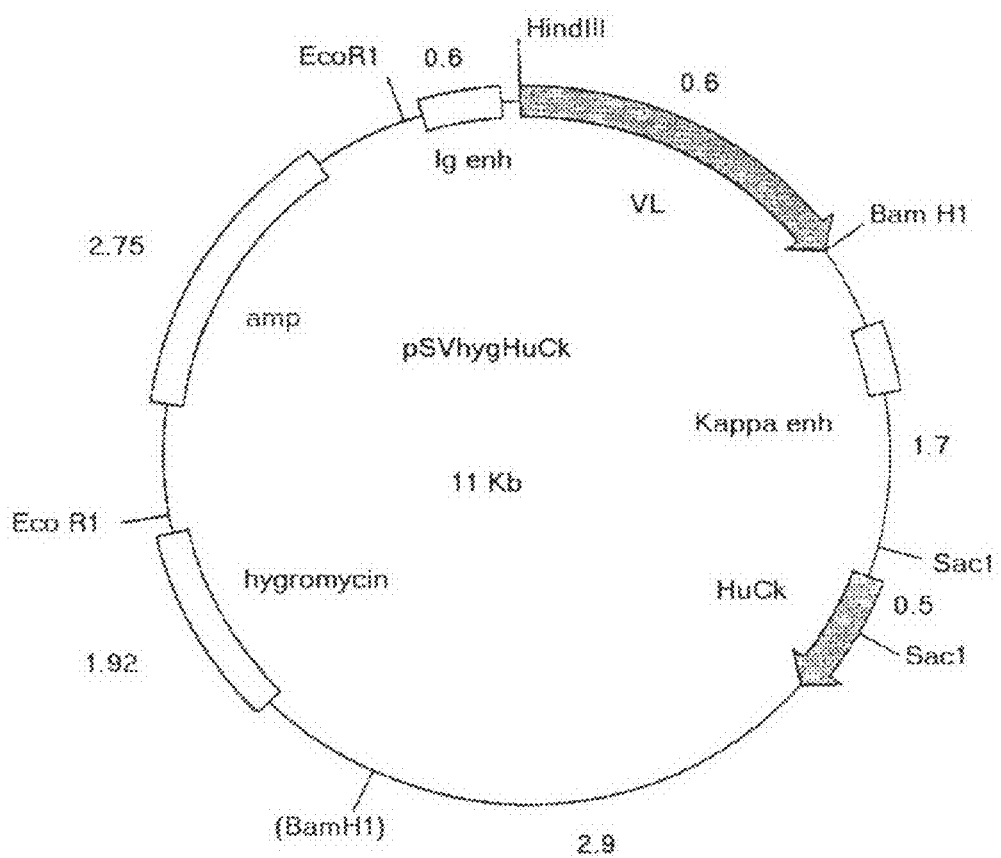
Figure 9b: Antibody Light Chain Expression Vector (not to scale)

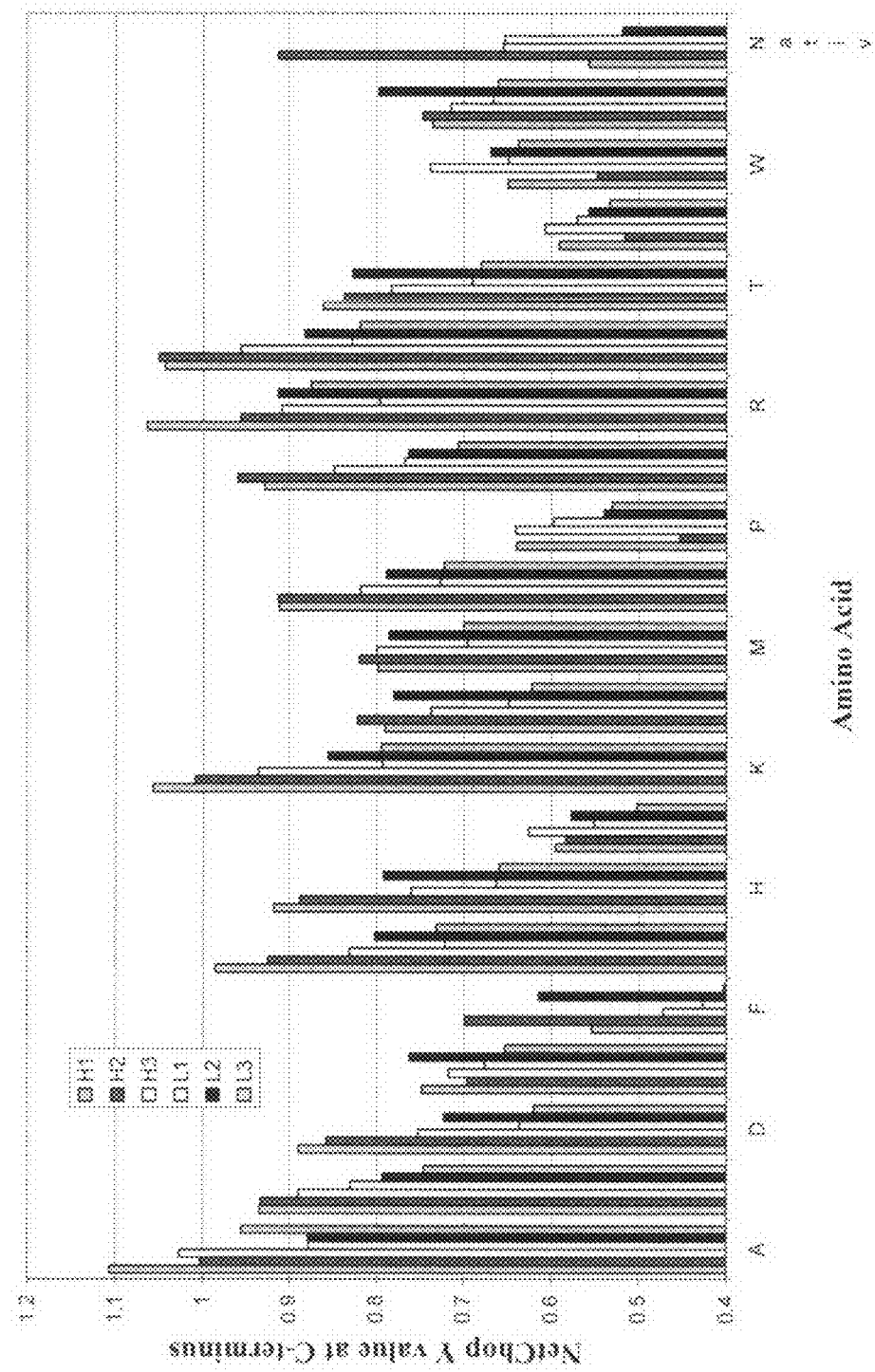
Figure 10a: Effect of C-terminal amino acid insertions, FLWGPRALV (SEQ ID NO:32) in SC100 CDRs

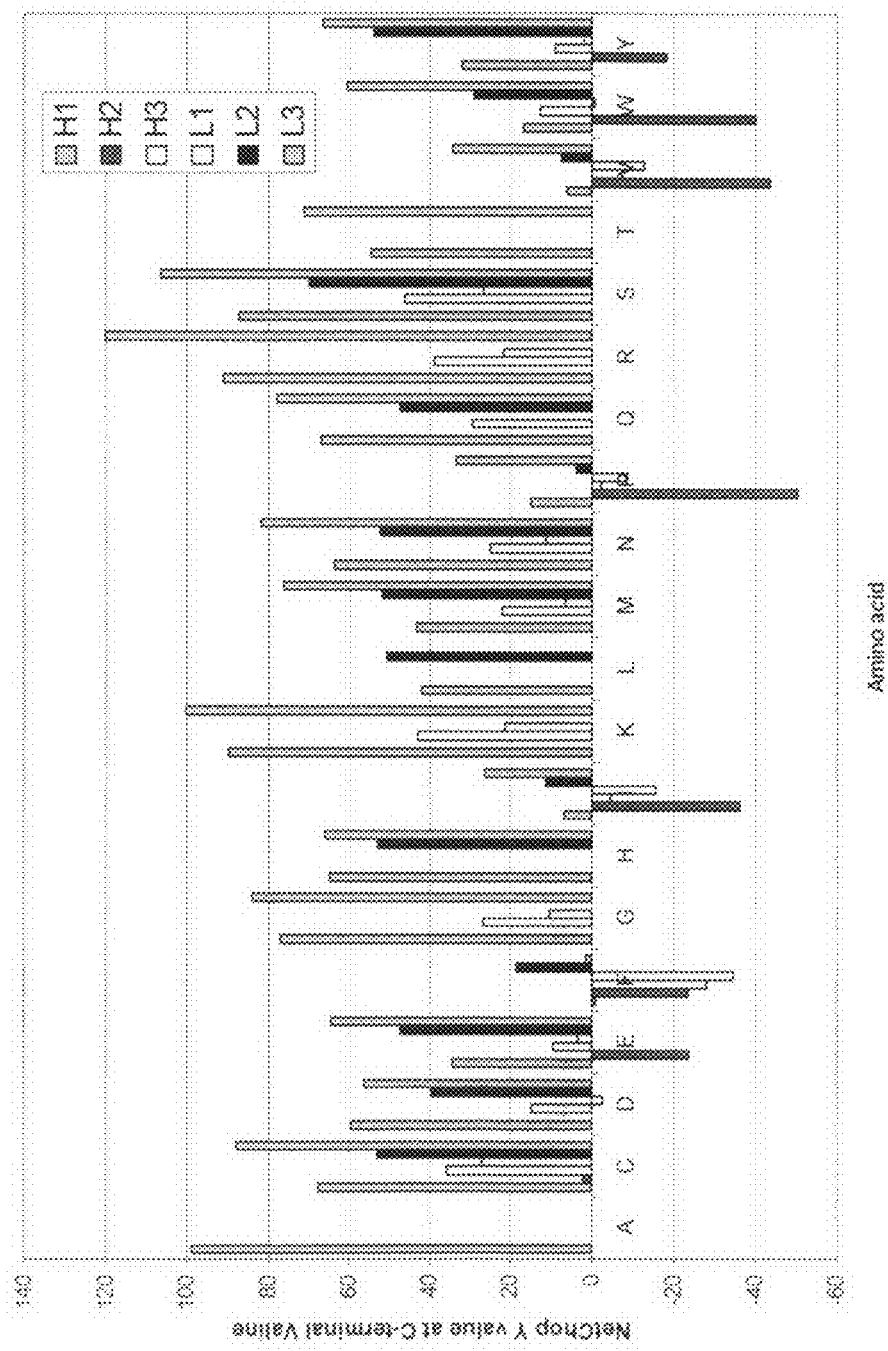

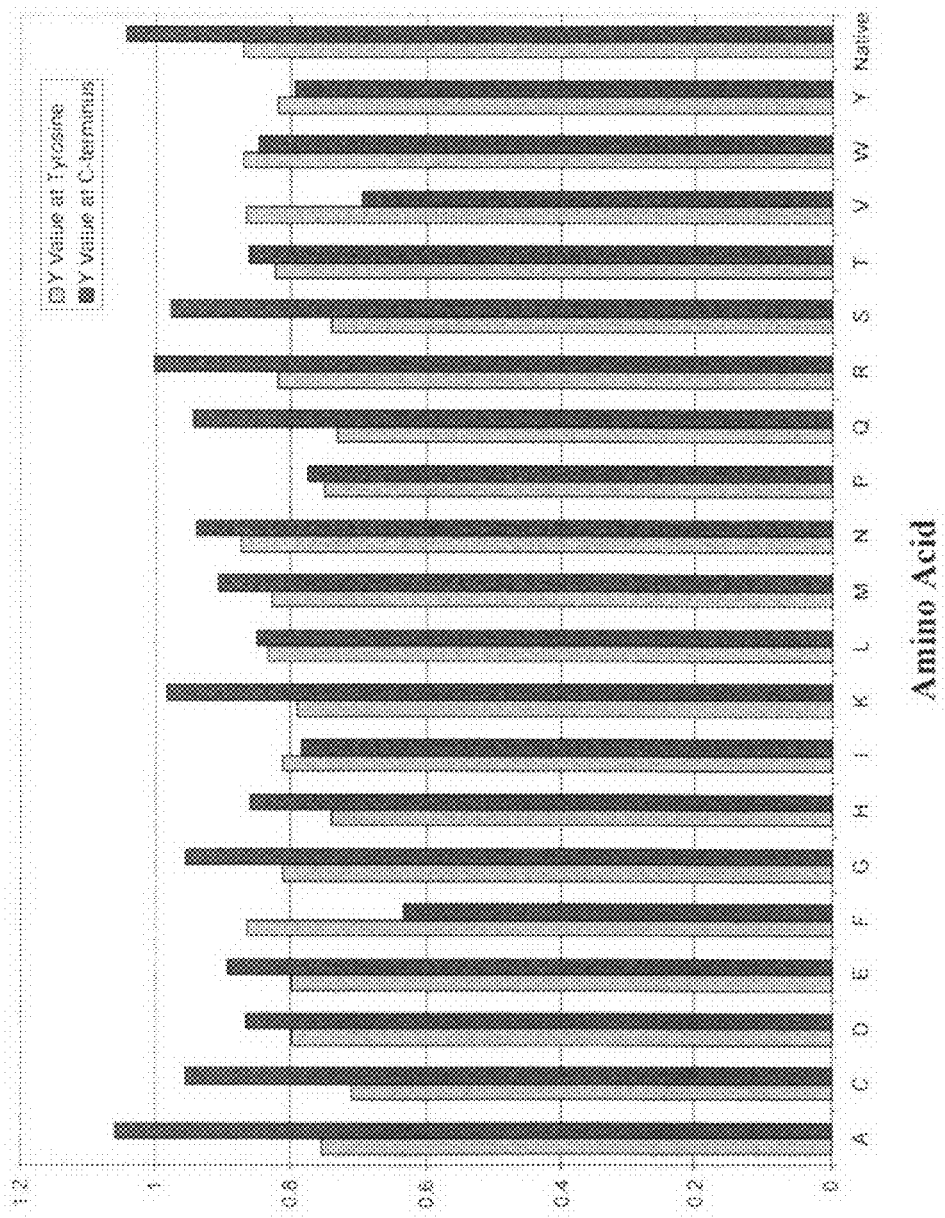
Figure 11: Effects of C Terminal Amino Acid Substitutions on the NetChop Y Value of Tyrosine (TPPAYPPNAPIL) (SEQ ID NO:99); T Helper Epitope in SC100 CDR-L1

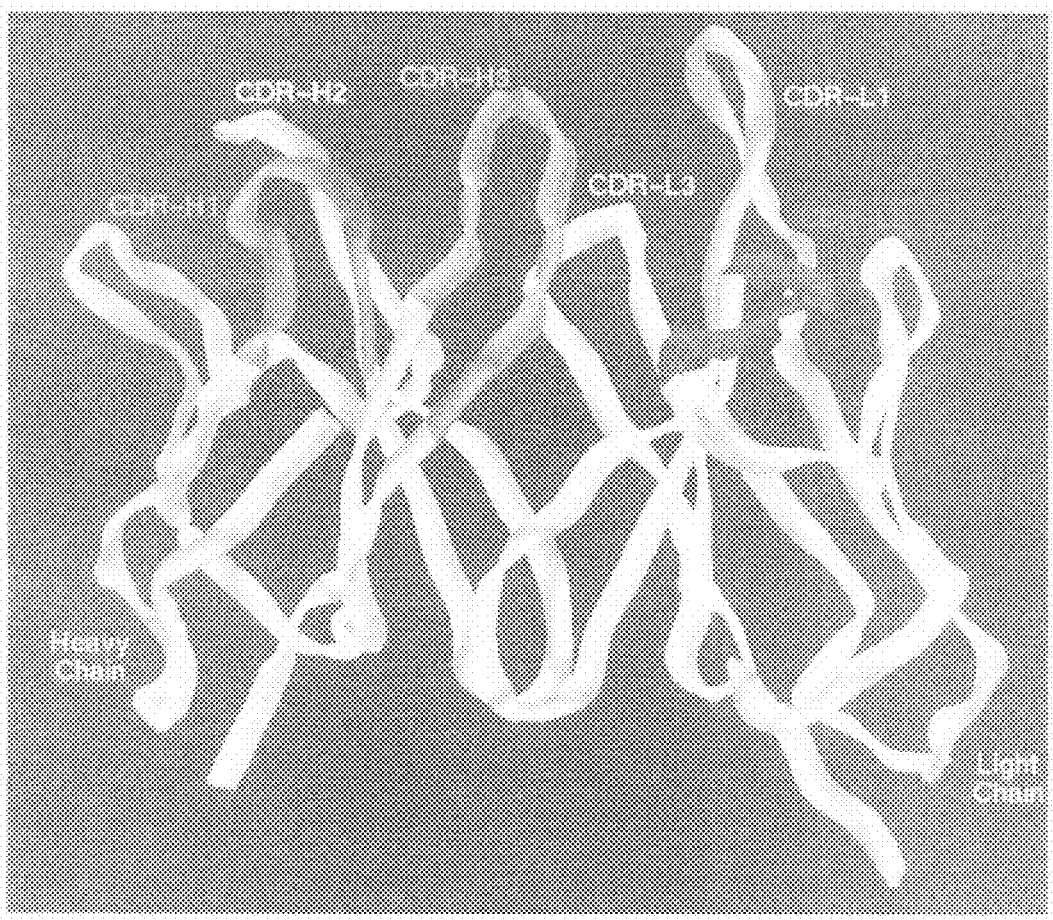
Figure 12: Molecular Model of the Fv Region of the Antibody SC100

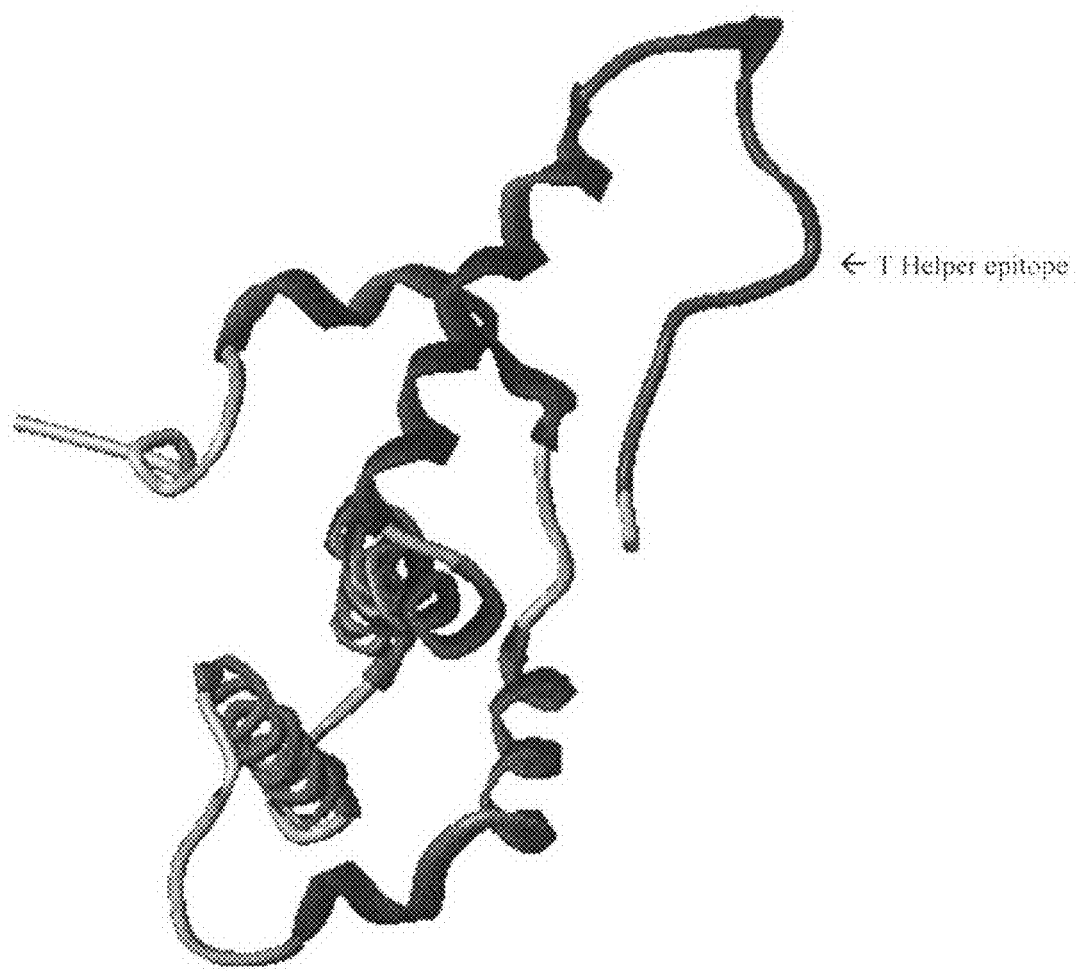
Figure 13: X-Ray Crystal Structure of the T Helper Epitope TPPAYRPPNAPIL (SEQ ID NO:31)

Figure 14: Molecular Model of the Fv Region of the Antibody SC100 (top view)
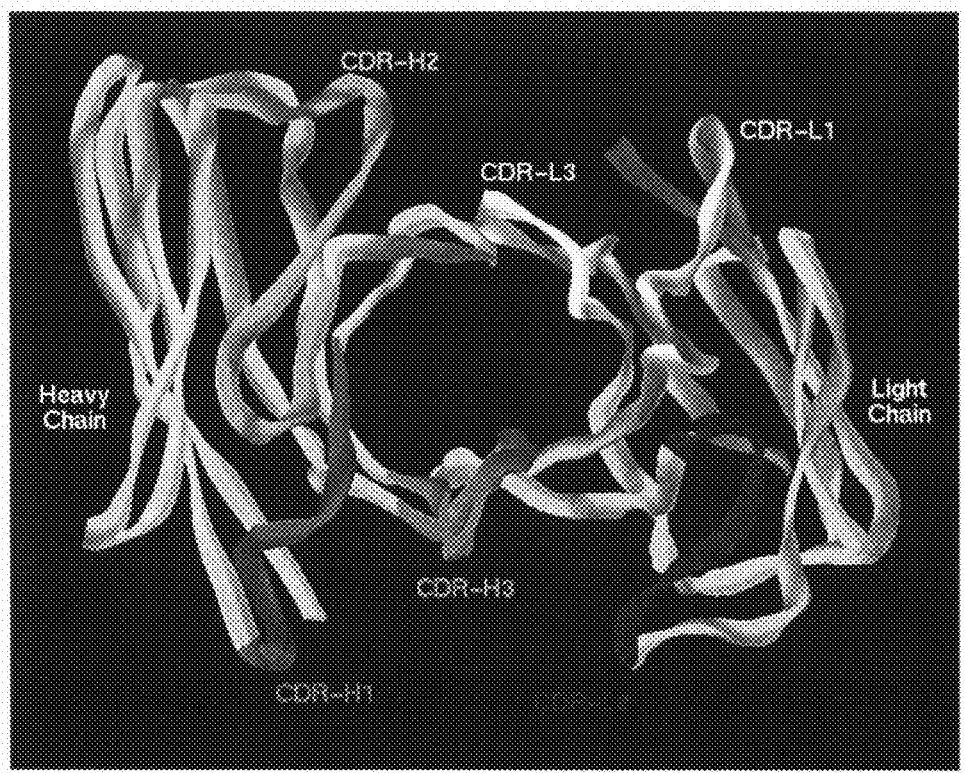
CDR-L1 is observed close to the surface, indicating that it should be structurally less constrained.

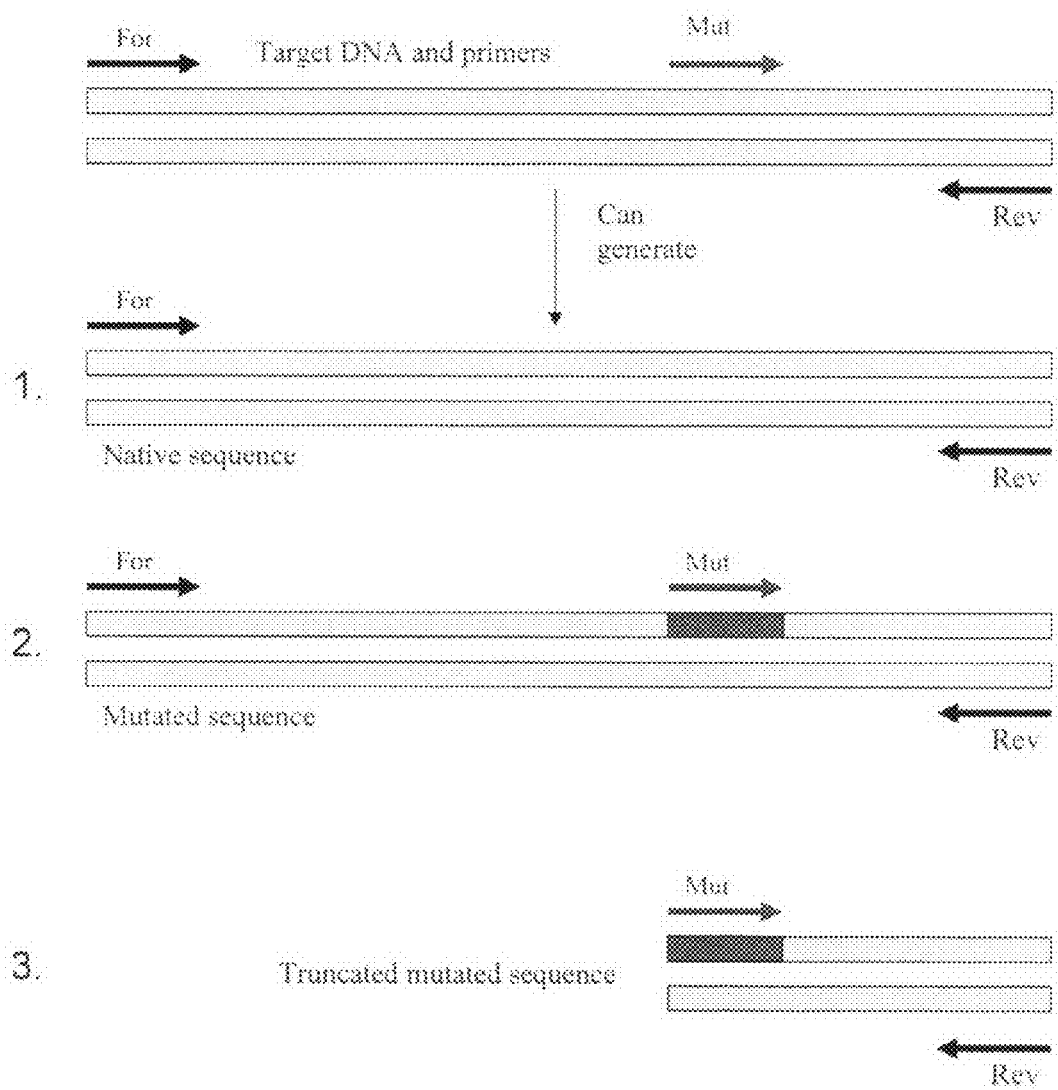

Figure 16 Agarose Gel Representation of CTL1 L3 Mutation PCR
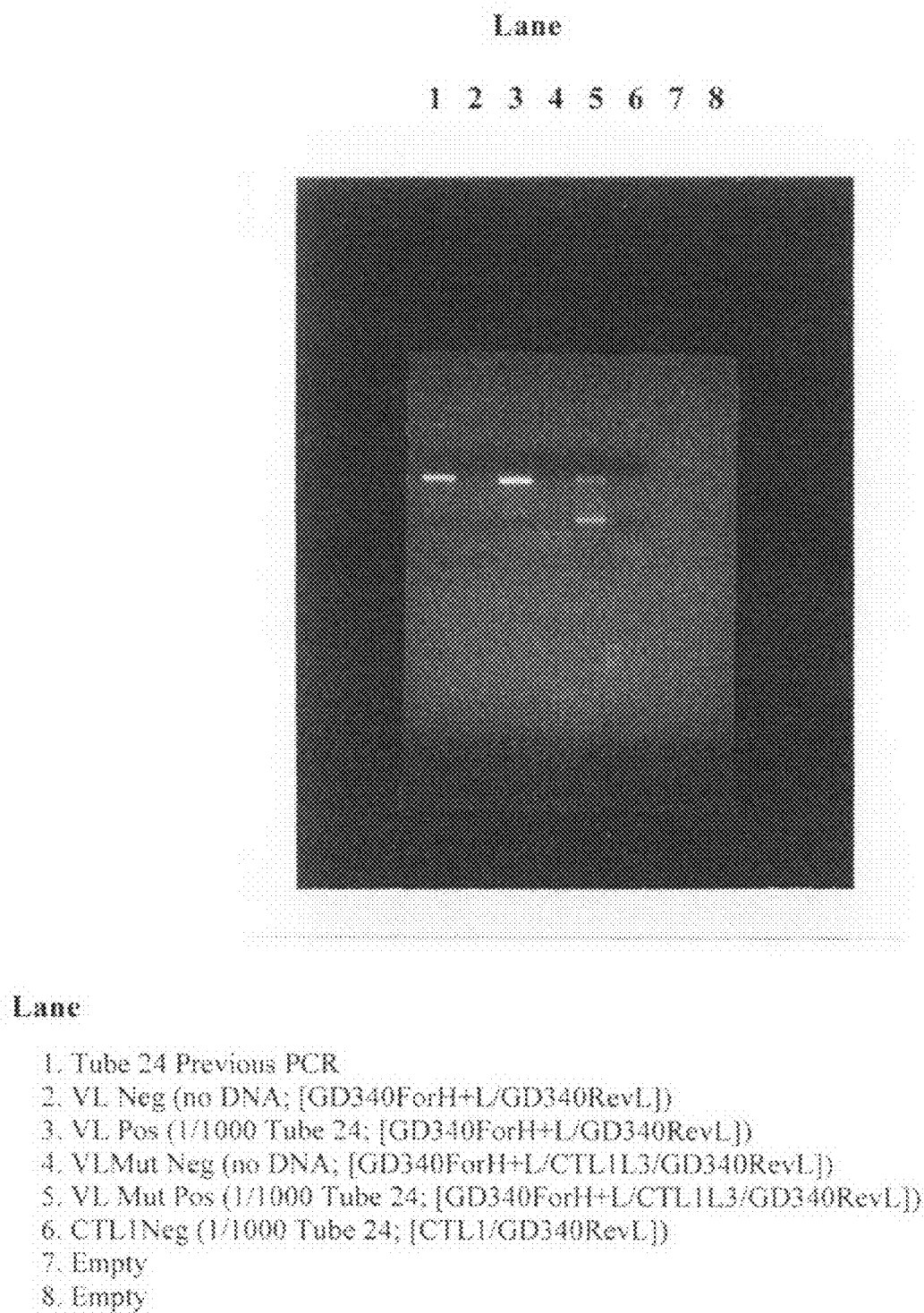
Lane
1. Tube 24 Previous PCR
2. VL Neg (no DNA; [GD340ForH+L/GD340RevL])
3. VL Pos (1/1000 Tube 24; [GD340ForH+L/GD340RevL])
4. VLMut Neg (no DNA; [GD340ForH+L/CTL1L3/GD340RevL])
5. VL Mut Pos (1/1000 Tube 24; [GD340ForH+L/CTL1L3/GD340RevL])
6. CTL1Neg (1/1000 Tube 24; [CTL1/GD340RevL])
7. Empty
8. Empty
Key: (DNA target; [primers used])

Figure 17: Agarose Gel Representation of Mutational Asymmetric PCR Results
Lane
1 2 3 4 5 6 7 8
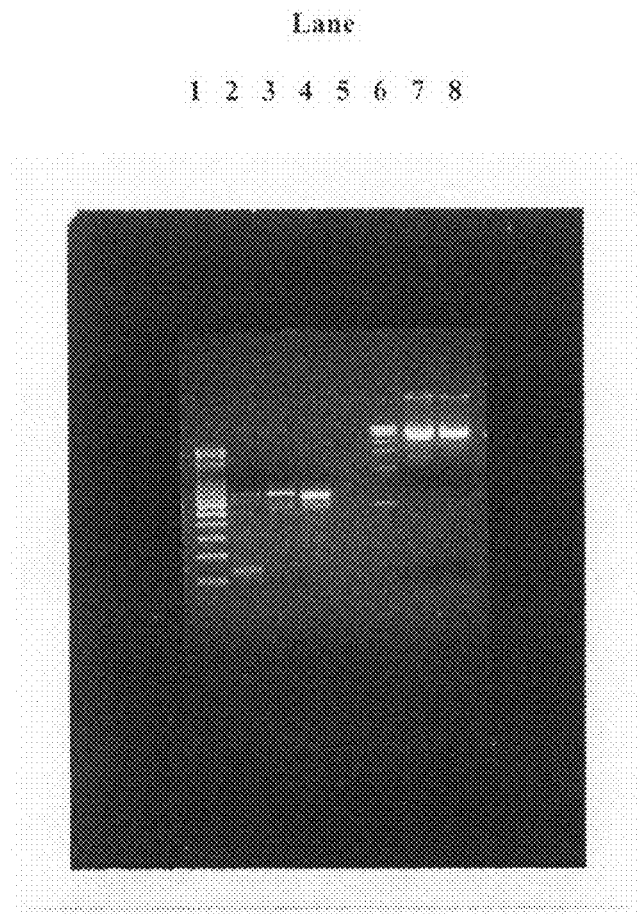
Lane
1. Promega 100bp ladder
2. Previous PCR Tube 60 (i.e. 1/1000 Tube 24; [GD340ForH+L/CTL1L3/GD340RevL])
3. VL Mut Neg (test) (10µl PCR Tube 60; [no primers])
4. VL Mut Pos (test) (10µl PCR Tube 60; [GD340ForH+L 2µl])
5. Empty
6-8 Other irrelevant samples
Key: (DNA target [primers used])

Figure 18: PCR Analysis of CDR-L3 Sequence Mutations

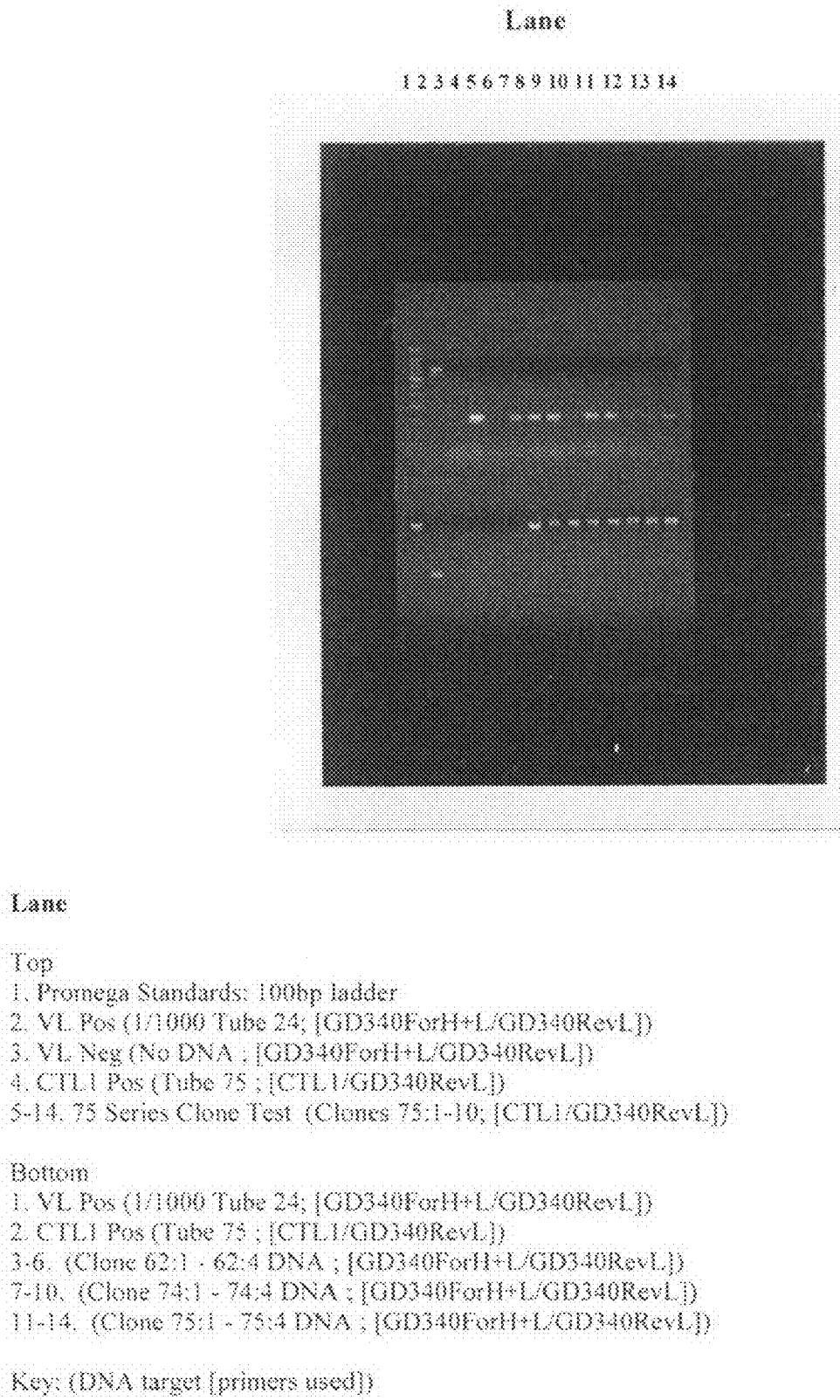

Lane

Top
1. Promega Standards: 100bp ladder
2. VL Pos (1/1000 Tube 24; [GD340ForH+L/GD340RevL])
3. VL Neg (No DNA ; [GD340ForH+L/GD340RevL])
4. CTL1 Pos (Tube 75 ; [CTL1/GD340RevL])
5-14. 75 Series Clone Test (Clones 75:1-10; [CTL1/GD340RevL])

Bottom
1. VL Pos (1/1000 Tube 24; [GD340ForH+L/GD340RevL])
2. CTL1 Pos (Tube 75 ; [CTL1/GD340RevL])
3-6. (Clone 62:1 - 62:4 DNA ; [GD340ForH+L/GD340RevL])
7-10. (Clone 74:1 - 74:4 DNA ; [GD340ForH+L/GD340RevL])
11-14. (Clone 75:1 - 75:4 DNA ; [GD340ForH+L/GD340RevL])

Key: (DNA target [primers used])

Figure19: Result of Clone 74:1 DNA Sequencing

ANTNGANTGGGCCCTCTAGATGCATGCTCGAGCGGCCGCCAGTGTGATGG
ATATCTGCAGAATTCGCCCTTTGTGAGANTCTGCCAGGATCCAACTGAGG
AAGCAAAGTTTAAATTCTACTCACGTTTGATTCCCAGCTTGGTGCCTCCA
CCGAAAACGAGGGCCCTTGGACCCCACAGGAAGCAGTAATAAATTCCCAG
ATCCTCAGCCTCCACTCTGCTGATCTTGAGTGTGAAATCTGTCCCTGATC
CACTGCCACTGAATCTGTCTGGGACCCCAGAAAATCGGTTGGAAACTTTG
TAGATCAGGAGCTTTGGAGACTGGCCTGGTTTCTGCAGGTACCATTCTAA
ATAGGTGTTTCCATTACTATGTACAATGCTCTGACTAGATCTGCAAGAGA
TGGAGGCTTGATCCCCAAGACTGACAGGCAGGGAGAGTGGAGTTTGGGTC
ATCAACACATCGGAGTGGACACCTGTGGAGAGAAAGGCAAAGTGGATGTC
ATTGTCACCCATATATATGTCCAGACCTCAAGCCTGCTACTGTGAGCCCC
TTACCTGTAGCTGTTGCTACCAAGAAGAGGATGATACAGCTTCCATCCCA
TGGTGAGGTCCTGTGTGCTCAGTAACTGTAGAGAGAACTGTGATCTCATG
TTTNTCTGTNTGTGGTATAGACAAACCCTATATTTACCATGTACGATTCA
NAGGATTTGCATATTTCATAAGCTTGGGCTGCANGNTCGACAAGGGCCGA
ATTTCCAGCCACACTTGGCGGCCCGTTACCTAGTGGGATCCCGAGCTTCG
GTACCCNAGCNTTGGCCGTAAATCATNGGNCCATTAGCCTGGTTTCCCTT
GNGTGGAAAATTTGGTTATTNCCGCTTACCAATTCCCACCACNAANATTA
CCGAAACCCGGGAAGCCNTTAAAGTNGTAAAANGCCCTGGGGGGNGCCTT
AATGANGNGANCTTAACCTCACCATTTATTTGCGTTNNCCCTTCACTGGG
CCNGCTTTTCCAATNCGGGGNAAAACCTTGTCGTNGCCCCT (SEQ ID NO:1)

Sequencing is from the reverse primer. Sequence in bold is reverse and complementary to the sequence shown below (underlined). This encodes the CTL peptide (in italics) indicating successful grafting of this epitope into CDR-L3.

AAC GAG GGC CCT TGG ACC CCA CAG GAA   (SEQ ID NO 2)

<u>TTC CTG TGG GGT CCA AGG GCC CTC GTT</u>   (SEQ ID NO 3)

*F    L    W    G    P    R    A    L    V*   (SEQ ID NO 4)

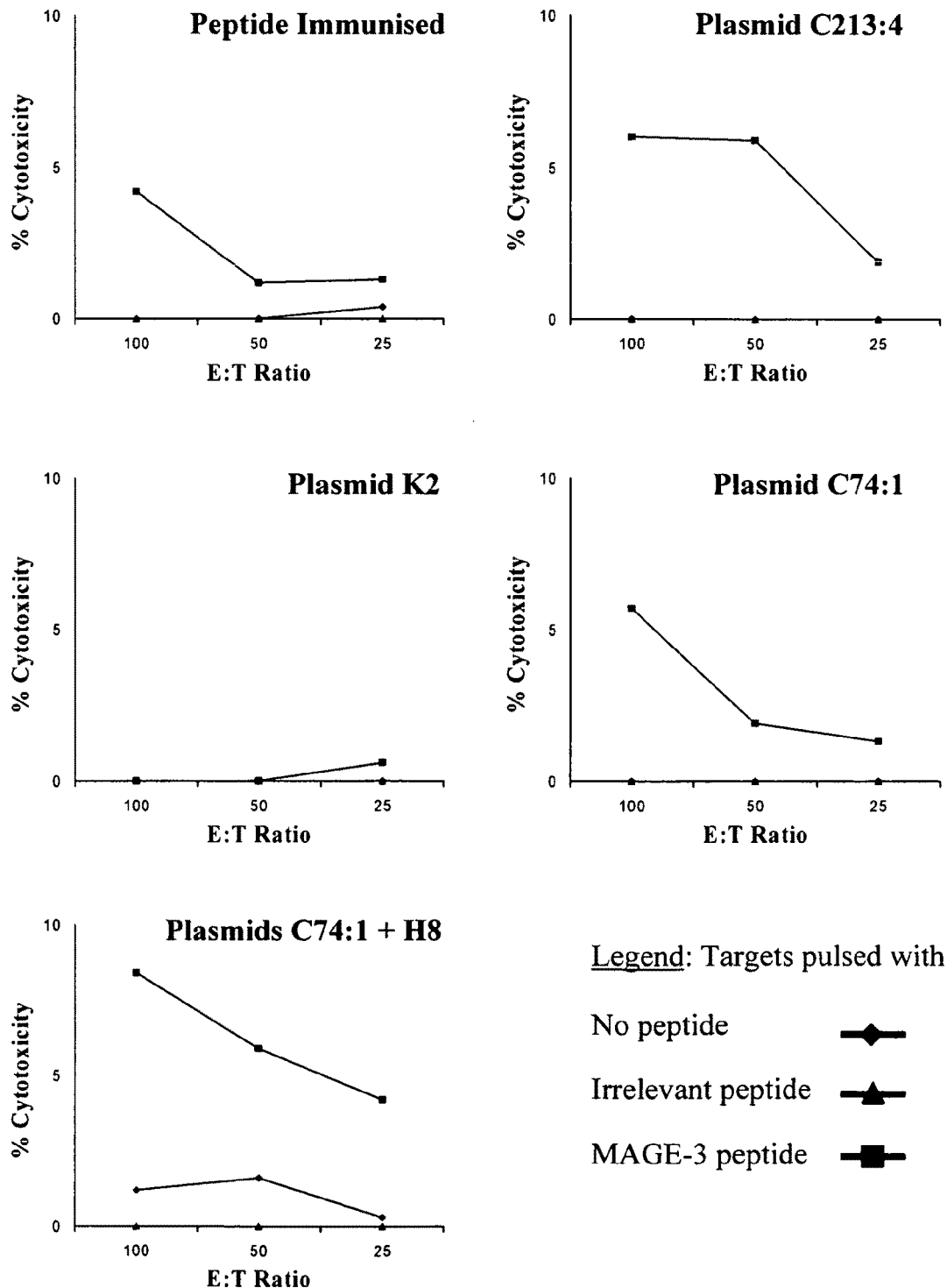
Figure 20: Results of CTL Assays

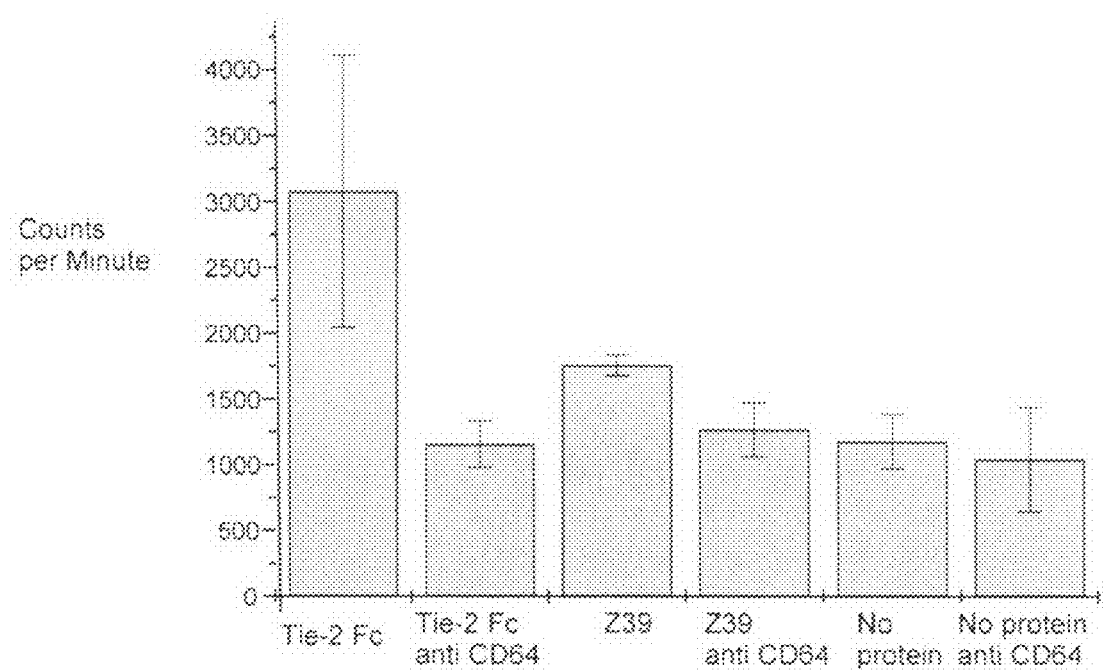

ized tocells which can process them and

SEQUENCE LISTING

```
<160> NUMBER OF SEQ ID NOS: 100

<210> SEQ ID NO 1
<211> LENGTH: 1041
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n is a or g or c or t
<220> FEATURE:
<221> NAME/KEY: misc_feature
<222> LOCATION: (4)..(4)
<223> OTHER INFORMATION: n is a or g or c or t
<220> FEATURE:
<221> NAME/KEY: misc_feature
<222> LOCATION: (7)..(7)
<223> OTHER INFORMATION: n is a or g or c or t
<220> FEATURE:
<221> NAME/KEY: misc_feature
<222> LOCATION: (79)..(79)
<223> OTHER INFORMATION: n is a or g or c or t
<220> FEATURE:
<221> NAME/KEY: misc_feature
<222> LOCATION: (654)..(654)
<223> OTHER INFORMATION: n is a or g or c or t
<220> FEATURE:
<221> NAME/KEY: misc_feature
<222> LOCATION: (660)..(660)
<223> OTHER INFORMATION: n is a or g or c or t
<220> FEATURE:
<221> NAME/KEY: misc_feature
<222> LOCATION: (701)..(701)
<223> OTHER INFORMATION: n is a or g or c or t
<220> FEATURE:
<221> NAME/KEY: misc_feature
<222> LOCATION: (734)..(734)
<223> OTHER INFORMATION: n is a or g or c or t
<220> FEATURE:
<221> NAME/KEY: misc_feature
<222> LOCATION: (736)..(736)
<223> OTHER INFORMATION: n is a or g or c or t
<220> FEATURE:
<221> NAME/KEY: misc_feature
<222> LOCATION: (807)..(807)
<223> OTHER INFORMATION: n is a or g or c or t
```

```
<220> FEATURE:
<221> NAME/KEY: misc_feature
<222> LOCATION: (811)..(811)
<223> OTHER INFORMATION: n is a or g or c or t
<220> FEATURE:
<221> NAME/KEY: misc_feature
<222> LOCATION: (827)..(827)
<223> OTHER INFORMATION: n is a or g or c or t
<220> FEATURE:
<221> NAME/KEY: misc_feature
<222> LOCATION: (830)..(830)
<223> OTHER INFORMATION: n is a or g or c or t
<220> FEATURE:
<221> NAME/KEY: misc_feature
<222> LOCATION: (852)..(852)
<223> OTHER INFORMATION: n is a or g or c or t
<220> FEATURE:
<221> NAME/KEY: misc_feature
<222> LOCATION: (871)..(871)
<223> OTHER INFORMATION: n is a or g or c or t
<220> FEATURE:
<221> NAME/KEY: misc_feature
<222> LOCATION: (893)..(893)
<223> OTHER INFORMATION: n is a or g or c or t
<220> FEATURE:
<221> NAME/KEY: misc_feature
<222> LOCATION: (896)..(896)
<223> OTHER INFORMATION: n is a or g or c or t
<220> FEATURE:
<221> NAME/KEY: misc_feature
<222> LOCATION: (918)..(918)
<223> OTHER INFORMATION: n is a or g or c or t
<220> FEATURE:
<221> NAME/KEY: misc_feature
<222> LOCATION: (926)..(926)
<223> OTHER INFORMATION: n is a or g or c or t
<220> FEATURE:
<221> NAME/KEY: misc_feature
<222> LOCATION: (933)..(933)
<223> OTHER INFORMATION: n is a or g or c or t
<220> FEATURE:
<221> NAME/KEY: misc_feature
<222> LOCATION: (945)..(945)
<223> OTHER INFORMATION: n is a or g or c or t
<220> FEATURE:
<221> NAME/KEY: misc_feature
<222> LOCATION: (956)..(956)
<223> OTHER INFORMATION: n is a or g or c or t
<220> FEATURE:
<221> NAME/KEY: misc_feature
<222> LOCATION: (958)..(958)
<223> OTHER INFORMATION: n is a or g or c or t
<220> FEATURE:
<221> NAME/KEY: misc_feature
<222> LOCATION: (961)..(961)
<223> OTHER INFORMATION: n is a or g or c or t
<220> FEATURE:
<221> NAME/KEY: misc_feature
<222> LOCATION: (987)..(988)
<223> OTHER INFORMATION: n is a or g or c or t
<220> FEATURE:
<221> NAME/KEY: misc_feature
<222> LOCATION: (1003)..(1003)
<223> OTHER INFORMATION: n is a or g or c or t
<220> FEATURE:
<221> NAME/KEY: misc_feature
<222> LOCATION: (1015)..(1015)
<223> OTHER INFORMATION: n is a or g or c or t
<220> FEATURE:
<221> NAME/KEY: misc_feature
<222> LOCATION: (1021)..(1021)
<223> OTHER INFORMATION: n is a or g or c or t
<220> FEATURE:
<221> NAME/KEY: misc_feature
<222> LOCATION: (1035)..(1035)
<223> OTHER INFORMATION: n is a or g or c or t

<400> SEQUENCE: 1
antngantgg gccctctaga tgcatgctcg agcggccgcc agtgtgatgg atatctgcag      60
```

```
aattcgccct tgtgagagant ctgccaggat ccaactgagg aagcaaagtt taaattctac    120
tcacgtttga ttcccagctt ggtgcctcca ccgaaaacga gggcccttgg accccacagg    180
aagcagtaat aaattcccag atcctcagcc tccactctgc tgatcttgag tgtgaaatct    240
gtccctgatc cactgccact gaatctgtct gggaccccag aaaatcggtt ggaaactttg    300
tagatcagga gctttggaga ctggcctggt ttctgcaggt accattctaa ataggtgttt    360
ccattactat gtacaatgct ctgactagat ctgcaagaga tggaggcttg atccccaaga    420
ctgacaggca gggagagtgg agtttgggtc atcaacacat cggagtggac acctgtggag    480
agaaaggcaa agtggatgtc attgtcaccc atatatatgt ccagacctca agcctgctac    540
tgtgagcccc ttacctgtag ctgttgctac caagaagagg atgatacagc ttccatccca    600
tggtgaggtc ctgtgtgctc agtaactgta gagagaactg tgatctcatg tttntctgtn    660
tgtggtatag acaaacccta tatttaccat gtacgattca naggatttgc atatttcata    720
agcttgggct gcangntcga caagggccga atttccagcc acacttggcg gcccgttacc    780
tagtgggatc ccgagcttcg gtacccnagc nttggccgta aatcatnggn ccattagcct    840
ggtttcccct gngtggaaaa tttggttatt nccgcttacc aattcccacc acnaanatta    900
ccgaaacccg ggaagccntt aaagtngtaa aangccctgg ggggngcctt aatgangnga    960
ncttaacctc accatttatt tgcgttnncc cttcactggg ccngcttttc caatncgggg    1020
naaaaccttg tcgtngcccc t                                               1041
```

<210> SEQ ID NO 2
<211> LENGTH: 27
<212> TYPE: DNA
<213> ORGANISM: Homo sapiens

<400> SEQUENCE: 2

```
aacgagggcc cttggacccc acaggaa                                         27
```

<210> SEQ ID NO 3
<211> LENGTH: 27
<212> TYPE: DNA
<213> ORGANISM: Homo sapiens

<400> SEQUENCE: 3

```
ttcctgtggg gtccaagggc cctcgtt                                         27
```

<210> SEQ ID NO 4
<211> LENGTH: 9
<212> TYPE: PRT
<213> ORGANISM: Homo sapiens

<400> SEQUENCE: 4

```
Phe Leu Trp Gly Pro Arg Ala Leu Val
1               5
```

<210> SEQ ID NO 5
<211> LENGTH: 27
<212> TYPE: DNA
<213> ORGANISM: Homo sapiens

<400> SEQUENCE: 5

```
ttcctaccag ctactttaac tatgact                                         27
```

<210> SEQ ID NO 6
<211> LENGTH: 9
<212> TYPE: PRT

```
<213> ORGANISM: Homo sapiens

<400> SEQUENCE: 6

Phe Leu Pro Ala Thr Leu Thr Met Thr
1               5

<210> SEQ ID NO 7
<211> LENGTH: 27
<212> TYPE: DNA
<213> ORGANISM: Homo sapiens

<400> SEQUENCE: 7
ttcctaccag ctactttaac tatggtt                                         27

<210> SEQ ID NO 8
<211> LENGTH: 9
<212> TYPE: PRT
<213> ORGANISM: Homo sapiens

<400> SEQUENCE: 8

Phe Leu Pro Ala Thr Leu Thr Met Val
1               5

<210> SEQ ID NO 9
<211> LENGTH: 27
<212> TYPE: DNA
<213> ORGANISM: Homo sapiens

<400> SEQUENCE: 9
ttagttctct gtggagtcag cttgctc                                         27

<210> SEQ ID NO 10
<211> LENGTH: 9
<212> TYPE: PRT
<213> ORGANISM: Homo sapiens

<400> SEQUENCE: 10

Leu Val Leu Cys Gly Val Ser Leu Leu
1               5

<210> SEQ ID NO 11
<211> LENGTH: 27
<212> TYPE: DNA
<213> ORGANISM: Homo sapiens

<400> SEQUENCE: 11
ttacttctct gtggagtcag cttggtc                                         27

<210> SEQ ID NO 12
<211> LENGTH: 9
<212> TYPE: PRT
<213> ORGANISM: Homo sapiens

<400> SEQUENCE: 12

Leu Leu Leu Cys Gly Val Ser Leu Val
1               5

<210> SEQ ID NO 13
<211> LENGTH: 27
<212> TYPE: DNA
<213> ORGANISM: Homo sapiens

<400> SEQUENCE: 13
ctaccagcta ctttaactat gactgtg                                         27
```

```
<210> SEQ ID NO 14
<211> LENGTH: 9
<212> TYPE: PRT
<213> ORGANISM: Homo sapiens

<400> SEQUENCE: 14

Leu Pro Ala Thr Leu Thr Met Thr Val
1               5

<210> SEQ ID NO 15
<211> LENGTH: 27
<212> TYPE: DNA
<213> ORGANISM: Homo sapiens

<400> SEQUENCE: 15
ctactagcta ctttaactat gactgtg                                        27

<210> SEQ ID NO 16
<211> LENGTH: 9
<212> TYPE: PRT
<213> ORGANISM: Homo sapiens

<400> SEQUENCE: 16

Leu Leu Ala Thr Leu Thr Met Thr Val
1               5

<210> SEQ ID NO 17
<211> LENGTH: 27
<212> TYPE: DNA
<213> ORGANISM: Homo sapiens

<400> SEQUENCE: 17
tccttcctac cagctacttt aactatg                                        27

<210> SEQ ID NO 18
<211> LENGTH: 9
<212> TYPE: PRT
<213> ORGANISM: Homo sapiens

<400> SEQUENCE: 18

Ser Phe Leu Pro Ala Thr Leu Thr Met
1               5

<210> SEQ ID NO 19
<211> LENGTH: 27
<212> TYPE: DNA
<213> ORGANISM: Homo sapiens

<400> SEQUENCE: 19
tccttactac cagctacttt aactgtg                                        27

<210> SEQ ID NO 20
<211> LENGTH: 9
<212> TYPE: PRT
<213> ORGANISM: Homo sapiens

<400> SEQUENCE: 20

Ser Leu Leu Pro Ala Thr Leu Thr Val
1               5

<210> SEQ ID NO 21
<211> LENGTH: 34
<212> TYPE: DNA
<213> ORGANISM: artificial sequence
<220> FEATURE:
```

<223> OTHER INFORMATION: Primer

<400> SEQUENCE: 21
ccagctactt taactatggt tgtggacaag ggag　　　　　　　　　　　　　　　34

<210> SEQ ID NO 22
<211> LENGTH: 34
<212> TYPE: DNA
<213> ORGANISM: artificial sequence
<220> FEATURE:
<223> OTHER INFORMATION: Primer

<400> SEQUENCE: 22
ctcccttgtc cacaaccata gttaaagtag ctgg　　　　　　　　　　　　　　　34

<210> SEQ ID NO 23
<211> LENGTH: 42
<212> TYPE: DNA
<213> ORGANISM: artificial sequence
<220> FEATURE:
<223> OTHER INFORMATION: Primer

<400> SEQUENCE: 23
agccagctta cttctctgtg gagtcagctt ggtcctttct gg　　　　　　　　　　　42

<210> SEQ ID NO 24
<211> LENGTH: 42
<212> TYPE: DNA
<213> ORGANISM: artificial sequence
<220> FEATURE:
<223> OTHER INFORMATION: Primer

<400> SEQUENCE: 24
ccagaaagga ccaagctgac tccacagaga agtaagctgg ct　　　　　　　　　　　42

<210> SEQ ID NO 25
<211> LENGTH: 37
<212> TYPE: DNA
<213> ORGANISM: artificial sequence
<220> FEATURE:
<223> OTHER INFORMATION: Primer

<400> SEQUENCE: 25
gcttccttcc tactagctac tttaactatg actgtgg　　　　　　　　　　　　　37

<210> SEQ ID NO 26
<211> LENGTH: 37
<212> TYPE: DNA
<213> ORGANISM: artificial sequence
<220> FEATURE:
<223> OTHER INFORMATION: Primer

<400> SEQUENCE: 26
ccacagtcat agttaaagta gctagtagga aggaagc　　　　　　　　　　　　　37

<210> SEQ ID NO 27
<211> LENGTH: 40
<212> TYPE: DNA
<213> ORGANISM: artificial sequence
<220> FEATURE:
<223> OTHER INFORMATION: Primer

<400> SEQUENCE: 27
caagcttcct tactaccagc tactttaact gtgactgtgg　　　　　　　　　　　　40

<210> SEQ ID NO 28

```
<211> LENGTH: 40
<212> TYPE: DNA
<213> ORGANISM: artificial sequence
<220> FEATURE:
<223> OTHER INFORMATION: Primer

<400> SEQUENCE: 28
ccacagtcac agttaaagta gctggtagta aggaagcttg                                40

<210> SEQ ID NO 29
<211> LENGTH: 27
<212> TYPE: DNA
<213> ORGANISM: Artificial sequence
<220> FEATURE:
<223> OTHER INFORMATION: Primer

<400> SEQUENCE: 29
gatctcgaga tttggggaag catggac                                             27

<210> SEQ ID NO 30
<211> LENGTH: 30
<212> TYPE: DNA
<213> ORGANISM: Artificial sequence
<220> FEATURE:
<223> OTHER INFORMATION: Primer

<400> SEQUENCE: 30
gaagatatct cctcctatat acctggccga                                          30

<210> SEQ ID NO 31
<211> LENGTH: 13
<212> TYPE: PRT
<213> ORGANISM: Homo sapiens

<400> SEQUENCE: 31

Thr Pro Pro Ala Tyr Arg Pro Pro Asn Ala Pro Ile Leu
1               5                   10

<210> SEQ ID NO 32
<211> LENGTH: 9
<212> TYPE: PRT
<213> ORGANISM: Homo sapiens

<400> SEQUENCE: 32

Phe Leu Trp Gly Pro Arg Ala Leu Val
1               5

<210> SEQ ID NO 33
<211> LENGTH: 21
<212> TYPE: DNA
<213> ORGANISM: Artificial sequence
<220> FEATURE:
<223> OTHER INFORMATION: Primer

<400> SEQUENCE: 33
gtcgacctgc agcccaagct t                                                   21

<210> SEQ ID NO 34
<211> LENGTH: 21
<212> TYPE: DNA
<213> ORGANISM: Artificial sequence
<220> FEATURE:
<223> OTHER INFORMATION: Primer

<400> SEQUENCE: 34
gcttatcatc gataagctta t                                                   21
```

```
<210> SEQ ID NO 35
<211> LENGTH: 21
<212> TYPE: DNA
<213> ORGANISM: Artificial sequence
<220> FEATURE:
<223> OTHER INFORMATION: Primer

<400> SEQUENCE: 35
tgtgagactc tgccaggatc c                                              21

<210> SEQ ID NO 36
<211> LENGTH: 21
<212> TYPE: DNA
<213> ORGANISM: Artificial sequence
<220> FEATURE:
<223> OTHER INFORMATION: Primer

<400> SEQUENCE: 36
cagaaagcta gcttgggatc c                                              21

<210> SEQ ID NO 37
<211> LENGTH: 32
<212> TYPE: DNA
<213> ORGANISM: Artificial sequence
<220> FEATURE:
<223> OTHER INFORMATION: Primer

<400> SEQUENCE: 37
ctgggaaatt attactgctt cctgtggggt cc                                  32

<210> SEQ ID NO 38
<211> LENGTH: 31
<212> TYPE: DNA
<213> ORGANISM: Artificial sequence
<220> FEATURE:
<223> OTHER INFORMATION: Primer

<400> SEQUENCE: 38
aagggccctc gttttcggtg gaggcaccaa g                                   31

<210> SEQ ID NO 39
<211> LENGTH: 32
<212> TYPE: DNA
<213> ORGANISM: Artificial sequence
<220> FEATURE:
<223> OTHER INFORMATION: Primer

<400> SEQUENCE: 39
caagcctcca tctcttgcac tcctccagcc ta                                  32

<210> SEQ ID NO 40
<211> LENGTH: 43
<212> TYPE: DNA
<213> ORGANISM: Artificial sequence
<220> FEATURE:
<223> OTHER INFORMATION: Primer

<400> SEQUENCE: 40
tagaccacca aatgccccta tcttatggta cctgcagaaa cca                      43

<210> SEQ ID NO 41
<211> LENGTH: 32
<212> TYPE: DNA
<213> ORGANISM: Artificial sequence
<220> FEATURE:
<223> OTHER INFORMATION: Primer
```

-continued

<400> SEQUENCE: 41
attggtagtg gtggtttcct gtggggtcca ag                               32

<210> SEQ ID NO 42
<211> LENGTH: 25
<212> TYPE: DNA
<213> ORGANISM: Artificial sequence
<220> FEATURE:
<223> OTHER INFORMATION: Primer

<400> SEQUENCE: 42
ggccctcgtt cgattcacca tttcc                                      25

<210> SEQ ID NO 43
<211> LENGTH: 32
<212> TYPE: DNA
<213> ORGANISM: Artificial sequence
<220> FEATURE:
<223> OTHER INFORMATION: Primer

<400> SEQUENCE: 43
atgtattact gtgcaagaac tcctccagcc ta                               32

<210> SEQ ID NO 44
<211> LENGTH: 43
<212> TYPE: DNA
<213> ORGANISM: Artificial sequence
<220> FEATURE:
<223> OTHER INFORMATION: Primer

<400> SEQUENCE: 44
tagaccacca aatgccccta tcttatgggg tcaaggaacc acg                   43

<210> SEQ ID NO 45
<211> LENGTH: 27
<212> TYPE: DNA
<213> ORGANISM: Artificial sequence
<220> FEATURE:
<223> OTHER INFORMATION: Primer

<400> SEQUENCE: 45
ttcctgtggg gtccaagggc cctcgtt                                    27

<210> SEQ ID NO 46
<211> LENGTH: 39
<212> TYPE: DNA
<213> ORGANISM: Artificial sequence
<220> FEATURE:
<223> OTHER INFORMATION: Primer

<400> SEQUENCE: 46
actcctccag cctatagacc accaaatgcc cctatctta                       39

<210> SEQ ID NO 47
<211> LENGTH: 16
<212> TYPE: PRT
<213> ORGANISM: Homo Sapiens

<400> SEQUENCE: 47

Tyr Phe Cys Ala Leu Trp Tyr Ser Asn Leu Trp Val Phe Gly Gly Gly
1               5                   10                  15

<210> SEQ ID NO 48
<211> LENGTH: 9
<212> TYPE: PRT
<213> ORGANISM: Homo sapiens

<400> SEQUENCE: 48

Phe Gln Gly Ser His Val Pro Trp Thr
1               5

<210> SEQ ID NO 49
<211> LENGTH: 9
<212> TYPE: PRT
<213> ORGANISM: Homo sapiens

<400> SEQUENCE: 49

Phe Leu Trp Gly Pro Arg Ala Leu Val
1               5

<210> SEQ ID NO 50
<211> LENGTH: 17
<212> TYPE: PRT
<213> ORGANISM: Homo sapiens

<400> SEQUENCE: 50

Tyr Ile Gly Ser Gly Gly Asp Arg Thr Tyr Tyr Pro Asp Thr Val Lys
1               5                   10                  15

Gly

<210> SEQ ID NO 51
<211> LENGTH: 12
<212> TYPE: PRT
<213> ORGANISM: Homo sapiens

<400> SEQUENCE: 51

His Tyr Gly His Tyr Val Asp Tyr Ala Val Asp Tyr
1               5                   10

<210> SEQ ID NO 52
<211> LENGTH: 13
<212> TYPE: PRT
<213> ORGANISM: Homo sapiens

<400> SEQUENCE: 52

Thr Pro Pro Ala Tyr Arg Pro Pro Asn Ala Pro Ile Leu
1               5                   10

<210> SEQ ID NO 53
<211> LENGTH: 16
<212> TYPE: PRT
<213> ORGANISM: Homo sapiens

<400> SEQUENCE: 53

Arg Ser Ser Gln Ser Ile Val His Ser Asn Gly Asn Thr Tyr Leu Glu
1               5                   10                  15

<210> SEQ ID NO 54
<211> LENGTH: 5
<212> TYPE: PRT
<213> ORGANISM: Homo ssapiens

<400> SEQUENCE: 54

Tyr Tyr Cys Ala Arg
1               5

<210> SEQ ID NO 55
<211> LENGTH: 5
<212> TYPE: PRT
<213> ORGANISM: Homo sapiens
<220> FEATURE:

```
<221> NAME/KEY: misc_feature
<222> LOCATION: (5)..(5)
<223> OTHER INFORMATION: Xaa is any amino acid

<400> SEQUENCE: 55

Tyr Tyr Cys Ala Xaa
1               5

<210> SEQ ID NO 56
<211> LENGTH: 4
<212> TYPE: PRT
<213> ORGANISM: Homo sapiens

<400> SEQUENCE: 56

Asp Tyr Trp Gly
1

<210> SEQ ID NO 57
<211> LENGTH: 4
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa is any amino acid

<400> SEQUENCE: 57

Xaa Tyr Trp Gly
1

<210> SEQ ID NO 58
<211> LENGTH: 17
<212> TYPE: PRT
<213> ORGANISM: Homo sapiens

<400> SEQUENCE: 58

Tyr Tyr Cys Ala Arg His Tyr Gly His Tyr Val Asp Tyr Ala Val Asp
1               5                   10                  15

Tyr

<210> SEQ ID NO 59
<211> LENGTH: 17
<212> TYPE: PRT
<213> ORGANISM: Homo sapiens

<400> SEQUENCE: 59

Tyr Phe Cys Ala Arg Asp Gly Tyr Tyr Glu Asn Tyr Tyr Ala Met Asp
1               5                   10                  15

Tyr

<210> SEQ ID NO 60
<211> LENGTH: 17
<212> TYPE: PRT
<213> ORGANISM: Homo sapiens

<400> SEQUENCE: 60

Tyr Phe Cys Ala Arg Ser Glu Tyr Tyr Gly Gly Ser Tyr Lys Phe Asp
1               5                   10                  15

Tyr

<210> SEQ ID NO 61
<211> LENGTH: 17
<212> TYPE: PRT
<213> ORGANISM: Homo sapiens
```

```
<400> SEQUENCE: 61

Tyr Tyr Cys Ala Arg Asp Pro Tyr Gly Gly Gly Lys Ser Glu Phe Asp
1               5                   10                  15

Tyr

<210> SEQ ID NO 62
<211> LENGTH: 17
<212> TYPE: PRT
<213> ORGANISM: Homo sapiens

<400> SEQUENCE: 62

Tyr Tyr Cys Ala Arg Asp Pro Asp Ile Leu Thr Ala Phe Ser Phe Asp
1               5                   10                  15

Tyr

<210> SEQ ID NO 63
<211> LENGTH: 17
<212> TYPE: PRT
<213> ORGANISM: Homo sapiens

<400> SEQUENCE: 63

Tyr Tyr Cys Thr Arg Gly Ala Tyr Arg Tyr Asp Tyr Ala Met Asp
1               5                   10                  15

Tyr

<210> SEQ ID NO 64
<211> LENGTH: 17
<212> TYPE: PRT
<213> ORGANISM: Homo sapiens

<400> SEQUENCE: 64

Tyr Tyr Cys Ala Lys Val Lys Phe Tyr Asp Pro Thr Ala Pro Asn Asp
1               5                   10                  15

Tyr

<210> SEQ ID NO 65
<211> LENGTH: 17
<212> TYPE: PRT
<213> ORGANISM: Homo sapiens

<400> SEQUENCE: 65

Tyr Tyr Cys Ala Lys Val Lys Phe Tyr Asp Pro Thr Ala Pro Asn Asp
1               5                   10                  15

Tyr

<210> SEQ ID NO 66
<211> LENGTH: 17
<212> TYPE: PRT
<213> ORGANISM: Homo sapiens

<400> SEQUENCE: 66

Tyr Tyr Cys Ala Arg Arg Glu Val Tyr Ser Tyr Tyr Ser Pro Leu Asp
1               5                   10                  15

Val

<210> SEQ ID NO 67
<211> LENGTH: 17
<212> TYPE: PRT
<213> ORGANISM: Homo sapiens

<400> SEQUENCE: 67
```

Tyr Tyr Cys Ala Arg Ala Pro Phe Tyr Gly Asn His Ala Met Asp
1               5                   10                  15

Tyr

<210> SEQ ID NO 68
<211> LENGTH: 17
<212> TYPE: PRT
<213> ORGANISM: Homo sapiens

<400> SEQUENCE: 68

Tyr Tyr Cys Ala Lys His Arg Val Ser Tyr Val Leu Thr Gly Phe Asp
1               5                   10                  15

Ser

<210> SEQ ID NO 69
<211> LENGTH: 17
<212> TYPE: PRT
<213> ORGANISM: Homo sapiens

<400> SEQUENCE: 69

Tyr Tyr Cys Ala Arg His Tyr Gly His Tyr Val Asp Tyr Ala Val Asp
1               5                   10                  15

Tyr

<210> SEQ ID NO 70
<211> LENGTH: 17
<212> TYPE: PRT
<213> ORGANISM: Homo sapiens

<400> SEQUENCE: 70

Tyr Tyr Cys Ala Arg Glu Val Tyr Ser Tyr Tyr Ser Pro Leu Asp
1               5                   10                  15

Val

<210> SEQ ID NO 71
<211> LENGTH: 17
<212> TYPE: PRT
<213> ORGANISM: Homo sapiens

<400> SEQUENCE: 71

Tyr Tyr Cys Val Thr Ser Leu Thr Trp Leu Leu Arg Arg Lys Arg Ser
1               5                   10                  15

Tyr

<210> SEQ ID NO 72
<211> LENGTH: 17
<212> TYPE: PRT
<213> ORGANISM: Homo sapiens

<400> SEQUENCE: 72

Tyr Tyr Cys Ala Lys Val Lys Phe Tyr Asp Pro Thr Ala Pro Asn Asp
1               5                   10                  15

Tyr

<210> SEQ ID NO 73
<211> LENGTH: 17
<212> TYPE: PRT
<213> ORGANISM: Homo sapiens

<400> SEQUENCE: 73

Tyr Tyr Cys Ala Arg Pro Pro His Asp Thr Ser Gly His Tyr Trp Asn
1               5                   10                  15

Tyr

<210> SEQ ID NO 74
<211> LENGTH: 17
<212> TYPE: PRT
<213> ORGANISM: Homo sapiens

<400> SEQUENCE: 74

Tyr Tyr Cys Gly Arg Ser Pro Ile Tyr Tyr Asp Tyr Ala Pro Phe Thr
1               5                   10                  15

Tyr

<210> SEQ ID NO 75
<211> LENGTH: 17
<212> TYPE: PRT
<213> ORGANISM: Homo sapiens

<400> SEQUENCE: 75

Tyr Phe Cys Ala Arg Asp Gly Tyr Tyr Glu Asn Tyr Tyr Ala Met Asp
1               5                   10                  15

Tyr

<210> SEQ ID NO 76
<211> LENGTH: 17
<212> TYPE: PRT
<213> ORGANISM: Homo sapiens

<400> SEQUENCE: 76

Tyr Tyr Cys Ala Arg Asp Pro Tyr Gly Gly Lys Ser Glu Phe Asp
1               5                   10                  15

Tyr

<210> SEQ ID NO 77
<211> LENGTH: 17
<212> TYPE: PRT
<213> ORGANISM: Homo sapiens

<400> SEQUENCE: 77

Tyr Tyr Cys Ala Lys His Arg Val Ser Tyr Val Leu Thr Gly Phe Asp
1               5                   10                  15

Ser

<210> SEQ ID NO 78
<211> LENGTH: 17
<212> TYPE: PRT
<213> ORGANISM: Homo sapiens

<400> SEQUENCE: 78

Tyr Tyr Cys Asn Ala Ile Ser Thr Thr Arg Asp Tyr Tyr Ala Leu Asp
1               5                   10                  15

Tyr

<210> SEQ ID NO 79
<211> LENGTH: 17
<212> TYPE: PRT
<213> ORGANISM: Homo sapiens

<400> SEQUENCE: 79

Tyr Tyr Cys Ala Arg Arg Ala Pro Phe Tyr Gly Asn His Ala Met Asp
1               5                   10                  15

Tyr

<210> SEQ ID NO 80
<211> LENGTH: 17
<212> TYPE: PRT
<213> ORGANISM: Homo sapiens

<400> SEQUENCE: 80

Tyr Tyr Cys Ser Ile Ile Tyr Phe Asp Tyr Ala Asp Phe Ile Met Asp
1               5                   10                  15

Tyr

<210> SEQ ID NO 81
<211> LENGTH: 17
<212> TYPE: PRT
<213> ORGANISM: Homo sapiens

<400> SEQUENCE: 81

Tyr Tyr Cys Ser Ile Ile Tyr Phe Asp Tyr Ala Asp Phe Ile Met Asp
1               5                   10                  15

Tyr

<210> SEQ ID NO 82
<211> LENGTH: 17
<212> TYPE: PRT
<213> ORGANISM: Homo sapiens

<400> SEQUENCE: 82

Tyr Tyr Cys Ala Arg Ser Arg Asp Tyr Tyr Gly Ser Ser Gly Phe Ala
1               5                   10                  15

Phe

<210> SEQ ID NO 83
<211> LENGTH: 17
<212> TYPE: PRT
<213> ORGANISM: Homo sapiens

<400> SEQUENCE: 83

Tyr Tyr Cys Ala Arg Pro Pro His Asp Thr Ser Gly His Tyr Trp Asn
1               5                   10                  15

Tyr

<210> SEQ ID NO 84
<211> LENGTH: 17
<212> TYPE: PRT
<213> ORGANISM: Homo sapiens

<400> SEQUENCE: 84

Tyr Tyr Cys Thr Arg Gly Ala Tyr Arg Tyr Asp Tyr Ala Met Asp
1               5                   10                  15

Tyr

<210> SEQ ID NO 85
<211> LENGTH: 17
<212> TYPE: PRT
<213> ORGANISM: Homo sapiens

<400> SEQUENCE: 85

Tyr Phe Cys Ala Arg Ser Glu Tyr Gly Gly Ser Tyr Lys Phe Asp
1               5                   10                  15

Tyr

<210> SEQ ID NO 86
<211> LENGTH: 17
<212> TYPE: PRT
<213> ORGANISM: Homo sapiens

<400> SEQUENCE: 86

Tyr Tyr Cys Ala Arg Asp Pro Asp Ile Leu Thr Ala Phe Ser Phe Asp
1               5                   10                  15

Tyr

<210> SEQ ID NO 87
<211> LENGTH: 17
<212> TYPE: PRT
<213> ORGANISM: Homo sapiens

<400> SEQUENCE: 87

Tyr Tyr Cys Ala Lys Val Lys Phe Tyr Asp Pro Thr Ala Pro Asn Asp
1               5                   10                  15

Tyr

<210> SEQ ID NO 88
<211> LENGTH: 24
<212> TYPE: PRT
<213> ORGANISM: Mus musculus

<400> SEQUENCE: 88

Tyr Tyr Cys Ser Ile Ile Tyr Phe Asp Tyr Ala Asp Phe Ile Met Asp
1               5                   10                  15

Tyr Trp Gly Gln Gly Thr Thr Val
            20

<210> SEQ ID NO 89

<400> SEQUENCE: 89

000

<210> SEQ ID NO 90
<211> LENGTH: 24
<212> TYPE: PRT
<213> ORGANISM: Homo sapiens

<400> SEQUENCE: 90

Tyr Tyr Cys Ala Arg His Tyr Gly His Tyr Val Asp Tyr Ala Val Asp
1               5                   10                  15

Tyr Trp Gly Gln Gly Thr Thr Val
            20

<210> SEQ ID NO 91
<211> LENGTH: 60
<212> TYPE: PRT
<213> ORGANISM: Mus musculus

<400> SEQUENCE: 91

Gln Val Gln Leu Gln Glu Ser Gly Gly Gly Leu Val Lys Ala Gly Gly
1               5                   10                  15

Ser Leu Lys Leu Ser Cys Ala Ala Ser Gly Phe Ala Phe Asn Thr Tyr
            20                  25                  30

Asp Met Ala Trp Val Arg Gln Thr Pro Glu Lys Arg Leu Glu Trp Val
        35                  40                  45

Ala Tyr Ile Gly Ser Gly Gly Asp Arg Thr Tyr Tyr
    50                  55                  60

<210> SEQ ID NO 92
<211> LENGTH: 60
<212> TYPE: PRT
<213> ORGANISM: Mus musculus

<400> SEQUENCE: 92

Glu Val Gln Leu Glu Glu Ser Gly Gly Gly Leu Val Thr Pro Gly Gly
1               5                   10                  15

Ser Leu Arg Leu Ser Cys Ala Ala Ser Gly Tyr Val Phe Ser Thr Tyr
            20                  25                  30

Asp Met Ser Trp Val Arg Gln Thr Pro Glu Lys Arg Leu Glu Trp Val
        35                  40                  45

Ala Phe Ile Ser Ser Gly Gly Gly Arg Thr Ser Tyr
    50                  55                  60

<210> SEQ ID NO 93
<211> LENGTH: 38
<212> TYPE: PRT
<213> ORGANISM: Mus musculus

<400> SEQUENCE: 93

Pro Asp Thr Val Lys Gly Arg Phe Thr Ile Ser Arg Asp Asn Gly Lys
1               5                   10                  15

Asn Thr Leu Tyr Leu Gln Leu Asn Ser Leu Lys Ser Glu Asp Thr Ala
            20                  25                  30

Met Tyr Tyr Cys Ala Arg
        35

<210> SEQ ID NO 94
<211> LENGTH: 38
<212> TYPE: PRT
<213> ORGANISM: Mus musculus

<400> SEQUENCE: 94

Pro Asp Thr Val Lys Gly Arg Phe Thr Ile Ser Arg Asp Asp Ala Lys
1               5                   10                  15

Asn Thr Leu Tyr Leu Gln Met Ser Ser Leu Gln Ser Glu Asp Thr Ala
            20                  25                  30

Met Tyr Tyr Cys Thr Arg
        35

<210> SEQ ID NO 95
<211> LENGTH: 60
<212> TYPE: PRT
<213> ORGANISM: Mus musculus

<400> SEQUENCE: 95

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe
    50                  55                  60

<210> SEQ ID NO 96
<211> LENGTH: 60
<212> TYPE: PRT
<213> ORGANISM: Mus musculus

```
<400> SEQUENCE: 96

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Gly
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Ile Ser Asn Arg Phe
    50                  55                  60

<210> SEQ ID NO 97
<211> LENGTH: 49
<212> TYPE: PRT
<213> ORGANISM: Homo sapiens

<400> SEQUENCE: 97

Ser Gly Val Pro Asp Arg Phe Ser Gly Ser Gly Ser Gly Thr Asp Phe
1               5                   10                  15

Thr Leu Lys Ile Ser Arg Val Glu Ala Glu Asp Leu Gly Ile Tyr Tyr
            20                  25                  30

Cys Phe Gln Gly Ser His Val Pro Trp Thr Phe Gly Gly Gly Thr Lys
            35                  40                  45

Leu

<210> SEQ ID NO 98
<211> LENGTH: 49
<212> TYPE: PRT
<213> ORGANISM: Mus musculus

<400> SEQUENCE: 98

Ser Gly Val Pro Asp Arg Phe Ser Gly Ser Gly Ser Gly Thr Asp Phe
1               5                   10                  15

Thr Leu Lys Ile Ser Arg Val Glu Ala Glu Asp Leu Gly Val Tyr Tyr
            20                  25                  30

Cys Phe Gln Gly Ser His Val Pro Tyr Thr Phe Gly Gly Gly Thr Lys
            35                  40                  45

Leu

<210> SEQ ID NO 99
<211> LENGTH: 12
<212> TYPE: PRT
<213> ORGANISM: Homo sapiens

<400> SEQUENCE: 99

Thr Pro Pro Ala Tyr Pro Pro Asn Ala Pro Ile Leu
1               5                   10

<210> SEQ ID NO 100
<211> LENGTH: 13
<212> TYPE: PRT
<213> ORGANISM: Homo sapiens

<400> SEQUENCE: 100

Thr Pro Pro Ala Tyr Arg Pro Asn Asn Ala Pro Ile Leu
1               5                   10
```

POLYPEPTIDES CAPABLE OF BINDING TO CD64 COMPRISING ONE OR MORE HETEROLOGOUS T CELL EPITOPES AND THEIR USES

The present invention relates to T cell epitopes, and in particular to molecules for delivering such epitopes so as to raise a cytotoxic T cell (CTL) response. In the present invention, the molecules may be modified antibodies, especially human monoclonal IgG1 antibodies which bind to CD64 receptor and which are engineered to express T cell epitopes within their CDR regions to stimulate both helper and cytotoxic T cell responses.

Antibodies are composed of constant regions (Fc) that determine the effector function of the antibody and the antigen binding domains (Fab) which comprise a unique set of complementarity determining regions (CDRs). The role of antibodies is to bind to antigens, thereby making them more visible to the immune system. Antigen-antibody (Ag-Ab) complexes can bind to Fc receptor on phagocytic cells to allow efficient digestion of harmful pathogens. Fc receptor internalisation also allows efficient antigen presentation to stimulate T cell responses. Previous studies have shown that Fc receptor internalisation of Ag-Ab complexes is 1,000 fold more efficient than pinocytosis for stimulation of helper T cell responses. More recently, it has been shown that Fc receptor internalisation of antigen-antibody complexes by dendritic cells also allows more efficient processing of antigen into class I and class II presentation pathways to allow stimulation of not only helper but also cytotoxic T cell responses (Regnault et al., (1999) *J exp Med.* 189: 371-380). Furthermore, Fc receptor internalisation activates dendritic cells to express co-stimulatory molecules essential for priming naïve responses. Fc receptor internalisation is a consequence of receptor cross linking by antigen/antibody complexes and previous studies have shown that Ab alone cannot mediate this effect.

Although several studies have suggested that anti-idiotype antibodies mimicking antigens can stimulate cytotoxic T cell responses, they have failed to demonstrate antigen-specific cytotoxic T cell responses stimulated by specific class I MHC presentation. Indeed, in a study whereby a helper and a cytotoxic T cell epitope were transplanted into the CDR region of a mouse antibody, only helper responses could be stimulated.

For example, WO 96/19584 discloses chimeric antibodies in which T cell epitopes are inserted into the CDRs of an antibody, and alleges that such chimeric antibodies are suitable for raising a CTL response. However, this document only discloses that a CTL can be induced by nucleic acid encoding such a chimeric antibody but does not disclose how a CTL response can be induced by the application of chimeric antibody itself. Thus, it is stated at page 51, lines 8-10 that “only proteins synthesised by the target cells themselves are presented by MHC class I molecules and recognised by CTLs”.

In addition, WO 00/64488 discloses that a CTL response can be raised by nucleic acid encoding a chimeric antibody having heterologous T cell epitopes inserted in the CDRs thereof, provided that the nucleic acid is directed for expression in haematopoietic cells.

Surprisingly, the present inventors have found that certain human monoclonal antibodies which have distinct T cell epitopes within their CDR regions can stimulate both helper and antigen specific T cell responses. Furthermore, they have shown that human FcγI region is essential for the generation of the cytotoxic responses and greatly increases the sensitivity of stimulating helper T cell responses. This region binds CD64 of dendritic cells. Accordingly, it can be used to deliver T cell epitopes to dendritic cells which can process them and present them to T cells, thereby stimulating cytotoxic and/or helper T cell responses.

Thus, in a first aspect, the present invention provides the use of a polypeptide which comprises (i) a first portion comprising the part of human Fc which binds to CD64, and (ii) a second portion comprising one or more heterologous T cell epitopes in the manufacture of a medicament for stimulating a cytotoxic T cell response.

The first portion may comprise the Fc segment of IgG, for example IgG1. The first portion may comprise the heavy chain (γ) region of the Fc segment. Preferably, the first portion comprises the heavy chain (γ) region of the Fc segment of IgG1 (FcγI).

“Heterologous T cell epitope” is intended to mean a T cell epitope which is heterologous to the first portion. For example, where the second portion comprises the Fab fragment of an antibody, a heterologous T cell epitope is one which was not previously present in the Fab fragment.

The second portion may be a polypeptide. Alternatively, the second portion may be a Fab fragment, which may be from human or non-human, preferably, mouse. It is preferred if the, or each, T cell epitope is/are inserted to replace the CDRs, although this is not necessary, provided that the T cell epitopes are delivered to and presented by antigen presenting cells. The heterologous T cell epitope may be inserted as a whole, although it may made up from an inserted amino acid sequence, together with flanking amino acids of the second portion. Alternatively, for example, an anti-idiotypic antibody may be raised in one species, e.g. mouse, in respect of a particular antigen, and the Fab fragment of that antibody grafted to the part of human Fc which binds to CD64.

In the prior art, it has been shown that FcγI can be used to direct molecules to dendritic cells (Liu et al, (1999) *J. Clin Invest* 98(9): 2001-2007). However, these studies were not able to show that such molecules could not stimulate a CTL response, in spite of earlier speculation that this might be possible (Guyre, et al, (1997) *Cancer Immunol. Immunothr.* 45: 146-148).

As used herein, the term “polypeptide” means, in general terms, a plurality of amino acid residues joined together by peptide bonds. It is used interchangeably and means the same as peptide, protein, oligopeptide, or oligomer. The term “polypeptide” is also intended to include fragments, analogues and derivatives of a polypeptide wherein the fragment, analogue or derivative retains essentially the same biological activity or function as a reference protein.

Preferably, the polypeptide useful in the invention is a protein domain Fc construct or a monoclonal antibody. Polypeptides useful in the present invention may be referred to herein as “Immunobodies”.

The invention provides nucleic acid encoding the polypeptide of the first aspect of the invention. The nucleic acid may be DNA, cDNA, or RNA such as mRNA obtained by cloning or produced by chemical synthesis. For therapeutic use, the nucleic acid is preferably in a form capable of being expressed in the subject to be treated.

The polypeptide useful in the present invention or the nucleic acid of the present invention may be provided as an isolate, in isolated and/or purified form, or free or substantially free of material with which it is naturally associated. In the case of a nucleic acid, it may be free or substantially free of nucleic acid flanking the gene in the human genome, except possibly one or more regulatory sequence(s) for expression. Nucleic acid may be wholly or partially synthetic and may include genomic DNA, cDNA or RNA. Where nucleic acid according to the invention includes RNA, reference to the sequence shown should be construed as reference to the RNA equivalent, with U substituted for T.

Nucleic acid sequences encoding a polypeptide useful in the present invention can be readily prepared by the skilled person, for example using the information and references contained herein and techniques known in the art (for example, see Sambrook, Fritsch and Maniatis, "Molecular Cloning", A Laboratory Manual, Cold Spring Harbor Laboratory Press, 1989, and Ausubel et al, Short Protocols in Molecular Biology, John Wiley and Sons, 1992), given the nucleic acid sequences and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding the polypeptide may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially-available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

In order to obtain expression of the nucleic acid sequences, the sequences can be incorporated into a vector having one or more control sequences operably linked to the nucleic acid to control its expression. The vectors may include other sequences such as promoters or enhancers to drive the expression of the inserted nucleic acid, nucleic acid sequences so that the polypeptide is produced as a fusion and/or nucleic acid encoding secretion signals so that the polypeptide produced in the host cell is secreted from the cell. Polypeptide can then be obtained by transforming the vectors into host cells in which the vector is functional, culturing the host cells so that the polypeptide is produced and recovering the polypeptide from the host cells or the surrounding medium. Prokaryotic and eukaryotic cells are used for this purpose in the art, including strains of *E. coli*, yeast, and eukaryotic cells such as insect cells, and animal cells, for example, COS, CHO cells, Bowes Melanoma and other suitable human cells.

Preferably, the part of the human Fc of the first portion binds to CD64 of dendritic cells. Thus, a further aspect of the invention provides dendritic cells which present, express or are bound to the heterologous T cell epitopes of the second portion.

In a second aspect, the invention provides a method for stimulating a cytotoxic T cell response in a patient such as a mammal, including human, comprising administering to a recipient a therapeutically effective amount of a polypeptide which comprises (i) a first portion comprising the part of human Fc which binds to CD64, and (ii) a second portion comprising one or more heterologous T cell epitopes. The invention further provides a method for stimulating a cytotoxic T cell response in a patient such as a mammal, including human, comprising administering to a recipient a therapeutically effective amount of a nucleic acid encoding a polypeptide which comprises (i) a first portion comprising the part of human Fc which binds to CD64, and (ii) a second portion comprising one or more heterologous T cell epitopes. Preferably, the polypeptide and the nucleic acid are administered as a combination therapy. In such a method, the polypeptide or nucleic acid may be administered intravenously, intradermally, intramuscularly, orally or by other routes.

Intradermal or intramuscular administration is preferred because these tissues contain dendritic cells and they do not have high levels of serum IgG that may act as a competitive inhibitor for binding to CD64.

As used herein, the term "treatment" includes any regime that can benefit a human or non-human animal. The treatment may be of an inherited or acquired disease. Preferably, the treatment is of a condition/disorder associated with cell proliferation such as cancer.

The polypeptide or nucleic acid may be employed in combination with a pharmaceutically acceptable carrier or carriers. Such carriers may include, but are not limited to, saline, buffered saline, dextrose, liposomes, water, glycerol, ethanol and combinations thereof.

Adjuvants may be employed to facilitate stimulation of the host's immune response, and may include, aluminium hydroxide, lysolecithin, pluronic, polyols, polyanions, peptides, proteins and oil emulsions.

In one embodiment, the present invention relates to raising an anti-idiotypic antibody in one species, e.g. mouse, in respect of a particular antigen, grafting the Fab fragment of that antibody, or a polypeptide fragment, (which may be at least 300 amino acids in length, or even at least 10-20 amino acids long, for example, 16 amino acids (corresponding to the size of a class II epitope) or 9 amino acids (corresponding to the size of a class I epitope) in length) to the part of human Fc which binds to CD64 (e.g. human FcγI), and using the resulting polypeptide to raise a cytotoxic T cell response against that antigen.

In certain other embodiments, the present invention relates to a method of engineering T cell epitopes from target antigens into any of the CDR regions of human monoclonal IgG1 antibodies, and the use of such engineered antibodies as vaccines to stimulate both helper and cytotoxic T cell responses.

Any T cell epitope can be inserted, provided that the antibody can bind to CD64 and stimulate a cytotoxic T cell response. T cell epitopes from pathogens such as HIV, Hepatitis C and other infections that require CTLs to clear latent infections may be used, although it is preferred if the epitope is a "self-epitope", i.e. associated with a condition/disorder associated with cell proliferation such as cancer. Preferably, the T cell epitope is such that the antibody can fold correctly and be secreted. It is therefore preferred if the inserted epitopes are of similar size and amino acid composition to the original CDRs. The second portion may have a plurality of different T cell epitopes so as to generate a wide variety of T cell vaccines. The second portion may incorporate multiple epitopes from a single antigen, thereby ensuring that the majority of individuals with different HLA types respond to the single vaccine. Alternatively, multiple T cell epitopes from multiple antigens targeting a restricted spectrum of HLA types could be inserted. The molecules may include a variety of antigens from a single pathogen or cancer type or they could include disperate antigens targeting a wide range of solid tumours or pathogens. The molecules may even be designed to target different cell populations within a tumour, such as tumour epithelial and endothelial antigens.

A preferred polypeptide useful in the present invention is a human IgG1 monoclonal antibody engineered to express within its CDR regions cytotoxic T cell epitopes, optionally with helper T cell epitopes. The human monoclonal antibodies useful in the invention may be prepared by immortalising nucleic acid sequences that encode antibodies. The immortalisation process may be carried out by hybridoma fusion techniques, by viral transformation of human antibody-producing lymphocytes, by techniques that combine cell fusion and viral transformation methodologies, or by any other technique known to the skilled person.

In one embodiment, the polypeptide useful in the present invention, is prepared using a combination of Epstein-Barr virus (EBV) transformation and hybridoma fusion techniques, such as those described by Kozbor et al., *Proc. Natl. Acad. Sci.* (1982) 79:6551. For instance, the hybridomas may be created by fusing stimulated B cells, obtained from a human, with a mouse/human heterohybrid fusion partner. A variety of such fusion partners have been described. See, for example, James & Bell, *J. Immunol. Methds*. (1987) 100:5-04 and U.S. Pat. No. 4,624,921. A mouse/human fusion partner may be constructed by fusing human lymphocytes stimulated or transformed by EBV with readily-available mouse myeloma lines such as NS-1 or P3NS-1, in the presence of polyethylene glycol, for instance. The hybrid could be suitably drug-marked, which may be accomplished by cultivation of the hybrid in increasing concentrations of the desired drug, such as 6-thiogua-nine, ouabain, or neomycin.

Alternatively, the immortalisation of cells producing the human anti-idiotype antibodies of interest may be accomplished using EBV transformation techniques. For example, B-lymphocytes derived from peripheral blood, bone marrow, lymph nodes, tonsils, etc. of patients immunised with the idiotype antibody are immortalised using EBV according to methods such as those described in U.S. Pat. No. 4,464,465 and Chan et al., *J. Immunol*. (1986) 136:106.

The hybridomas or lymphobastoid cells which secrete the antibody of interest may be identified by screening culture supernatants for human IgG1 production. Cells from wells possessing the desired activity may be cloned and subcloned in accordance with conventional techniques, and monitored until stable immortalised lines producing the human monoclonal antibody of interest are identified. By "monoclonal antibody" is meant an antibody produced by a clonal, continuous cell line separate from cells which produce monoclonal antibodies of a different specificity. Thus, such antibodies are produced isolated from other antibodies and, accordingly, in substantially pure form at a concentration greater than normally occurring in human serum.

The immortalised cell lines of the present invention may also be fused with other cells to produce hybridomas or heterohybridomas, and thus provide for the transfer of genes encoding the human monoclonal antibodies. Alternatively, recombinant DNA techniques may be used to isolate and transfer the DNA encoding the immunoglobulins or regions thereof to a variety of hosts for specific antibody production.

The invention further includes a modified antibody having the constant region of a human antibody, and the variable or hypervariable region of a mouse monoclonal antibody into which heterologoous T cell epitopes have been inserted, and its use in raising a CTL response. The variable region other than the hypervariable region may also be derived from the variable region of a human antibody. Such an antibody is said to be humanised. Methods for making humanised antibodies are known in the art. Methods are described, for example, in Winter, U.S. Pat. No. 5,225,539.

The variable region of the antibody outside of the mouse hypervariable region may also be derived from a mouse monoclonal antibody. In such case, the entire variable region is derived from murine monoclonal antibody and the antibody is said to be chimerised. Methods for making chimerised antibodies are known in the art. Such methods include, for example, those described in U.S. patents by Boss (Celltech) and by Cabilly (Genentech). See also U.S. Pat. Nos. 4,816, 397 and 4,816,567, respectively.

The invention includes the use of modified human monoclonal antibodies having the constant region of a human IgG1 antibody but replacement of one or more of the hypervariable regions with T cell epitopes for inducing a CTL response.

A modified antibody of the present invention can have one, two, three, four, five or all of its hypervariable regions replaced with T cell epitopes. Preferably the incorporated T cell epitopes are of similar size and charge to the amino acids of the original CDR of the antibody so that the antibody folds and is secreted correctly. T cell epitopes can be predicted using known T cell algorithms or synthesised as peptides and screened using standard T cell assays. The identified T cell epitopes may be cytotoxic T cell epitopes and/or helper T cell epitopes, and may have a preferred amino acid length 9-20 amino acids. These epitopes are preferably carefully matched to the closest CDR of a human monoclonal antibody and the sequences modified using site directed mutagenesis of the encoding DNA. Each CDR is preferably replaced sequentially and the ability of the immunobody to fold and be secreted as an intact immunoglobulin molecule screened. The ability of the immunobody to stimulate helper and cytotoxic T cell responses can be screened as exemplified herein. The invention further includes a modified antibody having the constant region of a human antibody fused to a whole or domain of a protein into which heterologous T cell epitopes have been inserted, and its use in raising a CTL response.

Polypeptides useful in the present invention can incorporate multiple T cell epitopes from a single target antigen that can bind to the majority of both class I and class II MHC molecules. This may create a vaccine that can be used in widespread population vaccination. Alternatively polypeptides useful in the invention can incorporate multiple T cell epitopes from multiple target antigens that can bind to the most common class I and class II phenotypes. This may create a vaccine that may prevent selection of antigen loss variants. Target antigens may be from a single pathogen or tumour type or may be selected to give an immune response against a variety of pathogens or cancers.

Polypeptides useful in the present invention targeting specific common HLA phenotypes may incorporate numerous T cell epitopes from a wide variety of cancers and/or pathogens, providing a single vaccine to prevent disease.

Thus, the present invention also encompasses a method of making a polypeptide of the first aspect, the method including expression from nucleic acid encoding the polypeptide (generally nucleic acid according to the invention). This may conveniently be achieved by growing a host cell in culture, containing such a vector, under appropriate conditions which cause or allow expression of the polypeptide. Polypeptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manuel: $2^{nd}$ edition, Sambrook et al., 1989, Cold Spring Harbor Laboratory Press. Many techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley and Sons, 1992.

Thus, a further aspect of the present invention provides a host cell containing heterologous nucleic acid as disclosed herein.

The nucleic acid of the invention may be integrated into the genome (e.g. chromosome) of the host cell. Integration may be promoted by inclusion of sequences which promote recombination with the genome in accordance with standard techniques. The nucleic acid may be on an extra-chromosomal vector within the cell, or otherwise identifiably heterologous or foreign to the cell.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide (or peptide) is produced. If the polypeptide is expressed coupled to an appropriate signal leader peptide it may be secreted from the cell into the culture medium. Following production by expression, a polypeptide or peptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

The polypeptides useful in the invention can be formulated in pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. intradermal, oral, intravenous, cutaneous or subcutaneous, nasal, intramuscular, intraperitoneal routes. The formulation is preferably liquid, and is ordinarily a physiologic salt solution containing non-phosphate buffer at pH 6.8-7.6, or may be lyophilised powder.

The compositions comprising or for the delivery of polypeptides are preferably administered to an individual in a "therapeutically effective amount", this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. The polypeptides of the invention are particularly relevant to the treatment of existing cancer and in the prevention of the recurrence of cancer after initial treatment or surgery. Examples of the techniques and protocols mentioned above can be found in Remington's Pharmaceutical Sciences, 16$^{th}$ edition, Oslo, A. (ed), 1980.

Preferably, the polypeptides of the invention stimulate helper and cytotoxic T cells that can significantly inhibit the growth of tumour cells when administered to a human in an effective amount. The optimal dose can be determined by physicians based on a number of parameters including, for example, age, sex, weight, severity of the condition being treated, the active ingredient being administered and the route of administration. For example, a dose of 10-100 µg of polypeptides is sufficient to stimulate both helper and cytotoxic T cell responses.

The polypeptides of the invention may be administered along with additional pharmaceutically acceptable ingredients. Such ingredients include, for example, immune system stimulators.

A composition may be administered alone or in combination with other treatments, either simultaneously or sequentially dependent upon the condition to be treated. Other cancer treatments include other monoclonal antibodies, other chemotherapeutic agents, other radiotherapy techniques or other immuno therapy known in the art. One particular application of the compositions of the invention are as an adjunct to surgery, i.e. to help to reduce the risk of cancer reoccurring after a tumour is removed.

Injections (im) may be the primary route for therapeutic administration of the polypeptides of this invention. Liquid formulations may be utilised after reconstitution from powder formulations.

The polypeptides may be administered in a localised manner to a tumour site or other desired site or may be delivered in a manner in which it targets tumour or other cells.

The dose of polypeptide will be dependent upon the properties of the agent employed, e.g. its binding activity and in vivo plasma half-life, the concentration of the polypeptide in the formulation, the administration route, the site and rate of dosage, the clinical tolerance of the patient involved, the pathological condition afflicting the patient and the like, as is well within the skill of the physician. For example, doses of 100 µg of polypeptide per patient per administration are preferred, although dosages may range from about 10 µg to 1 mg per dose. Different dosages are utilised during a series of sequential inoculations; the practitioner may administer an initial inoculation and then boost with relatively smaller doses of antibody.

The polypeptide compositions of the invention can be administered in a variety of ways and to different classes of recipients. Examples of types of cancer that can be treated with the antibody include colorectal cancer, lung, breast, gastric and ovarian cancers.

This invention is also directed to optimise immunisation schedules for enhancing a protective immune response against cancer. In this respect, the invention provides nucleic acid, encoding a polypeptide which comprises (i) a first portion comprising the part of human Fc which binds to CD64 and (ii) a second portion comprising one or more heterologous T cell epitopes, which is administered in combination with an isolated or recombinant polypeptide comprising (i) a first portion comprising the part of human Fc which binds to CD64 and (ii) a second portion comprising one or more heterologous T cell epitopes. The administration of the nucleic acid and isolated or recombinant polypeptide may take place either simultaneously or sequentially dependent upon the condition to be treated. The nucleic acid may be formulated as a DNA vaccine such as described herein.

Preferred features of each aspect of the invention are as for each of the other aspects mutatis mutandis. The prior art documents mentioned herein are incorporated to the fullest extent permitted by law.

Figure 2:
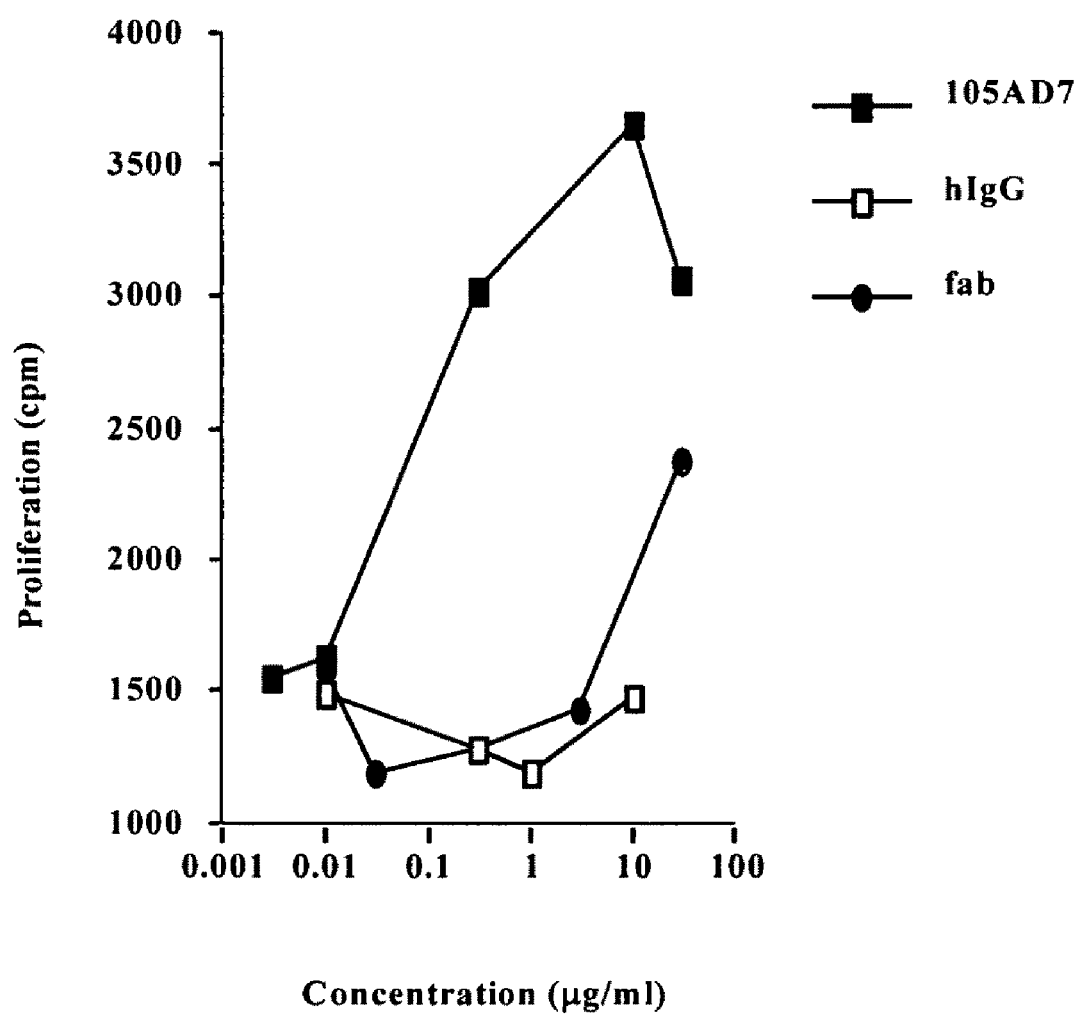

The invention will now be described further in the following non-limiting examples. Reference is made to the following drawings:

FIG. 1—Human monoclonal antibody stimulating helper T cell proliferation in donors expressing HLA-DR, 1, 3, 7, 11 and 15 haplotypes FIG. 2—Human monoclonal antibody stimulating helper T cell proliferation responses (v). Results show that removing the Fc to form a Fab fragment significantly reduced the sensitivity of T cells to proliferate (λ). No response was seen to hIgG that does not express a T cell epitope (i).

Figure 3:
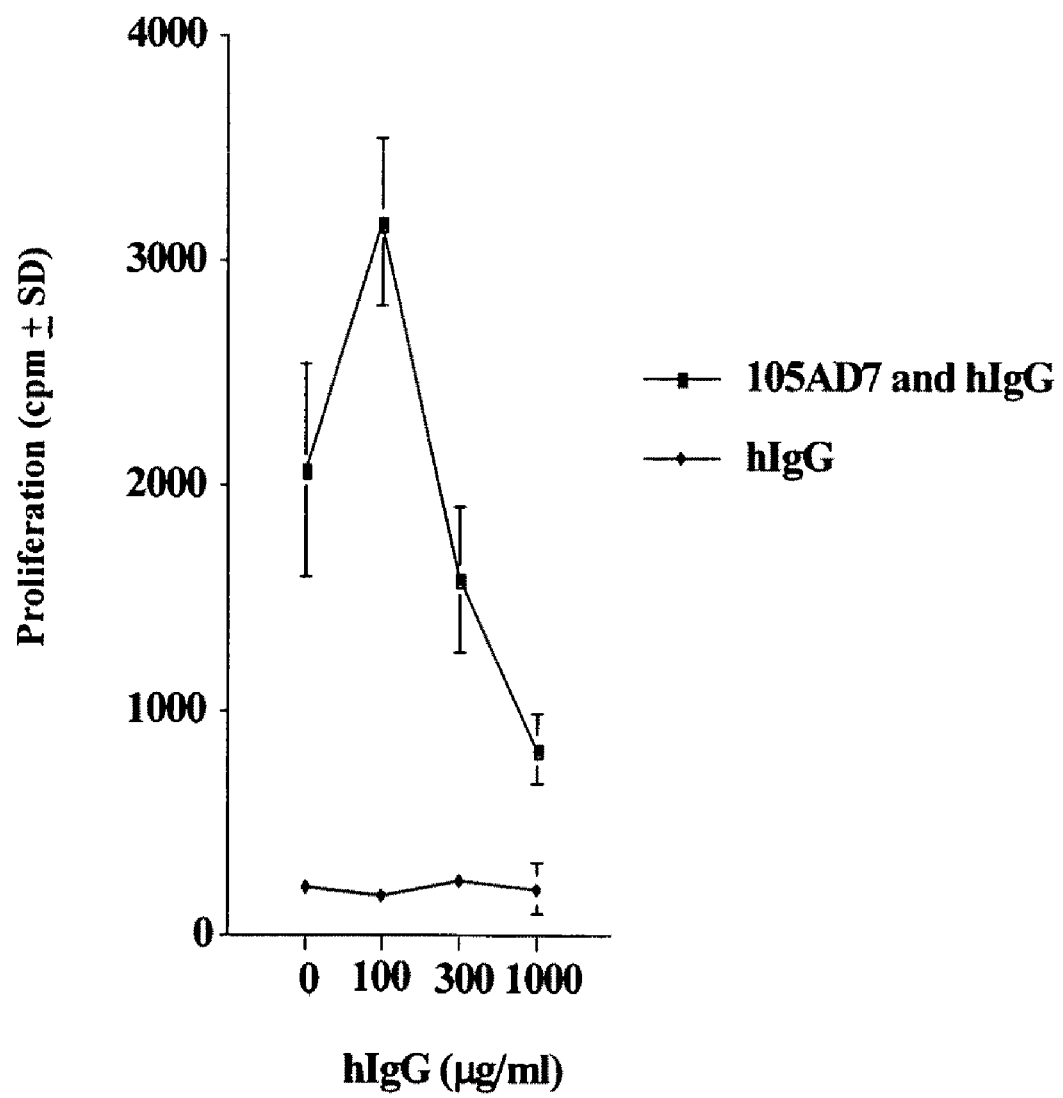

FIG. 3—A human monoclonal IgGl antibody stimulates helper T cell proliferation responses that are inhibited by an excess of hIgG that competes for Fc binding.

Figure 4:
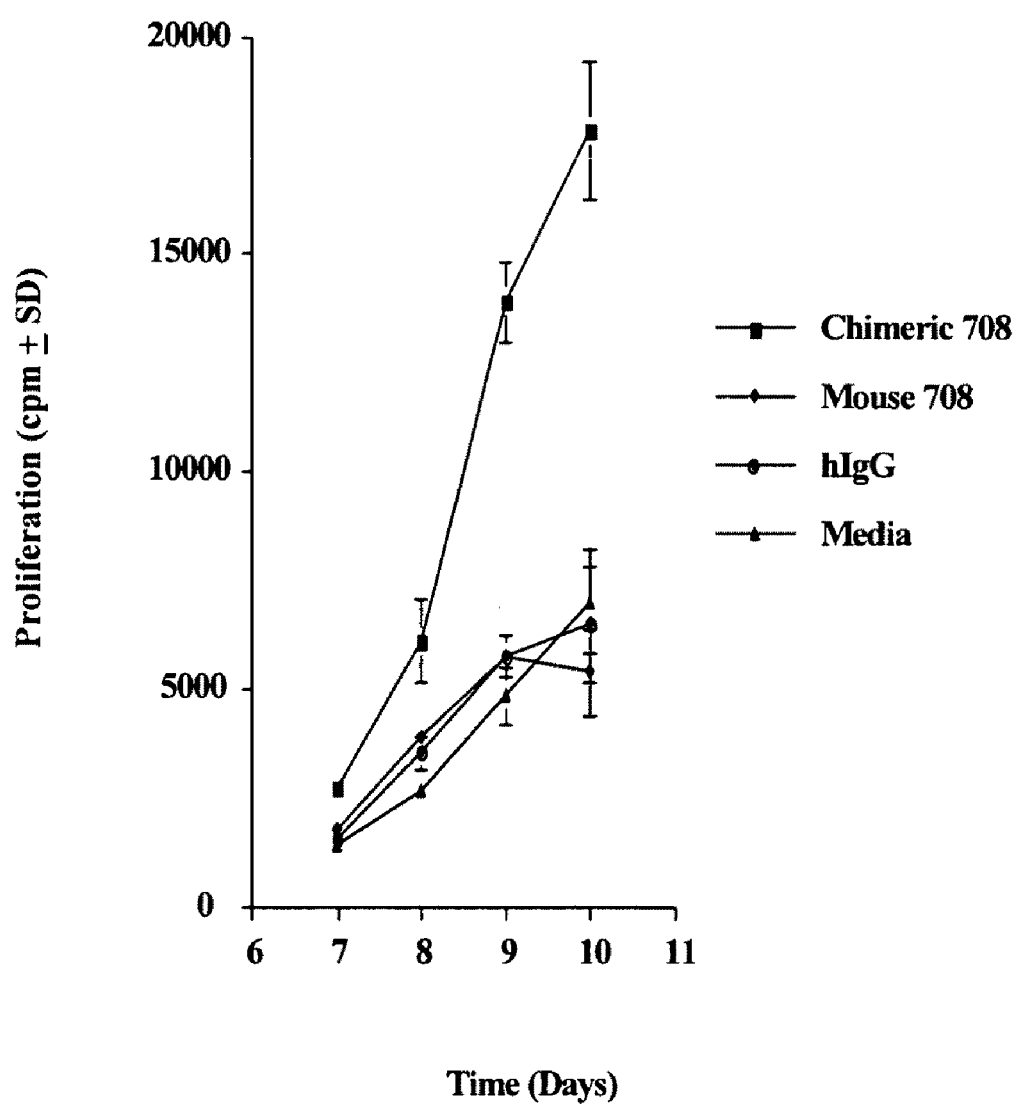

FIG. 4—Chimeric hIgGl 708 antibody but not mouse (υ) or human IgG (λ) or medium alone stimulated proliferation of lymphocytes from naïve donors.

Figure 5A:
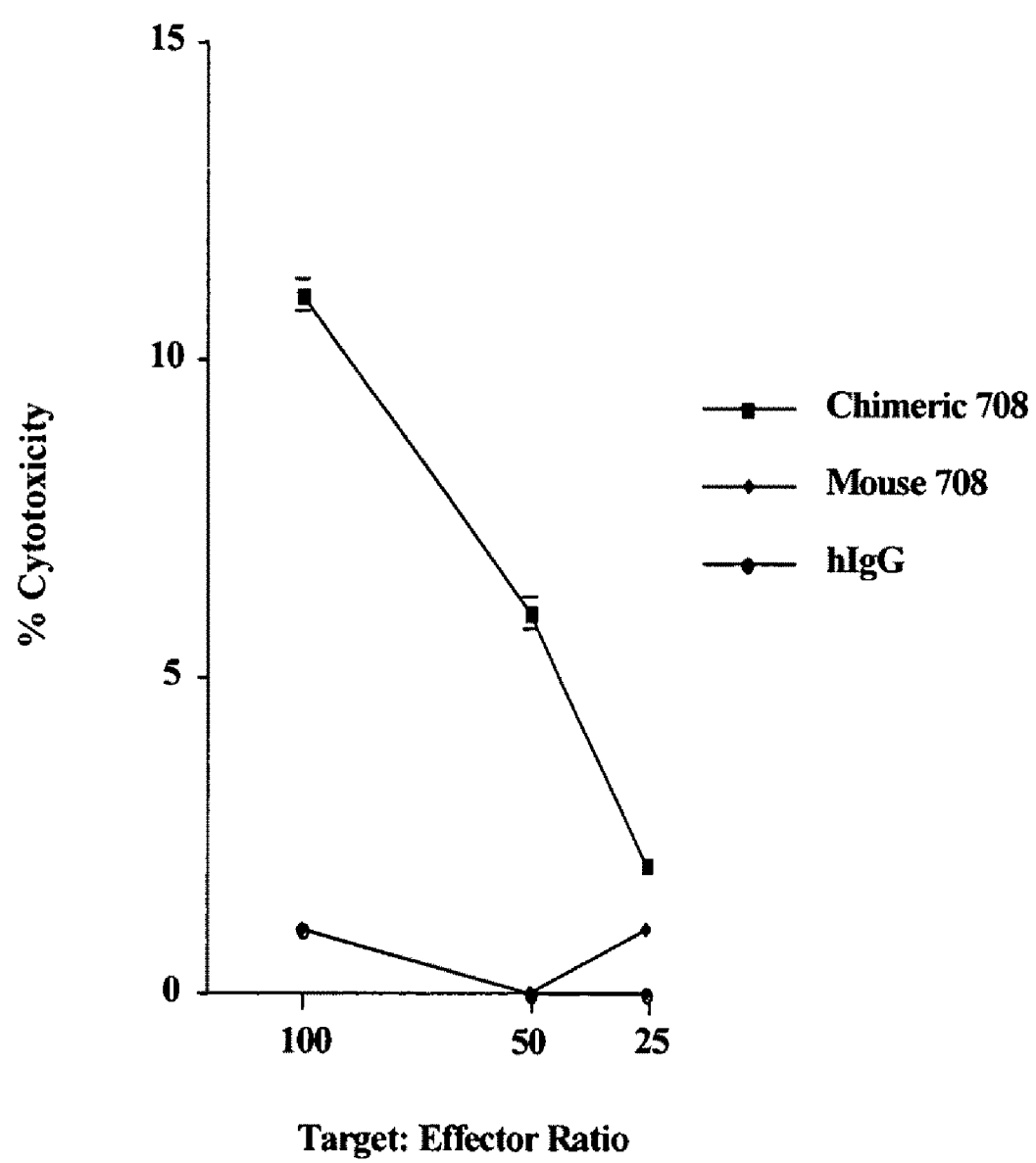
Figure 5B:
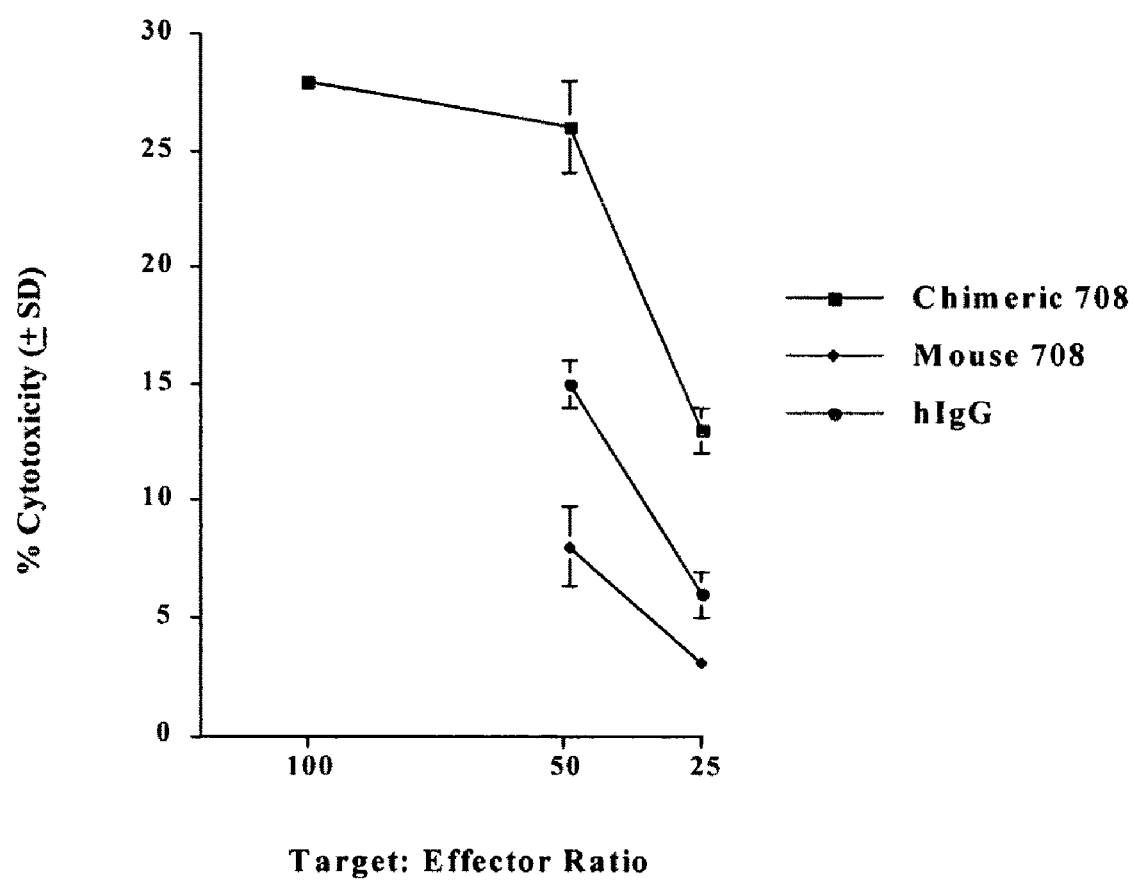

FIG. 5—Chimeric human IgG1 708 (v) antibody but not mouse 708 (υ) or hIgG (λ) induced redirected killing by human CD8 T cells of a mouse cell line P815 coated with OKT3 antibody. Cytotoxicity was assessed by chromium release at different effector target ratios.

Figure 6:
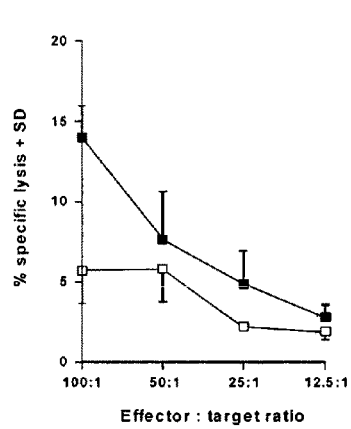
Figure 6:
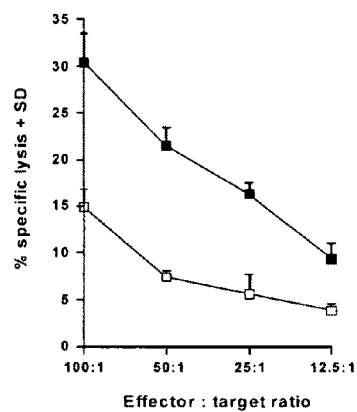
Figure 6:
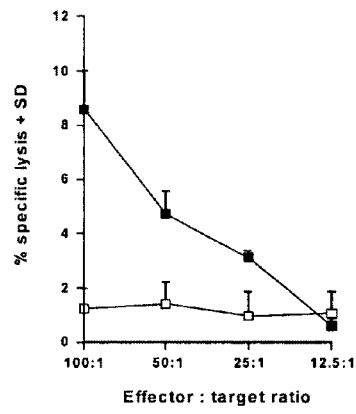
Figure 6:
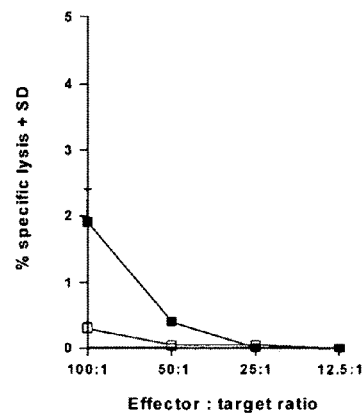

FIG. 6—Mice immunised with a 105AD7 DNA vaccine induced CTL responses that recognise target cells pulsed with CDRH3 peptide.

Figure 7:
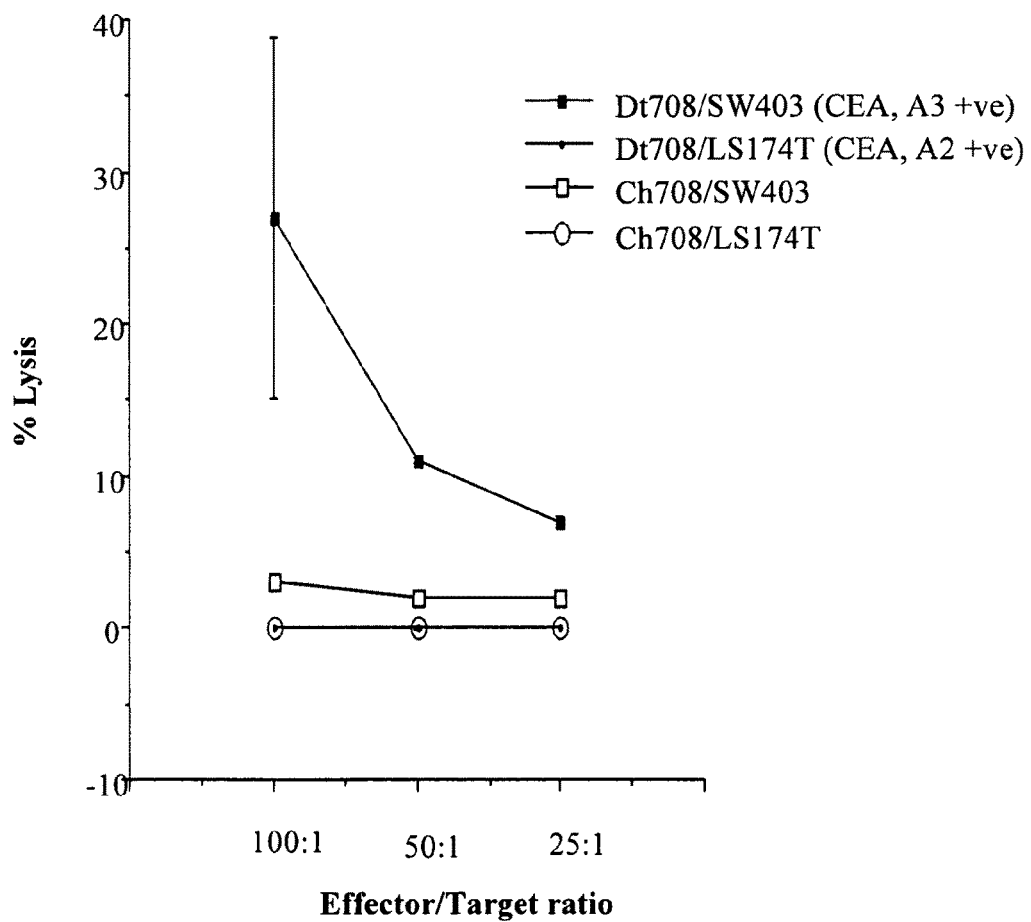

FIG. 7—HLA matched human IgGl 708 can stimulate cytotoxic T cells that recognise tumour cells expressing CEA antigen. These results show 708 mimics a T cell epitope processed and presented from CEA antigens which are expressed by target cells.

FIG. 8—Cytotoxic T Cell Assay following DNA Prime/Protein Boost (open symbols refer to target cells pulsed with irrelevant peptide; closed symbols refer to mice pulsed with H-2Kd peptide).

FIGS. 9a and 9b: a. Antibody Heavy Chain Expression Vector Antibody b. Light Chain Expression Vector.

FIGS. 10a and 10b: a. Effect of C-terminal amino acid insertions. FLWGPRALV (SEQ ID NO:32) in SC100 CDRs b. Effect of C-terminal amino acid insertions. Percentage change from native, FLWGPRALV (SEQ ID NO:32) in SC100 CDRs.

FIG. 11. Effects of C-Terminal Amino Acid Substitutions on the NetChop Y Value of Tyrosine (TPPAYPPNAPIL) (SEQ ID NO:99); T Helper Epitope in SC100 CDR-L1.

FIG. 12. Molecular Model of the Fv Region of the Antibody SC100.

FIG. 13. X-Ray Crystal Structure of the T Helper Epitope TPPAYRPPNAPIL (SEQ ID NO:31).

FIG. 14. Molecular Model of the Fv Region of the Antibody SC100 (top view).

FIG. 15. Diagrammatic representation of Mutation PCR.

FIG. 16. Agarose Gel Representation of CTL1 L3 Mutation PCR.

FIG. 17. Agarose Gel Representation of Mutational Asymmetric PCR Results.

FIG. 18. PCR Analysis of CDR-L3 Sequence Mutations.

FIG. 19. Result of Clone 74:1 DNA Sequencing

FIG. 20. Results of CTL Assays

FIG. 21. Proliferation of T Cell Clone to Tie-2 Fc Presented by Dendritic Cells.

EXAMPLES

Material and Methods

Antigens

105AD7 is a human IgGI monoclonal antibody (Austin et at., (1989) *Immunol*, 67: 525-530) purified from tissue culture supernatant on a protein G column. Fab was produced using immobilised papain (Pierce, Chester, UK), protein A removal of Fc and size fractionation on S400 sepharose (Pharmacia, Upsala, Sweden). Polyclonal human IgG (Sigma, Poole, UK) was used as a control antibody (Sigma, Poole, Dorset, UK). Keyhole limpet haemocyanin (KLH, Sigma) was used as a control antigen to measure naive immune responses. 708 is a mouse IgG2b monoclonal antibody purified from tissue culture supernatant on a protein A column (Durrant et at., (1992) *Int. J. Cancer* 50: 811-816).

Chimeric 708 was prepared broadly according to the protocol of (Orlandi et al., (1989) *Proc. Natl. Acad. Sci (USA)* 86: 3833-3837). PCR was used to link the heavy and light chains variable region sequences from hybridoma 708 with flanking sequences from vectors M13-VHPCR1 and M13-VKPCR1 respectively. The resulting heavy chain variable region cassette was sub cloned into mammalian expression vector pSVgpt containing a human heavy chain constant region. Similarly, the 708 light chain variable region cassette was sub-cloned into the expression vector pSVhyg containing a human kappa chain constant region. Vectors were linearised with Pvul and co-transfected into nonsecreting mouse myeloma line NSO by electroporation. Transfectomas growing in 96 well dishes were selected by growth in medium containing xanthine and mycophenolic acid and supernatants screened for production of human immunoglobulin after 14 days. Screening was by an ELISA, developed with an anti-human kappa chain specific reagent (The Binding Site, Birmingham, UK). The best producing line was expanded for antibody production and chimeric antibody was prepared using a protein A agarose preparation and conditions recommended by the supplier (Bioprocessing Ltd. Consett, UK).

In Vitro Stimulation of Blood from Unimmunised Donors

Venous blood samples were taken into preservative-free heparin from normal healthy donors. All blood had been HLA typed using molecular probes. Blood samples were separated on lymphoprep (Flow laboratories, Irvine, Scotland) and peripheral blood mononuclear cells (PBMC) isolated at the plasma/lymphoprep interface. A sample of PBMCs was removed, irradiated and used as antigen presenting cells. The remaining PBMCs were depleted of CD45RO cells by magnetic bead depletion (Dynal, Oslo Norway). The CD45RA cells were used at $2\times10^6$/ml in serum free AIMV (Life Technologies, Paisley, Scotland) supplemented with 4 mM glutamine. They were stimulated with 105AD7 (0.003-30 µg/ml), 105AD7 Fab (0.01-30 µg/ml), control human IgG antibody (10 µg/ml), mouse 708 (10 µg/ml) or chimeric 708 (10 µg/ml). To assess inhibition of T cell proliferation by chloroquine or $NH_4Cl$, antigen presenting cells were pulsed with 105AD7 for 2 hrs in the presence or absence of the inhibitors. Antigen presenting cells were then washed prior to addition of naive T cells. All cultures were incubated in a humidified atmosphere of 5% $CO_2$ and 95% air at 37° C. After 5 days IL-2 (10 U/ml; Eurocetus, UK) was added. Proliferation of naive lumphocytes was quantitifed after 7-10 days. Proliferation was estimated using $^3[H]$ thymidine incorporation of quadruplicate samples. This was carried out by resuspending the bulk cultures, removing $4\times100$ µl aliquots of cells and replating in 96 well plates prior to pulsing overnight with $^3[H]$-thymidine.

Cytokine Secretion

γIFN and IL-4 were detected using a sandwich ELISA using Duo set antibodies (Genzyme, Cambridge, Mass.).

Immunofluorescence

Peripheral blood mononuclear cells ($2\times10^5$) were incubated with a panel of monoclonal antibodies directly labelled with fluorescein isothiocyanate (FITC) or phycoerythrin (PE) for dual colour analysis of lymphocyte subsets. Antibodies tested were 2H4 FITC (CD45RA) in combination with either CD4-PE or CD8-PE to enumerate memory or activated T helper and cytotoxic T cells respectively. Antibodies were obtained from Becton Dickinson (Cowley, Oxford, UK). After 30 min incubation at 4° C., PBMC were washed twice by centrifugation and analyzed using a FACScan flow cytometer (Becton Dickinson, Sunnyvale, Calif.).

Redirected Cytotoxicity

CD45RO depleted lymphocytes from normal donors were stimulated for 9-10 days as described above and were then assayed for lytic activity by a redirected cytotoxicity assay. P815 cells were labelled with chromium ($10^6$ cells labelled with 100 µCi of $^{51}$[Cr]-chromium for 1 hr at 37° C.) and washed extensively. Labelled cells were then coated with OKT3 antibody (20 µg/ml, 30 min, $5\times10^3$/well at 4° C.). Responder cells were mixed with $10^4$ chromium labelled target cells to produce ratios of 100:1-12.5:1. Chromium release was measured in 50 µl of supernatant at 4 hrs. The percentage of chromium released and cytotoxicity were calculated as follows:

$$\frac{\text{cpm test} - \text{cpm spontaneous release}}{\text{cpm maximum release} - \text{cpm spontaneous release}} \times 100 = \% \text{ cytotoxicity}$$

Competition Assay

CEA (purified by affinity chromatography from colorectal cancer liver metastases) was coated onto microtitre plates (5 µg/ml) by overnight incubation at 4° C. Plates were blocked with 1% BSA. Mouse or chimerised 708 was preincubated with biotinylated NCRC23 (Ab1) for 1 hr at 4° C. prior to adding to the CEA coated plates. Binding of biotinylated NCRC23 was detected with streptavidin horseradish peroxidase (SA-HRP; Gibco-BRL, Gaithersburg, Md.). The ELISA was developed with ABTS substrate (Sigma) solution (0.50 µg/ml, 2,2'-azino-bis-3-ethyl-benzthiazoline-6-sulphonate) in 15 ml 0.1M citrate phophate buffer, pH4.0, with 30 v/v hydrogen peroxide added at 0.3 µl/ml immediately before use. Absorbance was read at 405 nm.

Statistics

Immunological assay data was analysed by one way analysis of variance, using the Bonferroni modified least significant difference method to allow for multiple comparisons (SPSS/PC Chicago, Ill.).

Results

Example 1

To determine if a human monoclonal antibody could present T cell epitopes from its CHDRH3 region, peripheral blood lymphocytes from normal donors were enriched for CD45RA, unprimed lymphocytes and then they were stimulated with 105AD7 or control human IgG. FIG. 1 shows proliferation responses of lymphocytes from 6 naive donors to in vitro stimulation 105AD7 (10 µg/ml: '), human IgG (10 µg/ml; ♦) KLH (10 µg/ml; ●) or medium alone (▲). Proliferation was assessed at days 7, 8, 9 and 10 of in vitro culture and measured by an overnight pulse with $^3$[H]-thymidine. Results were analysed for statistical significance by one way analysis of variance, using the Bonferroni modified least significant difference method to allow for multiple comparisons. Donors expressing HLA/DR1, 3, 7, 11 and 15-phenotypes showed a significant response to 105AD7 but not to human IgG. The only consistent non-responder had an HLA/DR4,8 phenotype suggesting that these are non-permissive haplotypes. Proliferation to 105AD7 peaked at 8-10 days in all donors indicating primary kinetic responses.

Example 2

The immunophenotypes of the cells responding to 105AD7 were measured by immunofluorescence and flow cytometry (Table 1). At the start of the cultures there were twice as many CD4 as CD8 T cells and greater than 80% of the cultures expressed the CD45RA antigen. After 10 days, cultures stimulated with 105AD7 had 4.4 times more CD4 cells than CD8 cells suggesting it was the CD4 cells that were predominantly proliferating. However, this effect was not as dramatic as seen in the cells cultured with KLH, as after 10 days there were 7 times more CD4 than CD8 cells. Interestingly, there was also a shift from a predominance of CD45RA cells to CD45RO cells in response to 105AD7 stimulation, although again the response was more marked in the KLH cultures. Although there was a slight proliferation to human IgG this was not significant. Supernatants from the cultures were analysed to determine if the cells were producing γIFN (Table 1) or IL-4. Supernatant from both the 105AD7 and KLH, but not the human IgG, stimulated cultures contained γIFN. IL-4 was not detected in any of the cultures. Although the predominant cell type proliferating in response to 105AD7 were CD4 cells there were still a significant number of CD8 cells within these cultures. To determine if these cells were capable of cell lysis they were assayed in a redirected cytotoxicity assay. Significant killing was observed at all effector to target ratios. In contrast no killing was observed in either the human IgG or KLH stimulated cultures. The later was of particular interest as KLH had induced both proliferation and γIFN secretion. However, very few CD8 cells remained in the KLH cultures at day 10, suggesting that CD4 cells predominantly mediated the response to this antigen.

TABLE 1

T cell subsets and γIFN production by lymphocytes from naive donors primed in vitro with 105AD7.

| | Ratio of T cell subsets [1] | | | | Redirected Cytotoxicity | | | |
| --- | --- | --- | --- | --- | --- | --- | --- | --- |
| | CD4/8 | CD4/8 | CD45RO/ | γIFN | (% cytotoxicity) [3] | | | |
| Stimulant | pre | post | RApost | (pg/ml) [2] | 100:1 | 50:1 | 25:1 | 12.5:1 |
| 105AD7 | 2.3 | 4.4 | 2.0 | 750 | 34 ± 2 | 22 ± 3 | 15 ± 1 | 7 ± 1 |
| HigG | 2.3 | 2.3 | 1.0 | <62.5 | 6 ± 1 | 1 ± 0.2 | 1 ± 0.2 | ND |
| KLH | 2.3 | 6.9 | 6.5 | >>1,000 | 2 ± 0.01 | 2 ± 0.2 | 0±0.1 | 1 ± 0.1 |

Lymphocytes from naive donors were analysed fresh (pre) or were stimulated (post) in vitro with either 105AD7 (10 µg/ml), human IgG (10 µg/ml), or KLH (30 µg/ml). Cultures were analysed for:

The percentage of lymphocytes expressing CD4, CD8, CD45RO and CD45RA. Antigens were measured by two-colour immunofluorescence and analysed by flow cytometry.

γIFN production was measured in the 10 day culture supernatants by sandwich ELISA (range 62.5-1000 pg/ml).

Redirected cytotoxicity was measured by the ability to kill $^{51}$[Cr]-chromium labelled P815 cells coated with OKT3 antibody at different effector: target cell ratios. Significant killing was detected in the 105AD7 cultures at cell effector: target ratios.

Example 3

Having established a reproducible in vitro proliferation assay on naïve donors this culture system was used to investigate if the Fc region of 105AD7 was important in stimulating T cell proliferation. The Fc region of 105AD7 was removed to form a Fab fragment. Proliferation responses of lymphocytes from naive donors to in vitro stimulation with the 105AD7 Fab fragment (0.01-30 µg/ml; ●), to 105AD7 (0.003-30 µg/ml; ') or human IgG (0.01-10 µg/ml; ♦). Proliferation was assessed at day 9 of in vitro culture and measured by an overnight pulse with $^3$[H]-thymidine. Results were analysed for statistical significance by one way analysis of variance, using the Bonferroni modified least significant difference method to allow for multiple comparisons. Although both 105AD7 and Fab stimulate significant proliferation, FIG. 2 shows that the Fab was 1,000 fold less efficient at stimulating T cell proliferation than the whole antibody.

Example 4

Further evidence for Fc involvement in the stimulation of T cell responses by 105AD7 was provided by competition studies between 105AD7 and human IgG (FIG. 3). Proliferation responses of lymphocytes from naive donors at day 9 of in vitro stimulation with 105AD7 (10 µg/ml; ') in the presence of 0-1000 µg/ml of human IgG, or stimulation with human IgG (♦) alone at 0-1000 µg/ml4. Proliferation was assessed in quadruplicate cultures and measured by an overnight pulse with $^3$[H]-thymidine. Results were analysed for statistical significance by one way analysis of variance, using the Bonferroni modified least significant difference method to allow for multiple comparisons. Proliferation to 105AD7 was significantly inhibited by addition of 300-1,000 µg/ml of human IgG. A three and ten fold excess of human IgG significantly inhibited T cell proliferation by 15% and 66% respectively. No significant proliferation response to human IgG was observed at any concentration.

Example 5

To investigate whether 105AD7 was unique or whether presentation of T cell epitopes from other antibodies could be enhanced by improved Fc uptake, a second antibody was studied. 708 is a mouse IgG2b monoclonal antibody which mimics CEA and can stimulate T cell responses in vitro in lymphocytes from colorectal cancer patients. However, 708 failed to stimulate unprimed human T cells from healthy donors. Its mouse Fc region was therefore replaced with human Fc to see if this improved its ability to stimulate T cell responses. The chimerised antibody was produced and showed similar binding to the mouse anti-idiotype as both mouse and chimerised 708 inhibited binding of Ab1, to CEA. Stimulation of primary T cells from healthy donors by both mouse and chimeric 708 antibody was screened. Proliferation responses of lymphocytes from naive donors to in vitro stimulation with chimeric 708 (10 µg/ml: '), mouse 708 (10 µg/ml; ♦) or human IgG (10 µg/ml; ●) or medium alone (▲). Proliferation was assessed at days 7, 8, 9 and 10 of in vitro culture and measured by an overnight pulse with $^3$[H]-thymidine. Results were analysed for statistical significance by one way analysis of variance, using the Bonferroni modified least significant difference method to allow for multiple comparisons. FIG. 4 shows that only chimeric 708 and not mouse 708 induced a significant proliferative response when compared to medium alone indicating the importance of a human IgG1 constant region.

Example 6

Stimulation of primary T cells from healthy donors by both mouse and chimeric 708 antibody was screened for cytokine production. Supernatants from these cultures showed that the chimerised antibody but not the mouse anti-idiotype induced γIFN secretion (Table 2).

TABLE 2

Secretion of γIFN in cultures of lymphocytes from unimmunised donors stimulated with mouse or chimeric 708 antibodies.

| | γIFN (pg/ml) | |
|---|---|---|
| Immunogen | Primary stimulation | Secondary stimulation |
| Chimeric 708 | 250 ± 1 | 1125 ± 60 |
| Mouse 708 | <62.5 | <62.5 |
| Human IgG | <62.5 | <62.5 |
| Media | <62.5 | <62.5 |

Lymphocytes from naive donors were stimulated in vitro with either chimeric 708 (10 µg/ml), mouse 708 (10 µg/ml), human IgG (10 µg/ml) or no antigen (media). γIFN production in culture supernatants was measured by sandwich ELISA (range 62.5-1500 pg/ml), following primary stimulation for 10 days, or 5-days post-restimulation.

Example 7

It was of interest to determine if the chimerised 708 antibody could also stimulate unprimed CD8 cells to become lytically active effector T cells. FIG. 5 shows redirected cytotoxicity following a) 9 days of primary in vitro culture or b) 5 days following restimulation with either mouse 708 (♦), chimeric 708 (') or human IgG (●). Cytotoxicity was assessed by killing of $^{51}$[Cr]-chromium labelled P815 cells coated with OKT3 antibody at different effector: target cell ratios. Chimerised 708 but not mouse 708 or human IgG could stimulate T cells to induce significant cell lysis. These cultures could be boosted by further in vitro stimulation to produce a higher level of cytotoxicity (FIG. 7b).

Example 8

To prove that the cytotoxic T cell epitopes within the human monoclonal antibody 105AD7 were presented from the CDRH3 region of this human IgG1 antibody. 105AD7 was reconfigured as a scFv DNA vaccine by cloning the antibody and then joining the hypervariable regions of the heavy and light chain with either a 15 (scFv-15) or a 5 amino acid (scFv-5) linker. Alternatively the CHRH3 region of 105AD7 was cloned and spliced to its leader sequence to form a minigene. These 105AD7 DNA constructs were used to immunise balb/c mice by intramuscular injection of 100 μg of DNA admixed with a CpG oligonucleotide. FIG. 6 shows CTL responses following vaccination with A) scFv-15, B) scFv-5, C) the minigene and D) the control vector pCR3.1. Mice were vaccinated at weeks 0, 2 and 7 and the spleens harvested at week 8. The splenocytes were cultured in vitro for 6 days with 105AD7. P815 target cells were labelled with $^{51}$Cr +/−the CDRH3 peptide. Specific cell lysis was then measured using effector:target ratios of 100:1 to 12.5:1. Mice immunised with 105AD7 DNA vaccine stimulated cytotoxic T cell responses against target cells pulsed with the CDRH3 peptide.

Example 9

To prove that the deimmunised 708 antibody presented a cytotoxic T cell epitope from a tumour associated antigen. FIG. 7 shows the cytotoxicity following 28 days of primary in vitro culture of human lymphocytes with deimmunised 708 (') with restimulation on days 7, 14 and 21. Cytotoxicity was assessed by killing of $^{51}$[Cr]-chromium labelled human tumour cells expressing CEA at different effector:target cell ratios. Deimmunised 708 could stimulate T cells to induce significant cell lysis of HLA matched target cells expressing CEA.

Example 10

Optimisation of the in vivo immunisation protocol. 105AD7 was used as an example of a human Fc region linked to a mouse H-2Kb CTL epitope. 105AD7 was reconfigured as a scFv DNA vaccine by cloning the antibody and then joining the hypervariable regions of the heavy and light chains with a 5 amino acid linker. This DNA was coated onto gold particles and this DNA was administered to balb/c mice intradermally using a helium powered GeneGun (Biorad Laboratories Limited, Hemel Hempstead, UK). Four groups of animals were immunised with either ¹1) three injections of DNA with CpG adjuvant, 2) one immunisation with DNA and two with 105AD7 protein with CpG adjuvant, 3) three immunisation with 105AD7 protein with CpG adjuvant or 4) three immunisations with 105AD7 protein and Freund's adjuvant as described or by intramuscular injection of 105AD7 protein (see table 3). Splenocytes were harvested two weeks later. Naïve mice were utilised to produce feeder cells for in vitro peptide stimulation by a standard technique based on the production of lipopolysaccharide (LPS) stimulated blasts cells. On day three, these LPS blast cells were irradiated and H-2Kd peptide (100 μg per 2×10$^7$ cells incubated in 1 mL) added for 1 hour. These cells were then washed and used as feeder cells for splenocytes from immunised mice. After 5 days incubation, these cells were forwarded for routine cytotoxic T cell experiment. Assays were set up, to analyse the response against an irrelevant peptide and the H-2Kd peptide.

TABLE 3

| | Vaccination Schedule | | | |
|---|---|---|---|---|
| Week | 0 | 2 | 4 | 6 |
| 1 | DNA + CpG Gene Gun | DNA + CpG Gene Gun | DNA + CpG Gene Gun | Cytotoxic T Cell Assay |
| 2 | DNA + CpG Gene Gun | Protein + CpG IM | Protein + CpG IM | |
| 3 | Protein + CpG IM | Protein + CpG IM | Protein + CpG IM | |
| 4 | Protein + IFA IM | Protein + IFA IM | Protein + IFA IM | |

Only the group receiving a DNA prime and two protein booster immunisations showed a CTL response (FIG. 8). These results suggest that a combination of DNA priming and protein boosting gives optimal CTL responses.

Example 11

Grafting of a CTL Epitope from the MAGE-3 Protein into a Deimmunised Antibody

The antibody which was selected to deliver the CTL determinants is the de-immunised SC100 antibody (WO 01/88138). The use of a de-immunised antibody is advantageous in its utility as an epitope delivery system as the de-immunisation protocol removes any pre-existing T cell epitopes. This ensures an immunologically inert carrier that directs the immune responses against the ImmunoBody itself to be based on those epitopes grafted into the CDRs.

The epitope chosen for initial analysis is a CTL epitope based on the MAGE-3 antigen that is over-expressed by malignant melanoma.

In FIG. 9a, the heavy chain expression vector pSVgptHuIgG1 is based on pSV$_2$gpt (Mulligan and Berg, (1980) *Science*, 209: 1422-1427). It includes the ampicillin resistance gene for selection in bacterial cells, the gpt gene for selection in mammalian cells, the murine heavy chain immunoglobulin enhancer region, genomic sequence encoding the Human IgG1 constant region gene and SV40 poly A sequences. The heavy chain variable region for expression is inserted as a HindIII to BamHI fragment. This expression cassette includes the murine heavy chain promoter, the signal peptide coding sequence and the signal sequence intron, the V$_H$ gene, the V-C splice donor sequence and intron sequences. Sites in brackets have been removed In FIG. 9b, the light chain expression vector pSVhygHuCκ is based on the vector pSVhyg. It includes the ampicillin resistance gene for selection in bacterial cells, the hyg gene for selection in mammalian cells, the murine heavy chain immunoglobulin enhancer region, genomic sequence encoding the Human kappa constant region gene and including the kappa enhancer and SV40 poly A sequences. The light chain variable region for expression is inserted as a HindIII to BamHI fragment. This expression cassette includes the murine heavy chain promoter, the signal peptide coding sequence and the signal sequence intron, the V$_K$ gene, the V-C splice donor sequence and intron sequences. There are 3 EcoR1 sites internal to HuCκ. Sites in brackets have been removed. The vector pSVhygHuCκ was obtained from G Winter, Laboratory of Molecular Biology, Cambridge, UK. The constant region gene in the vector was replaced with a human Kappa constant region gene cloned from placental DNA. In order to maintain the integrity of the expression vectors after mutation a strategy was devised which would utilise the restriction sites of HindIII and BamHI at either end of the VH and VL encoding regions (see FIGS. 9a and 9b) to excise out native SC100 sequence and replace it with CDR grafted ImmunoBody sequence.

In this manner, only the grafted region would differ from the expression sequence that had already proved to be successful in the production of antibody molecules.

Since the antibody contains 6 CDRs (3 on the heavy and 3 on the light chain), it may be possible to replace any of these regions with the MAGE-3 epitope. However, there may be certain structural constraints on this generalisation, determined by the nature of the epitope to be introduced and the acceptor CDR site that is to receive it. Serious perturbations of the antibody secondary structure at the splicing site may have a deleterious effect on protein refolding to such an extent that immune function is impaired. A more rational approach based on the need to both preserve the structure of the antibody itself and more importantly to allow an element of control in the ultimate processing of the epitopes would seem to be of benefit in the design of an ImmunoBody molecule. In this respect, a strategy based on both the use of algorithms which predict proteolytic cleavage of the molecule and molecular modelling of the native and grafted antibody was devised.

Proteolytic Cleavage

Web based (internet accessible) algorithms (see Table 4) were used to scrutinise the SC100 primary sequence for sites of predicted proteosomal cleavage. This is an attempt to identify a potential hierarchy of acceptor CDR sites, which would allow favourable processing of the internalised ImmunoBody. This would allow the release of grafted epitopes for presentation in a more controlled and defined manner.

TABLE 4

Internet Sites of Proteolytic Cleavage Algorithms

| Algorithm | NetChop* | PAProC |
|---|---|---|
| Authors | C. Kesmir, A. Nussbaum, Hansjorg Schild, Vincent Detours, and S. Brunak | C. Kuttler, A Nussbaum, T. P. Dick, H-G. Rammensee and H. Schild |
| References | Manuscript submitted (C. Kesmir, personal communication) | J. Mol. Biol. 298: 417-429 (2000) Immunogenetics 53: 87-94 (2001) |
| Internet address | www.cbs.dtu.dk/services/NetChop | www.uni-tuebingen.de/uni/kxi |

*NetChop internet site is now running NetChop Version 2.0.

Therefore the analyses undertaken were specific for the ImmunoBody to be produced, both in terms of the ImmunoBody antibody framework to be utilised and the epitope sequences which are to be grafted onto this framework. Initial predictive experiments analysed the incorporation of the MAGE3 CTL epitope (FLWGPRALV) (SEQ ID NO:32) and the T helper epitope (TPPAYRPPNAPIL) (SEQ ID NO:31) into each of the SC100 CDRs. In each analysis, the whole of the antibody primary sequence was scrutinised in order for the influences of flanking region residues to be taken into account. The results of PaProC and NetChop analyses are summarised in Table 5.

TABLE 5a

NetChop Version 1.0. Number of Predicted Cleavage Sites

| Graft Site | Epitope | | | | |
|---|---|---|---|---|---|
| CDR | Native | CTL | | T Helper | |
| H1 | 0 | 0 | x | 1 | x |
| H2 | 0 | 0 | x | 1 | ✓ |
| H3 | 1 | 0 | x | 1 | x |
| L1 | 2 | 0 | x | 1 | ✓ |
| L2 | 1 | 1 | x | 1 | x |
| L3 | 1 | 0 | x | 1 | x |

TABLE 5b

PaProC Number of Predicted Cleavage Sites

| Graft Site | Epitope | | | |
|---|---|---|---|---|
| CDR | Native | CTL | T Helper | |
| H1 | 0 | 1 | 5 | x |
| H2 | 3 | 2 | 5 | ✓ |
| H3 | 3 | 1 | 4 | x |
| L1 | 6 | 2 | 6 | x |
| L2 | 3 | 2 | 5 | x |
| L3 | 2 | 1 | 4 | ✓ |

Key:
"✓" equals C-terminal cleavage of epitopic peptide
"x" equals no C-terminal cleavage NetChop, set at a default threshold of 0.8 predicts no internal cleavage of CTL peptide when spliced into H1, H2, H3, L1 and L3 (Table 5b). Insertion into L2 gives one C-terminal cleavage site after the amino acid residue F. There is one internal cleavage site for all of the T helper insertions where the Y amino acid residue is cleaved at its N-terminus. NetChop also predicted that there are no C-terminal cleavage sites for the CTL epitope, but the T helper epitope in H2 and L1 is cleaved at its C-terminus.

PaProC is more difficult to analyse empirically, since multiple cleavage sites are generated for each epitope, especially for T helper. Based on the data presented here, future sequence manipulations should therefore start with analysis of CTL in H1, H3 and L3 and T helper in H3 and L3.

These studies although only predictive in nature, indicate that caution has to be taken when designing the combination of epitopes to be grafted and the acceptor sites used. The structure of the epitopes coupled to the sequence of the CDRs and flanking region can ultimately have effects on the processing and presentation of the epitopes themselves. Here, NetChop in particular has given an indication of the likelihood of problems arising with internal cleavage of the grafted epitopes. This would obviously have a terminally deleterious effect on the presentation of these epitopes by antigen presenting cells.

Current processing dogma decrees that during processing of the epitope in the proteosome environment, C-terminal cleavage occurs at a point immediate to the C-terminus of the peptide to be presented and that no other processing occurs at this end of the peptide. This is in sharp contrast to the cleavage pattern at the N-terminus, where cleavage occurs at a site some distance upstream of the N-terminus. The peptide is then trimmed by the activity of N-terminal aminopeptidases until the epitope achieves the required length for MHC associated peptide presentation. It may therefore be possible to control the cleavage at the C-terminus of the epitope in question by providing alongside it, in the graft, a residue which is prone to cleavage when placed in this environment. This would allow processing to be initiated in a more precise manner and would greatly increase the chances of the correct peptide being forwarded for presentation. Again, the flanking residues are of importance to this process and their influence has to be taken into account. Bearing these points in mind, a series of experimental sequences were processed by the NetChop (Version 1.0) algorithm. In these experiments, both the CTL and the T helper epitope were grafted into each of the CDRs, as was performed previously. However, at each grafting site, NetChop analysis was performed after the addition, in individual steps of each of the 20 amino (or imido) acids. The results of analyses performed with the CTL epitope FLWGPRALV (SEQ ID NO:32), plus an additional amino acid variant at the C-terminus, when inserted into each of the 6 CDRs is summarized in FIG. 10a. The results are given as a percentage change induced by the insertion of the additional C-terminal amino acid from the value obtained by insertion of the epitope alone (FIG. 10b). The results are corrected for internal cleavage. Where this occurs the epitope is therefore destroyed and will not be able to be presented in a worthwhile manner. The score for these events is given as being that of the native value, so that the percentage change is recorded as zero. These events are therefore easily identifiable upon scrutiny of the graphical depiction. The addition of some of the amino acids at the C-terminus of the epitope may lead to an increase in the ability of the epitope to be successfully processed by C-terminal cleavage. These include C, G, K, R and S and to an extent in CDR H1 only, A. NetChop has also identified some amino acids, such as F, I P, V W and Y whose effects allied to the SC100 sequence hinder the processing of the epitope. It therefore becomes important to analyse the sequence at the junction site, so that the first residue (which is part of the antibody scaffold) downstream from the spliced epitope does not consist of one of those residues which is likely to lead to inappropriate processing of the epitope. This may give a further element of control over the resultant processing of the epitope by antigen presenting cells, allowing a semblance of predictability into the formation of the epitopic stimulant.

Also determined through predictive analyses using amino acid insertions at the C-terminus, is the ability to predict the removal of a splicing point which is internally situated within the grafted epitope itself. An example of this would be to try to remove the predicted cleavage site at Y (underlined) in the T Helper sequence TPPAYPPNAPIL (SEQ ID NO:99) (indicated to be cleaved in each of the CDRs, as shown in Table 5a and 5B epitope column 3). Analysis has shown that removal of internal cleavage sites may be possible using the influence of amino acids placed at the C-terminus of the epitope (FIG. 11). Here, the C-terminal cleavage of the sequence is altered to a position which maintains the integrity of the epitope to be presented, with obvious beneficial effects for presentation of the peptide. Some amino acids (such as A, C, G, K, Q R and S) both lower the internal value of the mid-epitope tyrosine and divert cleavage towards the C-terminal leucine, with beneficial effects for presentation of this epitope. Again, it appears to be important to take such predictive data into account when designing both the epitope and the splicing point for the production of a viable ImmunoBody construct.

Molecular Modeling of the SC100 Antibody and Derivatives
Modelling of the Fv.

Antibodies lend themselves to molecular modelling with relative ease due to their very high sequence similarity, even in the so-called variable region (Fv). Also, a large number of antibodies have been crystallized, whose co-ordinates have been deposited in the public access database, the Protein Data Bank (PDB). Other factors facilitate the modelling of antibodies such as canonical classification of the loop regions in the Fv, which are paramount to the normal function of binding to a target antigen.

Standard homology modeling techniques were employed to model the Fv region. This began with sequence alignment of the SC100 antibody against a database of sequences that correspond to crystal structures in the PDB. The heavy chain (without CDR3), light chain and CDR3 of the heavy chain were examined individually. The results of these analyses are shown in Tables 6, 7 and 8.

TABLE 6

Heavy Chain Alignment (without CDR3)

```
1F4YH top
CRYSTAL STRUCTURE OF AN ANTI-CARBOHYDRATE ANTIBODY DIRECTE
AGAINST VIBRIO CHOLERAE 01 IN COMPLEX WITH ANTIGEN
MOL_ID: 1;
MOLECULE: ANTIBODY S-20-4, FAB FRAGMENT, LIGHT CHAIN;
CHAIN: L;
MOL_ID: 2;
MOLECULE: ANTIBODY S-20-4, FAB FRAGMENT, HEAVY CHAIN;
CHAIN: H
MOL_ID: 1;
ORGANISM_SCIENTIFIC: MUS MUSCULUS;
ORGANISM_COMMON: MOUSE;
SECRETION: ASCITES;
MOL_ID: 2;
ORGANISM_SCIENTIFIC: MUS MUSCULUS;
ORGANISM_COMMON: MOUSE;
SECRETION: ASCITES
P. M. ALZARI, H. SOUCHON
Length = 216
Score = 172 bits (432), Expect = 3e-44
Identities = 79/98 (80 Positives = 90/98 (91%))

Query:  1 QVQLQESGGGLVKAGGSLKLSCAASGFAFNTYDMAWVRQTPEKRLEWVAYIGSGGDRTYY  60 (SEQ ID NO: 91)
           VQL ESGGGLV  GGSL LSCAASG  F TYDM WVRQTPEKRLEWVA I SGG RTY
Sbjct:  1 EVQLEESGGGLVTPGGSLRLSCAASGYVFSTYDMSWVRQTPEKRLEWVAFISSGGGRTSY  60 (SEQ ID NO: 92)

Query: 61 PDTVKGRFTISRDNGKNTLYLQLNSLKSEDTAMYYCAR                         98 (SEQ ID NO: 93)
          PDTVKGRFTISRD  KNTLYLQ  SL SEDTAMYYC R
Sbjct: 61 PDTVKGRFTISRDDAKNTLYLQMSSLQSEDTAMYYCTR                         98 (SEQ ID NO: 94)
```

TABLE 7

Light Chain Alignment

```
2JELL top
JEL42 FAB/HPR COMPLEX
MOL_ID: 1;
MOLECULE: JEL42 FAB FRAGMENT;
CHAIN: L, H;
MOLID: 2;
MOLECULE: HISTIDINE-CONTAINING PROTEIN;
CHAIN: P;
SYNONYM: HPR
MOL_ID: 1;
ORGANISM SCIENTIFIC: MUS MUSCULUS;
ORGANISM COMMON: MOUSE;
STRAIN: BALB/C;
MOL_ID: 2;
ORGANISM_SCIENTIFIC: ESCHERICHIA COLI
L. PRASAD, E. B. WAYGOOD, J. S. LEE, L. T. J. DELBAERE
Length = 217
Score = 223 bits (562), Expect = 2e-59
Identities = 105/109 (96 Positives = 108/109 (98%))

Query:  1 DVLMTQTPLSLPVSLGDQASISCRSSQSIVHSNGNTYLEWYLQKPGQSPKLLIYKVSNRF  60 (SEQ ID NO: 95)
           DVLMTQTPLSLPVSLGDQASISCRSSQSIVH NGNTYLEWYLQKPGQSPKLLIYK SNRF
Sbjct:  1 DVLMTQTPLSLPVSLGDQASISCRSSQSIVHGNGNTYLEWYLQKPGQSPKLLIYKISNRF  60 (SEQ ID NO: 96)

Query: 61 SGVPDRFSGSGSGTDFTLKISRVEAEDLGIYYCFQGSHVPWTFGGGTKL  109 (SEQ ID NO: 97)
          SGVPDRFSGSGSGTDFTLKISRVEAEDLG YYCFQGSHVP TFGGGTKL
Sbjct: 61 SGVPDRFSGSGSGTDFTLKISRVEAEDLGVYYCFQGSHVPYTFGGGTKL  109 (SEQ ID NO: 98)
```

TABLE 8

CDR3 Alignments

```
Initially:
2MPAH top
BACTERICIDAL ANTIBODY AGAINST NEISSERIA MENINGITIDIS
MOL_ID: 1;
MOLECULE: MN12H2 IGG2A-KAPPA;
CHAIN: L;
FRAGMENT: FAB FRAGMENT;
BIOLOGICAL UNIT: MONOMER;
MOL_ID: 2;
MOLECULE: MN12H2 IGG2A-KAPPA;
CHAIN: H;
FRAGMENT: FAB FRAGMENT;
BIOLOGICAL UNIT: MONOMER;
MOL_ID: 3;
MOLECULE:
 CONJUGATE OF PORA P1.16 PEPTIDE WITH FLUORESCEI
CHAIN: P;
FRAGMENT: APEX OF EXTRACELLULAR LOOP 4 (VR2) OF PORA,
RESIDUES 180-187;
SYNONYM: P1.16, AC-TKDTNNNLC(FLUORESCEIN)-NH2;
ENGINEERED: YES;
BIOLOGICAL_UNIT: MONOMER
MOL_ID: 1;
ORGANISM_SCIENTIFIC: MUS MUSCULUS;
ORGANISM_COMMON: MOUSE;
STRAIN: BALB/C;
CELL_LINE: MN12H2 MURINE-MURINE HYBRIDOMA;
CELL: B-LYMPHOCYTE HYBRIDOMA;
MOL_ID: 2;
ORGANISM_SCIENTIFIC: MUS MUSCULUS;
ORGANISM_COMMON: MOUSE;
STRAIN: BALB/C;
CELL_LINE: MN12H2 MURINE-MURINE HYBRIDOMA;
CELL: B-LYMPHOCYTE HYBRIDOMA;
MOL_ID: 3;
SYNTHETIC: YES;
OTHER DETAILS: SEQUENCE FROM NEISSERIA MENINGITIDIS
(MENINGOCOCCUS), STRAIN: H44/76, VARIANT: P1.16;
J. M. H. VAN DEN ELSEN, J. N. HERRON, J. KROON, P. GROS
Length = 224
Score = 40.2 bits (92), Expect = 1e-04
Identities = 15/24 (62 Positives = 18/24 (74%))
```

TABLE 8-continued

CDR3 Alignments

```
Query:  1 YYCARHYGHYVDYAVDYWGQGTTV  24      (SEQ ID NO: 90)
          YYC   Y  Y D   DYWGQGTTV
Sbjct: 94 YYCSIIYFDYADFIMDYWGQGTTV 117      (SEQ ID NO: 88)
```

The alignment for the CDR-H3 alignment was discounted after studying rules defined by Morea et al., (1998) *J. Moi. Biol.* 275: 269-294). These show sequence specificity at the YYCAX (SEQ ID NO:55) and the XYWG (SEQ ID NO:57) positions, which can determine the presence of beta-bulges in the loop. The protein database was checked again for loops of correct length, which had the YYCAR (SEQ ID NO:54) and DYWG (SEQ ID NO:56) sequence. The sequence in between these two points was examined closely for any resemblance with the SC100 CDR-H3 sequence and X-ray crystal structures with loops of the same length were selected. These are shown in Table 9.

TABLE 9

Selected CDR-H3 Sequences With X-Ray Crystal Lengths Similar to SC100

| PDB Code | Sequence | Chosen |
|---|---|---|
| Query | YYCAR HYGHYVDYAVDY (SEQ ID NO: 69) | |
| 1AP2 | YYCAR REVYSYYSPLDV (SEQ ID NO: 70) | ✓ |
| 1C12 | YYCVT SLTWLLRRKRSY (SEQ ID NO: 71) | |
| 1DEE | YYCAK VKFYDPTAPNDY (SEQ ID NO: 72) | ✓ |
| 1DNO | YYCAR PPHDTSGHYWNY (SEQ ID NO: 73) | |
| 1DSF | YYCGR SPIYYDYAPFTY (SEQ ID NO: 74) | |
| 1IAI | YFCAR DGYYENYYAMDY (SEQ ID NO: 75) | ✓ |
| 1IGA | YYCAR DPYGGGKSEFDY (SEQ ID NO: 76) | ✓ |
| 1IGM | YYCAK HRVSYVLTGFDS (SEQ ID NO: 77) | ✓ |
| 1I11 | YYCNA ISTTRDYYALDY (SEQ ID NO: 78) | |
| 1JRH | YYCAR RAPFYGNHAMDY (SEQ ID NO: 79) | ✓ |
| 1MNU | YYCSI IYFDYADFIMDY (SEQ ID NO: 80) | |
| 1MPA | YYCSI IYFDYADFIMDY (SEQ ID NO: 81) | |
| 1OSP | YYCAR SRDYYGSSGFAF (SEQ ID NO: 82) | |
| 1QLR | YYCAR PPHDTSGHYWNY (SEQ ID NO: 83) | |
| 1SBS | YYCTR GAYYRYDYAMDY (SEQ ID NO: 84) | ✓ |

TABLE 9-continued

Selected CDR-H3 Sequences With X-Ray Crystal Lengths Similar to SC100

| PDB Code | Sequence | Chosen |
|---|---|---|
| 6FAB | YFCAR SEYYGGSYKFDY (SEQ ID NO: 85) | ✓ |
| 8FAB | YYCAR DPDILTAFSFDY (SEQ ID NO: 86) | ✓ |
| 1HEZ | YYCAK VKFYDPTAPNDY (SEQ ID NO: 87) | ✓ |

These sequences were then aligned to find the sequence most similar to the SC100. This was done using the CLUSTAL W (1.81) multiple sequence alignment (Table 10). Of the sequences identified, 1SBS was chosen from these alignments as the template for modelling CDR3.

TABLE 10

CLUSTAL Multiple Sequence Alignment

|  |  |  | Identities |
|---|---|---|---|
| SC100 | YYCARHYGHYVDYAVDY | (SEQ ID NO: 58) | 8 |
| 1IAI | YFCARDGYYENYYAMDY | (SEQ ID NO: 59) | |
|  | * ***       ** ** | | |
| SC100 | YYCARHYGHYVDYAVDY | (SEQ ID NO: 58) | 7 |
| 6FAB | YFCARSEYYGGSYKFDY | (SEQ ID NO: 60) | |
|  | * ***       *  ** | | |
| SC100 | YYCARHYGHYVDYAVDY | (SEQ ID NO: 58) | 7 |
| 1IGA | YYCARDPYGGGKSEFDY | (SEQ ID NO: 61) | |
|  | *****        ** | | |
| SC100 | YYCARHYGHYVDYAVDY | (SEQ ID NO: 58) | 7 |
| 8FAB | YYCARDPDILTAFSFDY | (SEQ ID NO: 62) | |
|  | *****         ** | | |
| SC100 | YYCARHYGHYVDYAVDY | (SEQ ID NO: 58) | 9 |
| 1SBS | YYCTRGAYYRYDYAMDY | (SEQ ID NO: 63) | |
|  | *** *     *** ** | | |
| SC100 | YYCARHYGHYVDYAVDY | (SEQ ID NO: 58) | 6 |
| 1DEE | YYCAKVKFYDPTAPNDY | (SEQ ID NO: 64) | |
|  | ****          ** | | |
| SC100 | YYCARHYGHYVDYAVDY | (SEQ ID NO: 58) | 6 |
| 1HEZ | YYCAKVKFYDPTAPNDY | (SEQ ID NO: 65) | |
|  | ****          ** | | |
| SC100 | YYCARHYGHYVDYAVDY | (SEQ ID NO: 58) | 6 |
| 1AP2 | YYCARREVYSYYSPLDV | (SEQ ID NO: 66) | |
|  | *****         * | | |
| SC100 | YYCARHYGHYVDYAVDY | (SEQ ID NO: 58) | 9 |
| 1JRH | YYCARRAPFYGNHAMDY | (SEQ ID NO: 67) | |
|  | *****  *  * *** | | |
| SC100 | YYCARHYGHYVDYAVDY | (SEQ ID NO: 58) | 8 |
| 1IGM | YYCAKHRVSYVLTGFDS | (SEQ ID NO: 68) | |
|  | **** *  **   * | | |

Molecular Modelling Methodology.

All modelling was performed on a SGI Octane 2 R12000 workstation, using Sybyl 6.7 (Tripos, UK).

The light chain of 2JEL was loaded and residues were mutated to that of the required sequence. Hydrogen atoms were then added. Those residues that had been added to the structure were then minimized as follows:

Hydrogen atoms only (rest of protein held fixed in position) were minimized by 100 iterations of Steepest descent optimisation, followed by Conjugate gradient method to a convergence criterion of an energy derivative of 0.01 kcal/mol/angstrom2.

Sidechain atoms were allowed to move (rest of protein held) and minimized as in step 1.

Sidechain and backbone atoms were allowed to move (rest of protein held) and minimized as in step 1.

The model was then scrutinized by eye, to ensure no errors had been incorporated. For the heavy chain, modelling was performed as in the light chain section, but CDRH3 had been removed from the protein chain. Minimization was performed in the same manner as the light chain.

The CDR3 loop from the heavy chain of 1SBS was mutated to that of the SC100. The structure was then overlaid onto the existing heavy chain model, using residues YYCAR (SEQ ID NO:54) and DYWG (SEQ ID NO:56) to position the loop. The loop was then grafted through its N-terminus onto the framework at position, and through its C-terminus at position. Manual rotation of backbone dihedrals were performed to bring the framework 4 region back to its usual position (quirk of Sybyl). Joining regions and newly incorporated residues were minimized as above.

VH-VL Construction

To provide a model of the Fv, the constructed VH and VL regions had to be brought together as a pair. In order to do this, the original sequence alignments were checked to find matches that ranked highly in both heavy and light chain scores. This approach should yield an Fv onto which we could superimpose the individual VH and VL using conserved residues in the framework. The top five ranked structures are shown in Table 11. 1ATM was chosen for superimposition of the VH and VL. Once this had been performed, residues at the VH-VL interface were checked for bad clashes and minimised as needed. The completed Fv is shown in FIG. 12. The model of the Fv was then checked using PROCHECK (Laskowski et al., (1993) *J. Appl. Crystallog* 26: 283-291) to ensure that backbone and sidechain conformations were of good quality.

TABLE 11

Ranking of Heavy and Light Chains for VH-VL Superimposition

| Sample | Heavy rank | Light rank |
|---|---|---|
| 1ATM | 21 | 12 |
| 1CLZ | 20 | 13 |
| 1BLN | 14 | 20 |
| 2HIP | 16 | 30 |
| 1CLY | 18 | 31 |

Epitope Incorporation Modelling.

The major aim of the modeling exercise has been to examine the possibility of incorporation of immunologically active epitopes into the CDRs of the SC100 carrier antibody. Therefore, in line with the grafting results of proteolytic cleavage experiments, attempts were made to model the epitopic peptides FLWGPRALV (CTL) (SEQ ID NO:32) and TPPAYRPPNAPIL (T Helper) (SEQ ID NO:31) into appropriate SC100 CDRs. The combinations chosen were:

CTL in L3
TH in L1
CTL in H2
TH in L3

To aid in modelling, both epitope sequences were tested against sequence and structure databases. The CTL1 epitope yielded no closely related sequences. The TH epitope resides in the C-terminal portion of Human hepatitis b viral capsid (hbcag) protein, which has been crystallized (PDB code: 1QGT). As can be seen from FIG. 13, this portion of the protein exists in an extended, non-structured form, partially due to the high content of proline in the sequence. Initial sequence alignments were produced as a guide to the insertion of these peptides into the antibody model. These are shown in Table 11. Similar residues are highlighted in green. Each model is described separately below.

CDR-L1 TH Epitope Insertion

As has been mentioned previously, the TH epitope has a high content of proline, which can mean forcing the sequence into a hairpin loop often observed in CDRs may be very difficult. However, CDR1 in the light chain lies in a relatively extended conformation along the top surface of the Fv. Also, because most of the loop is observed near the surface, it should be involved in less structural constraints as some parts that are buried within the structure. This is highlighted in FIG. 14. The TH sequence was incorporated into the section of the CDR1 shown in the alignment viewed as Table 12. Residues which had been mutated were minimised as before. There were little or no problems with the incorporation of this epitope into the CDR1. Small sidechain clashes were alleviated by minimisation.

TABLE 12

Original Alignments for Epitope/CDR Incorporation

| | | |
|---|---|---|
| CDR-L1 | RSSQSIVHSNG[illegible]Y[illegible]E | (SEQ ID NO:53) |
| TH | TPPAYRPP[illegible]P[illegible]L | (SEQ ID NO:52) |
| CDR-L3 | [illegible]QG[illegible]HVPWT | (SEQ ID NO:48) |
| CTL | [illegible]LW[illegible]PRALV | (SEQ ID NO:49) |
| CDR-H2 | YIGSGGDRT[illegible]Y[illegible]D[illegible]KG | (SEQ ID NO:50) |
| CTL | FL[illegible]G[illegible]R[illegible]V | (SEQ ID NO:49) |
| CDR-H3 | HYGH[illegible]VDYAVDY | (SEQ ID NO:51) |
| TH | TPPA[illegible]RPPNAPIL | (SEQ ID NO:52) |

CDR-L3 CTL Epitope Insertion

Upon examination of the above alignments, it was thought that the CTL epitope may have a sequence too dissimilar to that of the antibody, which may make modelling difficult. To resolve this problem, a loop from a crystal structure of an antibody was used to model the inserted sequence. The alignment is shown below, with similar residues highlighted:

```
line.pdb CDR-L3 YFCALWYSNLWVFGGG (SEQ ID NO: 47)

CTL epitope            FLWGPRALV      (SEQ ID NO: 49)
```

It was noted from antibody structure with the LW sequence near the N-terminus of the loop, that the sidechain orientation of the tryptophan was unusual, and highly conserved in antibodies with this sequence. Because this is the largest sidechain group to be incorporated in the epitope sequence, the priority in modelling was the correct positioning of it. The GP sequence fitted well in to the observed hairpin structure seen in the template CDR-L3.

The CDR-L3 was taken from file line.pdb and mutated to the desired sequence in Sybyl. This was then grafted on to the existing framework of the antibody between the cysteine and the valine. Sidechains of inserted residues were minimised, and the model was checked for any unusual sidechain clashed.

CDR-H2 CTL Epitope Insertion

The alignment of this epitope with the latter part of CDR-H2 is encouraging, with 4 of the 9 residues showing similarity with the sequence already present in the antibody. Also, the proline is central in each section, and when examined in the structure, is apparent at the bottom turn of the CDR. This case was relatively facile to model, with residues being mutated to the desired sequence, and minimised as described.

CDR-H3 TH Epitope Insertion

As mentioned in the CDR-L1 insertion modelling, this epitope is likely to exist in a relatively extended conformation, mainly due to the high proline content. To form a loop which would be capable of insertion into the space restricted CDR-H3 position, the epitope would have to demonstrate a tight turn within part of the structure, and b-sheet like conformation in the rest of the peptide. It is the authors' opinion that this would not be possible for the TH epitope, and insertion of this peptide into this area would yield a defectively folded antibody. Therefore, this epitope has not been modelled.

Primer Design and OLE technology

The primers are designed to replace the CDRs chosen with the epitope of interest. This is performed by a variation on the overlap extension (OLE) technique used for many DNA mutations. Unlike site directed mutagenesis which is mainly aimed at introducing point mutations, OLE allows the mutation of a number of nucleosides at once so that the need for sub-cloning is kept to a minimum. A primer is designed based on the sequences 5' and 3' of the length of DNA to be mutated and are manufactured to be exactly complementary to these regions. Providing sufficient complementarity is achieved here based on the number of residues chosen and their annealing strengths, the site in between this region can be any sequence of DNA. The complementarity at either end will still allow annealing of this primer to take place during PCR. When used in conjunction with other forward and reverse primers, this has the effect of introducing the mutation into the newly synthesised DNA strand. Since this in the next PCR round constitutes a template strand, the mutation is faithfully duplicated by the polymerase enzyme and therefore amplified throughout subsequent PCR. Usually primers are manufactured to mutate the same number of bases that were present in the original sequence. However, this technique can also be used to introduce extra bases as well as reduce the number of bases in a sequence. Here extra care has to be taken with the design of the primers so that the formation of secondary structures such as hairpin loops is avoided and DNA polymerase activity is not impaired.

This study highlighted the fact that although incorporation of many different primary structures is accepted in this CDRH3, there may be instances where grafted sequences lead to the integrity of the antibody structure being compromised. Modelling studies, such as this one, indicate that care has to be taken when undergoing epitope grafting. Loop modelling can help to identify those sequences which are going to compromise antibody folding which would lead to failure in the production of an antibody delivery vehicle and utility of a vaccine.

Of the four epitope/CDR combinations chosen for the modelling studies, it is interesting to note, that the T helper epitope was unable to be modelled into CDR-H3 due to structural constraints. Many helper determinants are much larger than their CTL counterparts, so this may be indeed the case for many helper determinants. Although data for this phenomenon has only been generated for the SC100 antibody it is also interesting to note that the CDR-L1 may be a more appropriate acceptor site for helper determinants. TPPAYRPNNAPIL (SEQ ID NO:100) cause modelled into CDR-L1 due to its more relaxed structure, which may also be the case for other helper determinants. Based on the results of the proteolytic cleavage and modelling studies the following initial construct variants were chosen:

CTL into CDR-L3

TH into CDR-L1

Based on the modelling study data, which had highlighted CDR-H2 with the potential to favourably accommodate the CTL epitope readily due to similarities in sequence, this graft was initiated.

CTL into CDR-H2

Mutation PCR

Once the epitopic grafts had been chosen, a combination of sequence data analysis and de novo primer design should allow the incorporation of such grafts into the chosen CDRs using the polymerase chain reaction (PCR). For initial prototype ImmunoBody construction, primers were designed in order to facilitate the grafting of the epitope/CDRs combinations described above and these primers are presented in Table 13a.

TABLE 13a

CDR Mutating Primers

| Name | Sequence |
|---|---|
| CTL1 L3 | CTGGGAAATTATTACTGCTTCCTGTGGGGTCC (SEQ ID NO: 37)<br>AAGGGCCCTCGTTTTCGGTGGAGGCACCAAG (SEQ ID NO: 38) |
| TH1 L1 | CAAGCCTCCATCTCTTGCACTCCTCCAGCCTA (SEQ ID NO: 39)<br>TAGACCACCAAATGCCCCTATCTTATGGTACCTGCAGAAACCA (SEQ ID NO: 40) |
| CTL1 H2 | ATTGGTAGTGGTGGTTTCCTGTGGGGTCCAAG (SEQ ID NO: 41)<br>GGCCCTCGTTCGATTCACCATTTCC (SEQ ID NO: 42) |
| TH1 H3 | ATGTATTACTGTGCAAGAACTCCTCCAGCCTA (SEQ ID NO: 43)<br>TAGACCACCAAATGCCCCTATCTTATGGGGTCAAGGAACCACG (SEQ ID NO: 44) |
| CTL1 | TTCCTGTGGGGTCCAAGGGCCCTCGTT (SEQ ID NO: 45) |
| TH1 | ACTCCTCCAGCCTATAGACCACCAAATGCCCCTATCTTA (SEQ ID NO: 46) |

TABLE 13b

SC100 Specific Oligonucleotide Primers

| Name | Sequence |
|---|---|
| GD SC100 FORH + L | GTCGACCTGCAGCCCAAGCTT (SEQ ID NO: 33) |

TABLE 13b-continued

SC100 Specific Oligonucleotide Primers

| Name | Sequence |
| --- | --- |
| 2 H FOR | GCTTATCATCGATAAGCTTAT (SEQ ID NO: 34) |
| GD SC100 REVL | TGTGAGACTCTGCCAGGATCC (SEQ ID NO: 35) |
| GD SC100 REVH | CAGAAAGCTAGCTTGGGATCC (SEQ ID NO: 36) |

These primers are then utilised in appropriate combinations with the primers detailed in Table 13b for to yield a three primer system capable of mutation the CTL and T helper sequences into the SC100 CDRs. In this scenario, two forward primers are used and anneal to the template strand at similar temperatures (the annealing temperature). This primes the DNA polymerase activity, which then fills in complementary base pairs. In conjunction with the action of the reverse primer, this amplifies the DNA template strands exponentially through recycling of denaturing, annealing and elongation temperatures. In early cycles, if the mutation primer is able to anneal to the target strand, the mutation is then incorporated into subsequent template strands. A diagrammatic representation of this process is given in FIG. 15. The ease of annealing of the mutation primer governs the ratio of mutated DNA present in the amplified mixture. Mixtures of native (non-mutated) and mutated PCR products can then be separated by cloning.

Lead experiments utilised the three primer PCR system to incorporate FLWGPRALV (SEQ ID NO:32) into SC100 CDR-L3. PCR was performed using pSVhyg SC100 Chimaeric VK, HuCK plasmid as a template for the SC100 light chain and an equimolar combination of the primers GD SC100 ForH+L, GD SC100 REVL and CTL1 L3 were used to prime the PCR reaction. Standard PCR conditions and reagents were used and applied to PCR cycles consisting of 45 seconds at 94° C., 45 seconds at 56° C. and 90 seconds at 72° C. Thirty cycles of these temperatures allowed the amplification of PCR products in large enough concentrations to be viewed by standard agarose gel electrophoresis. A representation of the agarose gel, identifying FLWGPRALV (SEQ ID NO:32) encoding SC100 CDR-L3 mutated PCR products is shown in FIG. 16. In this Figure the differences in utility of the mutation primer are highlighted in the difference of product sizes found in lanes 3 and 5. The upper and lower band configuration in lane 5 is consistent with the products of amplification theorised in FIG. 15. The upper band therefore should contain a proportion of mutated sequence, since the mutation primer is clearly able to anneal to the template strand, as shown by the presence of the lower band (which represents truncated, mutated sequence). Therefore cloning of the PCR products visually represented in lane 5 should be able to isolate mutated (non-truncated) PCR product.

In order to facilitate easier cloning, it would be advisable to try to alter the relative concentrations of the different species of PCR products in favour of the mutated, non-truncated sequence. This can be performed by asymmetric PCR. Here, the product represented in FIG. 16, lane 5, lower band, is, itself, used as the reverse primer in conjunction with the addition of the forward primer (in this instance GD SC100 ForH+L). Amplification using these primers under the same conditions as the original PCR, leads to the production of an excess of mutated sequence, since this sequence is represented in the reverse primer. The result of this PCR is shown in FIG. 17. The products of lanes 3 and 4 were deemed to be suitable and were forwarded for cloning. The increased amount of DNA presenting the upper band and the decrease in the levels of truncated-mutation sequence (no lower band visible) when compared to the previous and parental PCR (lane 2) lend credence to the notion that the asymmetric PCR has indeed produced high levels of mutated (non-truncated) sequence.

Cloning and Sequencing

Once mutational PCR has been undertaken, cloning and subsequent sequencing of the PCR products generated would indicate whether the appropriate mutations have been introduced. As one can see from FIG. 15 both native and mutated sequence will be present in the PCR products derived. Identifying those clones with mutations from the native background can be achieved in a number of ways. One way is to grow up clones and purify plasmid from each for sequencing analysis. This is a rather labour intensive exercise, especially when dozens of clones need to be processed at once. The use of PCR can assist in bypassing most of this work by identifying those clones which contain the mutated sequence. Here, primers are manufactured based on the mutated sequence only (i.e. without the portions complementary to the native sequence). PCR amplification using such a primer as the forward primer in conjunction with the reverse primer of the original reaction should only yield amplification products in those clones where the mutation is present. In this manner, many clones can be analysed quickly and efficiently and yield products which can verify, due to their size, where on the native sequence the mutation has been introduced. Clones giving positive results here would then be used to produce plasmid for sequence verification.

PCR products represented in FIG. 18 were therefore forwarded for cloning. This was achieved by using the TOPO TA cloning kit (Invitrogen Corporation, San Diego, Calif., USA). Here, the cloning vector (pCR®2.1-TOPO®) is supplied with single 3'-thymidine (T) overhangs alongside Topoisomerase I which is covalently bound to the vector. The cloning strategy takes into account the non-template dependent terminal transferase activity of the *Thermus aquaticus* (Taq) enzyme used in the generation of PCR products which adds a single deoxyadenosine (A) to the 3' end of the PCR product. The T overhangs, therefore provide a "sticky end" for base pairing of the A and T nucleotides, a reaction which is catalysed by Topoisomerase I. Thus in a simple, one step reaction (virtually) any PCR products can be cloned into this vector. Transformation of appropriate strains of *E. coli* facilitates the growing of PCR incorporated pCR®2.1-TOPO® plasmid for DNA sequencing analysis. As mentioned above transformed *E. coli* can be used directly in PCR reactions to analyse the mutation content of individual clones. In the context of FLWGPRALV (SEQ ID NO:32) incorporation into CDR-L3 this was achieved using pCR®2.1-TOPO® transformed clones with primers CTL1 L3 and GD SC100 REVL (see Tables 13a and 13b respectively). Agarose gel representation of the results of these PCR analyses is shown in FIG. 18.

These experiments yielded many cloned products one of, which was named 74:1. This clone was forwarded for plasmid purification in order for DNA sequencing to verify the presence of the incorporated mutation. The results of sequence analysis are shown in FIG. 19.

Much the same overall strategy was utilised to incorporate the T helper epitope into CDR-L1. In lead experiments, this epitope would be used alongside that of the CTL epitope in order to ascertain the beneficial (or otherwise) effects of T cell help for CTL activity. Thus the manufacture of a double mutant was attempted, which incorporated the CTL graft in CDR L3 and the T helper graft in CDR-L1. Successful mutation to produce the 74:1 clone meant that this construct could be used as a template to mutate the T helper into CDR-L1. Success at this attempted mutation would obviously lead to a double mutant. This was indeed the case and asymmetric PCR to increase the ratio of mutant to native DNA sequence was again successful. These products were therefore forwarded for cloning. Cloning was again performed in the manner described using the Invitrogen TOPO TA cloning strategy. Clones were positively identified with mutated CDR-L1 using PCR with the THL1 primer and one clone, namely 213:4 was forwarded for DNA sequence analysis. Sequence data for this clone is presented in FIG. 20.

DNA Vaccination

In these studies, the primers have been carefully designed both to introduce appropriate primers into the CDRs of interest and to allow splicing of mutated DNA back into the original plasmids used for protein expression. This provides a way of examining the effects of the mutations produced against a background of native protein. The use of PCR also allows the sub-cloning of interesting products into other intermediate vectors in order for interim experiments to be performed. In this manner, we were able to introduce native and CDR mutated sequences into vectors appropriate for DNA vaccination experiments to be performed.

In order to perform DNA vaccination experiments in a transgenic mouse system, the plasmid incorporated as the vaccine vehicle must contain a eukaryotic promoter sequence in order for this DNA to be transcribed and translated. Since the pCR®2.1-TOPO® vector contains a prokaryotic promoter region, so the mutated sequences of clones 74:1 and 213:4 had to be spliced into an alternate vector. Again an Invitrogen vector was chosen to achieve this, namely the vector pCR3.1®. This vector contains the cytomegalovirus (CMV) immediate-early promoter allowing high level expression of cloned genes in a eukaryotic system. Simple TA cloning experiments again facilitated the introduction of the 74:1 and 213:4 mutated sequences into this vector. To signify their difference from the pCR®2.1-TOPO® generated clones, each clone isolated containing the pCR3.1® vector was prefixed with the letter "C". Such incorporation was also performed on native SC100 light chain PCR products (generated from the plasmid pSVhyg SC100 Chimaeric VK, HuCK) and native heavy chain products (generated from the plasmid pSVgpt SC100 Chimaeric VH). Cloned versions of these constructs were named K2 and H8 for the light chain and heavy chain versions respectively.

DNA vaccination itself was performed using GeneGun technology (Biorad Laboratories Limited, Hemel Hempsted, UK). Briefly, plasmid DNA is introduced intradermally into animals using a helium powered gun. The bullets take the form of gold particles which can be coated with DNA of choice. In our case plasmids produced from the clones 74:1, 213:4, K2 and H8 were mixed with gold particles and used to immunize groups of four mice. The following immunizations were studied:

C74:1 plasmid
C213:4 plasmid
K2 plasmid
C74:1 plasmid plus H8 plasmid

Groups of mice with having no immunisations were set up as well as positive control mice. These were mice immunised with the peptide FLWGPRALV (SEQ ID NO:32) in an appropriate immunisation regime for peptide immunogens.

Cytotoxic T Cell Assays

The end point of these initial studies on epitope/CDR incorporation is to generate CTL responses against the CDR introduced T cell epitope. These studies were performed in transgenic mice bearing the gene, which produces human HLA-A2 molecules, allowing translational study of human immune epitopic function in these mice. Again, the appropriate epitope to examine ImmunoBody proof of principle have been utilised, since the MAGE-3 epitopic peptide FLWGPRALV (SEQ ID NO:32) is known to bind with high affinity to HLA-A2.

Splenocytes from immunised and control mice were harvested and cultured using standard tissue culture techniques and growth media. Naïve mice were utilised to produce feeder cells for in vitro peptide stimulation by a standard technique based on the production of lipopolysaccharide (LPS) stimulated blasts cells (again of spleen origin). On day three, these LPS blast cells were irradiated and MAGE-3 peptide (FLWGPRALV: 100 µg per $2\times10^7$ cells incubated in 1 mL) (SEQ ID NO:32) added for 1 hour. These cells were then washed and used as feeder cells for splenocytes from immunised mice. After 5 days incubation, these cells were forwarded for routine cytotoxic T cell experiment. Assays were set up, to analyse the response against no peptide, an irrelevant peptide and the MAGE-3 peptide. The results of CTL assays are given in FIG. 20. The highest responder mice are viewed for each immunisation set.

In mice immunised with MAGE3 peptide there is killing at the highest effector: target ratio (E:T ratio) of cells pulsed with the MAGE-3 peptide. This result is virtually mirrored in the plasmid C74:1 immunised mice. In both cases, as in all cases shown in FIG. 20, there is no significant killing of cells pulsed with either no peptide or an irrelevant peptide. The cytotoxic activity of the C74:1 (Mage 3 in CDR-L3) group mice is in sharp contrast to the lack of CTL activity in the K2 (Native SC100) plasmid immunised mice. This difference in cytotoxicity suggests that, upon immunisation, the sequence encoding FLWGPRALV (SEQ ID NO:32) has been translated and that this peptide has been appropriately presented to CTLs. This supports a successful epitope graft an ImmunoBody type structure which elicits an immune response in immunised mice. Further evidence in the generation of CTLs is shown in those groups of mice immunised with plasmid C213:4 and also in those mice immunised with a combination of C74:1 and H8. Plasmid C213:4 also contains sequence encoding the peptide FLWGPRALV (SEQ ID NO:32) in CDR-L3, but also contains the T Helper epitope (TPPAYRPPNAPIL) (SEQ ID NO:31) in CDR-L1. The presence of the T helper epitope may be providing T cell help, as indicated by the fact that killing is occurring at a lower E:T ratio than seen in the C74:1 immunised group. Another observation from FIG. 20, is that relatively high cytotoxic activity seems to be occurring in the mice immunised with a combination of the plasmids C74:1 and H8 that encode both light and heavy chains in the same cell. This could have the effect of producing a whole ImmunoBody entity within the transfected cell. Presentation of the epitopes to antigen presenting cells could lead to cell killing, and to release of the whole ImmunoBody entity into the surrounding environment. This would then allow the targeting of Langerhan cells (specialised dendritic cells found in the skin) through CD64, the ligand being provided by the heavy chain portion of the ImmunoBody. This may account for the relatively higher amount of killing observed in this group.

Example 12

Preparation of Polypeptide-Fc Constructs (Signal Pigplus Tie2-FC and Mutants)

A protein domain of a molecule was cloned and spliced to human IgG1 Fc region. This would be recognised by CD64 receptor on dendritic cells be internalised and processed into peptides for presentation on class I and Class II MHC molecules. If these epitopes are high affinity self epitopes the T cells recognising them may have been deleted in the thymus. T cells recognising moderate affinity epitopes will still be presented but these epitopes will not be well represented on MHC molecules, as they will be outcompeted by the higher affinity epitopes. By changing the anchor residues that bind to MHC it is possible to generate high affinity peptides without altering T cell recognition (Rosenberg et al., (1998) *Nature Medicine* 4: 321-327).

Methods & Results cDNA synthesised from 5 µg of total RNA isolated from the cell line TF1 (grown in the presence of 200 units/ml GMCSF) was used as a template for the amplification of truncated Tie-2 (1-196 amino acids) using the primers: 5' primer, 5'-GAT CTC GAG ATT TGG GGA AGC ATG GAC-3' (SEQ ID NO:29), corresponding to the nucleotide sequence 128-154 of the Tie-2 gene with an additional Xho1 restriction site; and 3' primer, 5'-GAA GAT ATC TCC TCC TAT ATA CCT GGC CGA-3'(SEQ ID NO:30), corresponding to the nucleotide sequence 716-745 of the Tie-2 gene with a incorporated EcoRV site. The PCR fragment was cut and ligated into the Xho-1/EcoRV multiple cloning site of the mammalian expression vector Signal pigplus (R and D systems) inframe with a CD33 signal sequence and C terminal human IgG1 Fc tail to generate a secretory fusion protein. This plasmid was identified by restriction analysis and confirmed by DNA sequencing.

From this wild type plasmid five further constructs were generated by PCR mutagenesis. The "Quik™ Change Site Directed Mutagenesis" kit (Stratagene) was used according to the manufacturers protocol to switch specific amino acids in order to produce potential CTL epitopes using the designed primers Z84, Z95, Z101 and Z107 as listed in table 14.

TABLE 14

Primers used for site directed mutagenesis of the Signal pigplus Tie2-FC wild type construct

| Mutation | Primer | |
|---|---|---|
| Z84 | 5' | 5'-CCA GCT ACT TTA ACT ATG GTT GTG GAC AAG GGA G-3' (SEQ ID NO: 21) |
| | 3' | 5'-C TCC CTT GTC CAC AAC CAT AGT TAA AGT AGC TGG-3' (SEQ ID NO: 22) |
| Z95 | 5' | 5'-A GCC AGC TTA CTT CTC TGT GGA GTC AGC TTG GTC CTT TCT GG-3' (SEQ ID NO: 23) |
| | 3' | 5'-CC AGA AAG GAC CAA GCT GAC TCC ACA GAG AAG TAA GCT GGC T-3' (SEQ ID NO: 24) |
| Z101 | 5' | 5'-GCT TCC TTC CTA CTA GCT ACT TTA ACT ATG ACT GTG G-3' (SEQ ID NO: 25) |
| | 3' | 5'-C CAC AGT CAT AGT TAA AGT AGC TAG TAG GAA GGA AGC-3' (SEQ ID NO: 26) |
| Z107 | 5' | 5'-CAA GCT TCC TTA CTA CCA GCT ACT TTA ACT CTG ACT GTG C-3' (SEQ ID NO: 27) |
| | 3' | 5'-C CAC AGT CAC AGT TAA AGT AGC TGG TAG TAA GGA ACC TTG-3' (SEQ ID NO: 28) |

Nucleotides highlighted in red are the substituted bases required to code for the switched specific amino acid of the Epitope.

Z84 primers anneal to the nucleotide sequence from 524-557; Z95 primers: 160-201; Z101 primers: 512-548 And Z107 primers: 509-548 of the wild type Tie-2 gene. (Accession number L06139)

For one construct both Z95 and Z107 primers were utilised to incorporate two potential CTL epitopes. All site specific mutations were confirmed by DNA sequencing (Table 15).

TABLE 15

Alignment of wild type Tie-2 cDNA and amino acids with sequencing obtained from the incorporated site specific mutations present in the Signal pigplus Tie-2-FC constructs.

| | | | | | | | | | | |
|---|---|---|---|---|---|---|---|---|---|---|
| 518-544 | TTC | CTA | CCA | GCT | ACT | TTA | ACT | ATG | ACT | (SEQ ID NO: 5) | Wild type |
| | F | L | P | A | T | L | T | M | T | (SEQ ID NO: 6) | |
| 124-132 | TTC | CTA | CCA | GCT | ACT | TTA | ACT | ATG | GTT | (SEQ ID NO: 7) | Z84 |
| | F | L | P | A | T | L | T | M | V | (SEQ ID NO: 8) | |
| 167-193 | TTA | GTT | CTC | TGT | GGA | GTC | AGC | TTG | CTC | (SEQ ID NO: 9) | Wild type |
| | L | V | L | C | G | V | S | L | L | (SEQ ID NO: 10) | |
| 7-15 | TTA | CTT | CTC | TGT | GGA | GTC | AGC | TTG | GTC | (SEQ ID NO: 11) | Z95 |
| | L | L | L | C | G | V | S | L | V | (SEQ ID NO: 12) | |
| 521-547 | CTA | CCA | GCT | ACT | TTA | ACT | ATG | ACT | GTG | (SEQ ID NO: 13) | Wild type |
| | L | P | A | T | L | T | M | T | V | (SEQ ID NO: 14) | |
| 125-133 | CTA | CTA | GCT | ACT | TTA | ACT | ATG | ACT | GTG | (SEQ ID NO: 15) | Z101 |
| | L | L | A | T | L | T | M | T | V | (SEQ ID NO: 16) | |

TABLE 15-continued

Alignment of wild type Tie-2 cDNA and amino acids with sequencing obtained from the incorporated site specific mutations present in the Signal pigplus Tie-2-FC constructs.

```
515-541  TCC TTC CTA CCA GCT ACT TTA ACT ATG  (SEQ ID NO: 17)   Wild type
          S   F   L   P   A   T   L   T   M   (SEQ ID NO: 18)

123-131  TCC TTA CTA CCA GCT ACT TTA ACT GTG  (SEQ ID NO: 19)   Z107
          S   L   L   P   A   T   L   T   V   (SEQ ID NO: 20)
```

Numbers correspond to nucleotide bases and amino acids of Tie-2 wild type sequence (Accession number L06139)

Plasmids were sequenced using BigDye terminator cycle sequencing ready reaction (PE Applied Biosystems) and sequencing reactions were electrophoresed using the ABI prism 373A DNA sequencer (Applied Biosystems). Resulting DNA sequences were aligned with wild type cDNA (Accession no: L06139) obtained from the NIH database using the Blast 2 pairwise search programme. 293 human kidney cells were stably transfected with tie2-Fc and the protein recovered from the supernatant purified on a protein A column.

Human T cells recognising a peptide within the Tie2 molecule were cloned. These clones were shown to be of moderate affinity requiring 5 ug of peptide to give 50% maximum stimulation and are therefore representative of the T cells that have escaped thymic selection. Dendritic cells were fed with either Tie2 recombinant protein, peptide or the Tie2Fc construct and were then exposed to the T cell clone. FIG. 21 shows that the clone responded weakly to peptide, failed to respond at all to the recombinant protein but gave an excellent response to the Tie2Fc construct. Furthermore the response to the Tie2Fc construct could be blocked by an anti-CD64 antibody.

What is claimed is:

1. A method for stimulating a CD8 cytotoxic T cell response in a human patient, comprising administering to the patient a therapeutically effective amount of an antibody protein that includes (i) human Fcγ1, and (ii) a single heterologous CD8 cytotoxic T cell epitope, wherein the single heterologous CD8 cytotoxic T cell epitope has been substituted into a complementarity determining region (CDR) of the antibody protein that has similar size and charge as the epitope, and the first amino acid downstream of the epitope has been chosen from the group consisting of G, K, R, and S so that the epitope is cleaved, at its C-terminus, in the proteasome, to thereby elicit a major histocompatibility complex (MHC) class 1 response.

2. The method of claim 1, wherein the antibody protein comprises a heterologous Fab fragment.

3. The method of claim 2, wherein the Fab fragment is non-human.

4. The method of claim 3, wherein the Fab fragment is from mouse.

5. The method of claim 1, wherein the heterologous CD8 cytotoxic T cell epitope is a self-epitope.

6. The method of claim 5, wherein the self-epitope is a tumor epitope.

7. The method of claim 1, wherein the antibody protein is a monoclonal antibody protein.

8. The method of claim 1, wherein the antibody protein is administered intramuscularly.

9. The method of claim 1, wherein the antibody protein is administered intradermally.

10. The method of claim 1, wherein the antibody protein is administered for the treatment of cancer.

11. The method of claim 1, wherein the antibody protein is administered to the patient with an adjuvant.

12. A method for stimulating a CD8 cytotoxic T cell response in a human patient, comprising:

substituting a single heterologous CD8 cytotoxic T cell epitope for a complementarity determining region (CDR) of an antibody protein that includes human FcγI, the CDR having similar size and charge as the epitope, and the first amino acid downstream of the epitope being chosen from the group consisting of G, K, R, and S; and administering to the patient a therapeutically effective amount of the antibody protein, wherein the epitope is cleaved, at its C-terminus, in the proteasome, to thereby elicit a major histocompatibility complex (MHC) class 1 response.

13. The method of claim 12, wherein the heterologous CD8 cytotoxic T cell epitope is a self-epitope.

14. The method of claim 13, wherein the self-epitope is a tumor epitope.

15. The method of claim 12, wherein the therapeutically effective amount of the antibody protein is administered intramuscularly.

16. The method of claim 12, wherein the therapeutically effective amount of the antibody protein is administered intradermally.

17. The method of claim 12, wherein the therapeutically effective amount of the antibody protein is administered for the treatment of cancer.

18. The method of claim 12, wherein the therapeutically effective amount of the antibody protein is administered to the patient with an adjuvant.

* * * * *